United States Patent
Dushyantha et al.

(10) Patent No.: US 12,178,690 B2
(45) Date of Patent: Dec. 31, 2024

(54) ABSORBENT PAD FOR A GARMENT AND A GARMENT COMPRISING THE ABSORBENT PAD

(71) Applicant: MAS Innovation (Private) Limited, Battaramulla (LK)

(72) Inventors: Mapitiyage Don Janith Dushyantha, Piliyandala (LK); Ganewaththe Don Thimathi Surajika Abeyrathna, Alawwa (LK); Kirivitige Asel Sathsara Fernando, Borella (LK); Kahandawala Arachchige Don Lakshan Sandaruwan, Malabe (CA); Wijesinghe Mudiyanselage Shashika Virajinie Wijesinghe, Gampaha (LK); Dharini Alexandra Speldewinde, Borella (LK); Ginnymarie Buddhika Mendis, Moratuwa (LK); Hettiarachchige Aasie Ayanthika Wijesinghe, Kaduwela (LK)

(73) Assignee: MAS Innovation (Private) Limited, Battaramulla (LK)

(*) Notice: Subject to any disclaimer, the term of this patent is extended or adjusted under 35 U.S.C. 154(b) by 0 days.

(21) Appl. No.: 18/506,253

(22) Filed: Nov. 10, 2023

(65) Prior Publication Data
US 2024/0164957 A1    May 23, 2024

(30) Foreign Application Priority Data

Nov. 18, 2022 (SG) .......................... 10202260133X
Dec. 16, 2022 (SG) .......................... 10202260482Y
Jun. 12, 2023 (SG) .......................... 10202301653W

(51) Int. Cl.
*A61F 13/15* (2006.01)
*A61F 13/42* (2006.01)
(Continued)

(52) U.S. Cl.
CPC .............. *A61F 13/42* (2013.01); *A61F 13/47* (2013.01); *A61F 13/51121* (2013.01);
(Continued)

(58) Field of Classification Search
CPC ............ A61F 13/15756; A61F 13/2031; A61F 13/2034; A61F 13/2057; A61F 13/2074;
(Continued)

(56) References Cited

U.S. PATENT DOCUMENTS 10,441,479 B2   10/2019   Griffiths
10,441,480 B2   10/2019   Griffiths
(Continued)

FOREIGN PATENT DOCUMENTS

AU    2022242175 A1    9/2023
AU    2021220546 B2    10/2023
(Continued)

*Primary Examiner* — Jacqueline F Stephens
(74) *Attorney, Agent, or Firm* — Patterson + Sheridan, LLP

(57) ABSTRACT

The present disclosure generally relates to an absorbent pad for use in a garment and a garment having the absorbent pad. The absorbent pad includes a liquid impermeable barrier layer; a functional assembly attached to the barrier layer; and a peripheral assembly attached to a periphery of the functional assembly, at least part of the peripheral assembly being liquid impermeable. The functional assembly includes an absorbent layer attached to the barrier layer, the absorbent layer for absorbing liquid; and a wicking layer attached to the absorbent layer. The wicking layer is arranged to face towards a skin of a user when in use. The wicking layer transfers liquid to the absorbent layer. The wicking layer and the absorbent layer are attached at a plurality of discrete points between them to facilitate liquid transfer from the wicking layer to the absorbent layer via areas around the discrete points.

19 Claims, 32 Drawing Sheets

(51) Int. Cl.
*A61F 13/47* (2006.01)
*A61F 13/511* (2006.01)
*A61F 13/539* (2006.01)

(52) U.S. Cl.
CPC ...... *A61F 13/539* (2013.01); *A61F 2013/422* (2013.01); *A61F 2013/5113* (2013.01); *A61F 2013/53908* (2013.01)

(58) Field of Classification Search
CPC .. A61F 13/208; A61F 13/475; A61F 13/4755; A61F 2013/15878; A61F 2013/15861; A61F 2013/1591
See application file for complete search history.

(56) References Cited

U.S. PATENT DOCUMENTS

| | | | |
|---|---|---|---|
| 11,590,034 B2 | 2/2023 | Deshaies et al. | |
| 11,701,267 B2 | 7/2023 | Greco et al. | |
| 2005/0256479 A1* | 11/2005 | Carlucci | A61F 13/42 604/362 |
| 2008/0234644 A1* | 9/2008 | Hansson | A61L 15/56 604/360 |
| 2018/0014983 A1* | 1/2018 | Jayasuriya | A61L 15/26 |
| 2018/0064584 A1* | 3/2018 | Van De Maele | B32B 3/28 |
| 2018/0064585 A1* | 3/2018 | Park | A61F 13/47218 |
| 2020/0000649 A1 | 1/2020 | Griffiths | |
| 2020/0222256 A1 | 7/2020 | Chong | |
| 2020/0375817 A9 | 12/2020 | Griffiths | |
| 2021/0030605 A1* | 2/2021 | Kajanthan | A61F 13/4755 |
| 2021/0282469 A1 | 9/2021 | Siriwardena | |
| 2023/0082418 A1 | 3/2023 | Mellos | |
| 2023/0128088 A1 | 4/2023 | Deshaies et al. | |
| 2023/0240904 A1 | 8/2023 | Newman et al. | |

FOREIGN PATENT DOCUMENTS

| | | |
|---|---|---|
| EP | 4250988 A1 | 10/2023 |
| GB | 2586813 A | 3/2021 |
| GB | 2588289 A | 4/2021 |
| GB | 2615694 A | 8/2023 |
| WO | 2023026285 A1 | 3/2023 |
| WO | 2023048620 A1 | 3/2023 |
| WO | 2023048621 A1 | 3/2023 |
| WO | 2023048622 A1 | 3/2023 |
| WO | 2023057075 A1 | 4/2023 |
| WO | 2023057076 A1 | 4/2023 |
| WO | 2023057096 A1 | 4/2023 |
| WO | 2023130159 A1 | 7/2023 |
| WO | 2023155997 A1 | 8/2023 |
| WO | 2023186944 A1 | 10/2023 |

* cited by examiner

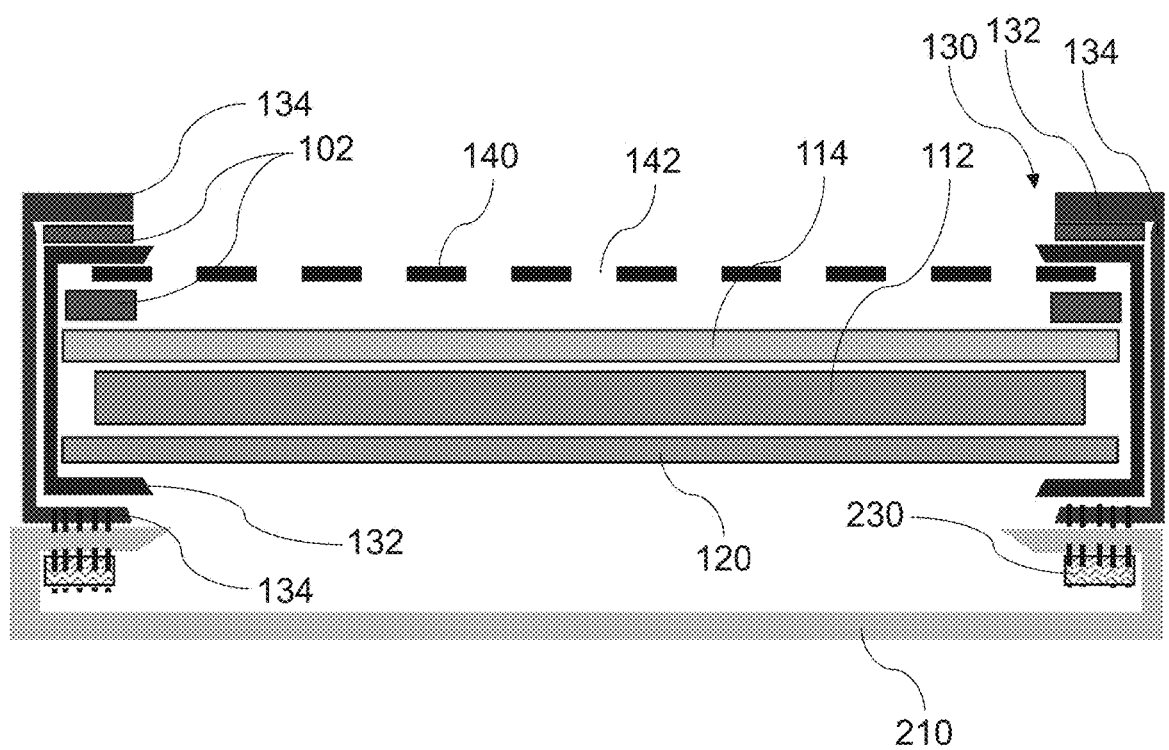
Figure 3A
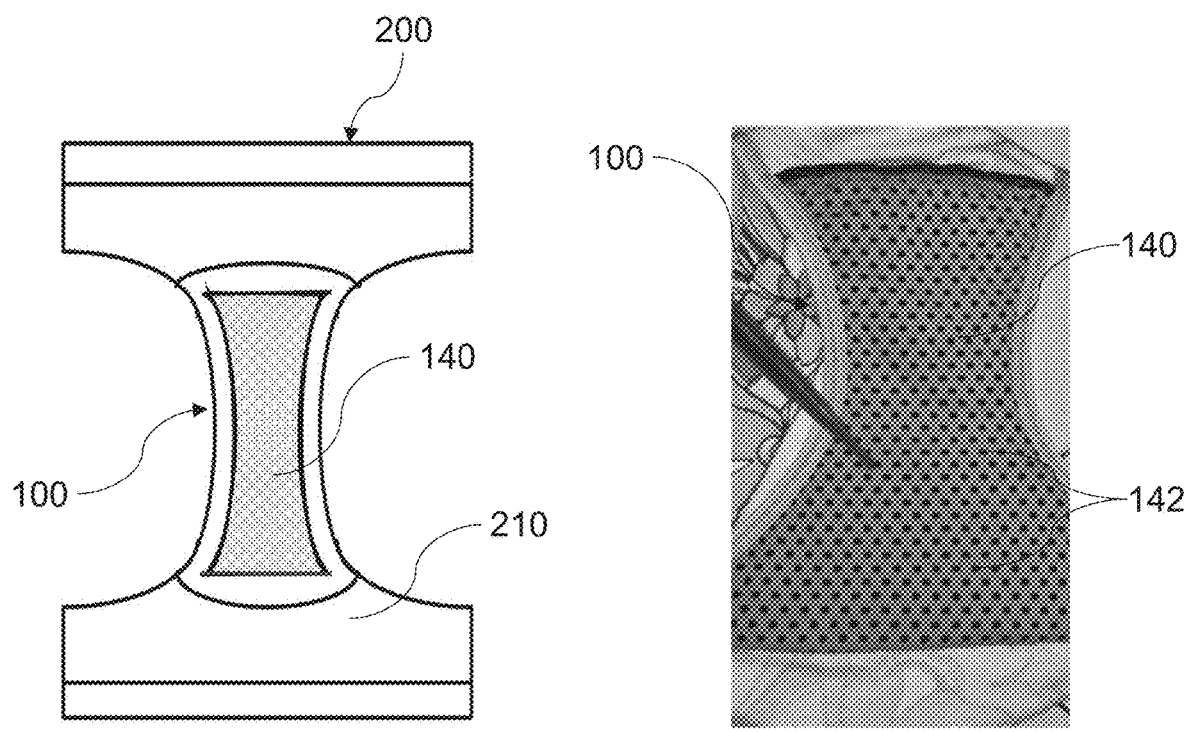
Figure 3B
Figure 3C

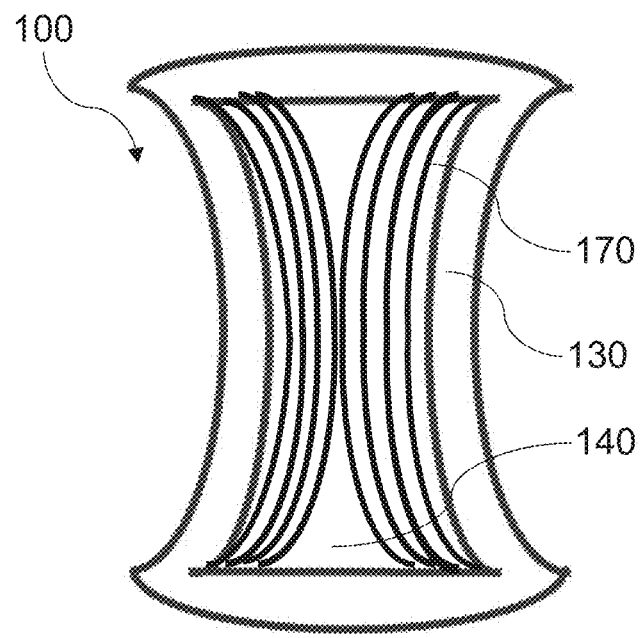
Figure 14A
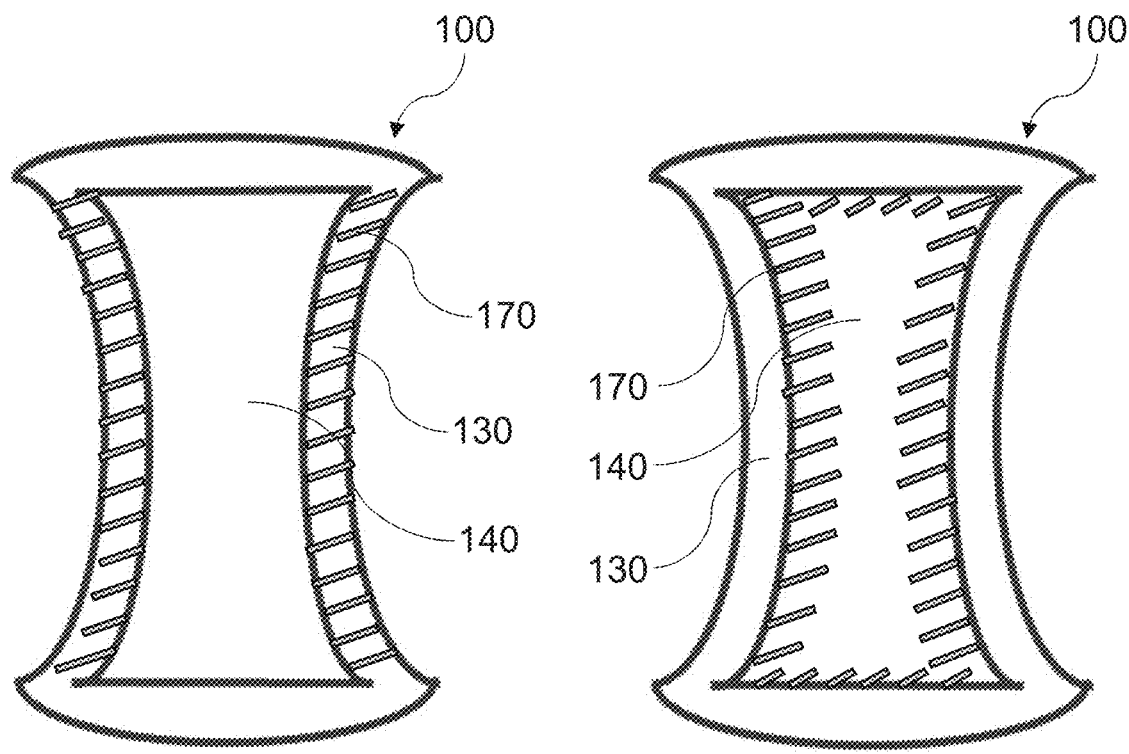
Figure 14B
Figure 14C

ABSORBENT PAD FOR A GARMENT AND A GARMENT COMPRISING THE ABSORBENT PAD

CROSS REFERENCE TO RELATED APPLICATIONS

The present disclosure claims the benefit of Singapore Patent Application No. 10202260133X filed on Nov. 18, 2022, Singapore Patent Application No. 10202260482Y filed on Dec. 16, 2022, and Singapore Patent Application No. 10202301653W filed on Jun. 12, 2023, each of which is incorporated in its entirety by reference herein.

TECHNICAL FIELD

The present disclosure generally relates to an absorbent pad for a garment and a garment comprising the absorbent pad. More particularly, the present disclosure describes various embodiments of the absorbent pad for use in a garment, such as a panty, as well as the garment comprising the absorbent pad.

BACKGROUND

Absorbent garments such as reusable and washable absorbent undergarments are worn with the purpose of absorbing bodily fluids. These bodily fluids include vaginal discharge, urine, menstrual fluid, sweat, and breast milk. Many people suffer from involuntary excretion of bodily fluids and there are few garments that have been designed to absorb such excretions that are functional and comfortable to the user wearing it.

For example, a woman who is menstruating will generally use a tampon or a sanitary pad, in addition to wearing an undergarment, to keep her outer garments from being soiled by menstrual fluid. While the tampon or pad often absorbs all the liquid flow, unexpected leaks can still occur. To avoid such leaks, she can instead choose to wear an adult brief, which offers a larger area of protection and may be particularly useful for women experiencing heavy menstrual flows. Adult briefs may also be useful for people who have urinary incontinence. However, adult briefs tend to be bulky and unattractive, making it difficult to conceal them under outer clothing, which may cause embarrassment to the user. Some disadvantages of wearing adult briefs and sanitary pads include prolonged exposure to wetness, which may result in discomfort, irritant dermatitis, and/or infections. Further, pads/tampons may be occasionally positioned incorrectly and adult briefs may be wrapped too loosely, both resulting in leakage. In addition, these conventional products are generally disposable, meaning that the environmental and economic costs can be significant.

The bulkiness of conventional products means that they do not allow the user to easily wear low-coverage undergarments. For example, absorbent pads must be placed into large, maximum-coverage undergarments that are capable of sufficiently containing them, while diapers and absorbent undergarments are generally large to adequately address the incontinence of the user. Therefore, someone who prefers thong-style or low-rise bikini underwear is often forced to choose between wearing preferred underwear, which risks leakage onto their outer clothing, or wearing a cumbersome and unattractive garment that would ensure that all leaks are prevented.

Therefore, in order to address or alleviate at least one of the aforementioned problems and/or disadvantages, there is a need to provide an improved absorbent pad for use in a garment and an improved garment comprising the absorbent pad.

SUMMARY

According to a first aspect of the present disclosure, there is an absorbent pad for use in a garment. The absorbent pad comprises:
  a liquid impermeable barrier layer;
  a functional assembly attached to the liquid impermeable barrier layer, the functional assembly comprising:
    an absorbent layer attached to the liquid impermeable barrier layer, the absorbent layer for absorbing liquid; and
    a wicking layer attached to the absorbent layer, the wicking layer arranged to face towards a skin of a user when in use, the wicking layer for transferring liquid to the absorbent layer; and
  a peripheral assembly attached to a periphery of the functional assembly, at least part of the peripheral assembly being liquid impermeable,
  wherein the wicking layer and the absorbent layer are attached at a plurality of discrete points between them to facilitate liquid transfer from the wicking layer to the absorbent layer via areas around the discrete points.

According to a second aspect of the present disclosure, there is garment comprising a fabric body; an absorbent pad attached to the fabric body; and a liquid impermeable barrier layer being part of the fabric body and/or part of the absorbent pad. The absorbent pad comprises:
  a functional assembly attached to the liquid impermeable barrier layer, the functional assembly comprising:
    an absorbent layer attached to the liquid impermeable barrier layer, the absorbent layer for absorbing liquid; and
    a wicking layer attached to the absorbent layer, the wicking layer arranged to face towards a skin of a user when in use, the wicking layer for transferring liquid to the absorbent layer; and
  a peripheral assembly attached to a periphery of the functional assembly, at least part of the peripheral assembly being liquid impermeable,
  wherein the wicking layer and the absorbent layer are attached at a plurality of discrete points between them to facilitate liquid transfer from the wicking layer to the absorbent layer via areas around the plurality of discrete points.

An absorbent pad for use in a garment and a garment comprising the absorbent pad according to the present disclosure are thus disclosed herein. Various features, aspects, and advantages of the present disclosure will become more apparent from the following detailed description of the embodiments of the present disclosure, by way of non-limiting examples only, along with the accompanying drawings.

BRIEF DESCRIPTION OF THE DRAWINGS

FIGS. 3A to 3C are various illustrations of a top layer of the absorbent pad.

FIGS. 14A to 14C are various illustrations of the absorbent pad comprising hydrochromic materials.

DETAILED DESCRIPTION

Figure 1A:
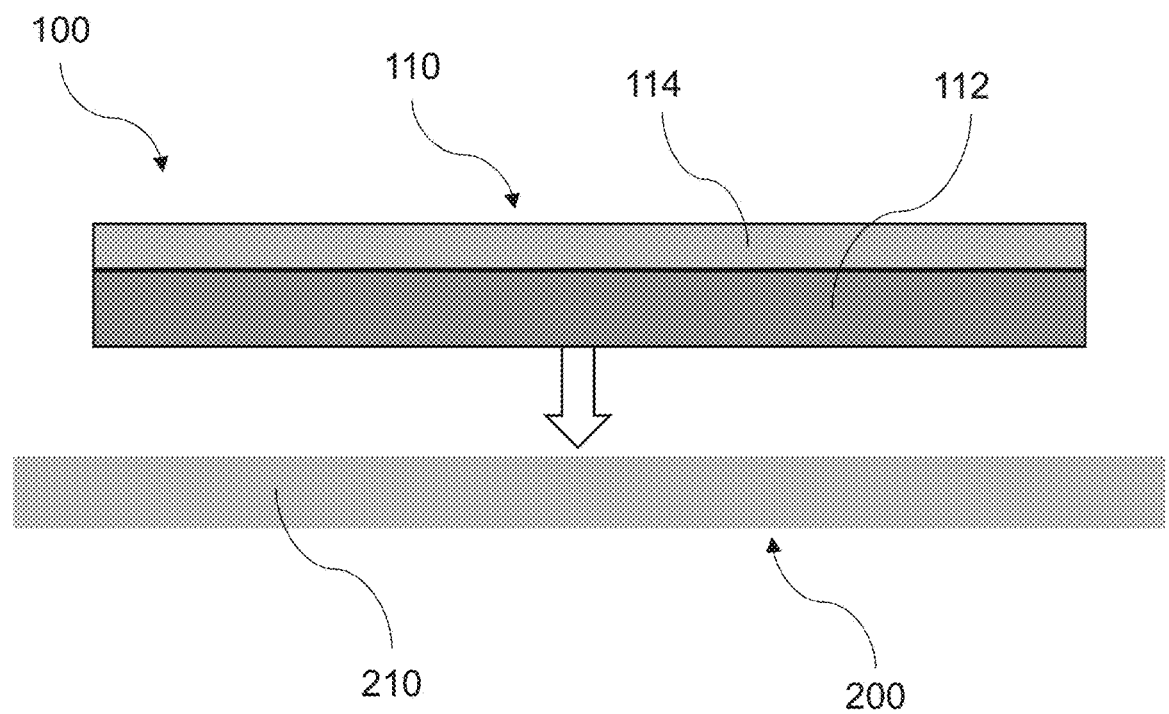
FIGS. 1A to 1C are various illustrations of an absorbent pad for a garment, in accordance with embodiments of the present disclosure.

For purposes of brevity and clarity, descriptions of embodiments of the present disclosure are directed to an absorbent pad for use in a garment and a garment comprising the absorbent pad, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognised by an individual having ordinary skill in the art, i.e. a skilled person, that the present disclosure may be practiced without specific details, and/or with multiple details arising from combinations of aspects of particular embodiments. In a number of instances, known systems, methods, procedures, and components have not been described in detail so as to not unnecessarily obscure aspects of the embodiments of the present disclosure.

In embodiments of the present disclosure, depiction of a given element or consideration or use of a particular element number in a particular figure or a reference thereto in corresponding descriptive material can encompass the same, an equivalent, or an analogous element or element number identified in another figure or descriptive material associated therewith.

References to "an embodiment/example", "another embodiment/example", "some embodiments/examples", "some other embodiments/examples", and so on, indicate that the embodiment(s)/example(s) so described may include a particular feature, structure, characteristic, property, element, or limitation, but that not every embodiment/example necessarily includes that particular feature, structure, characteristic, property, element, or limitation. Furthermore, repeated use of the phrase "in an embodiment/example" or "in another embodiment/example" does not necessarily refer to the same embodiment/example.

The terms "comprising", "including", "having", and the like do not exclude the presence of other features/elements/steps than those listed in an embodiment. Recitation of certain features/elements/steps in mutually different embodiments does not indicate that a combination of these features/elements/steps cannot be used in an embodiment. The terms "a" and "an" are defined as one or more than one. The use of "/" in a figure or associated text is understood to mean "and/or" unless otherwise indicated. The recitation of a particular numerical value or value range herein is understood to include or be a recitation of an approximate numerical value or value range.

The term "set" is defined as a non-empty finite organisation of elements that mathematically exhibits a cardinality of at least one (e.g. a set as defined herein can correspond to a unit, singlet, or single-element set, or a multiple-element set), in accordance with known mathematical definitions. The terms "first", "second", etc. are used merely as labels or identifiers and are not intended to impose numerical requirements on their associated terms.

Figure 1B:
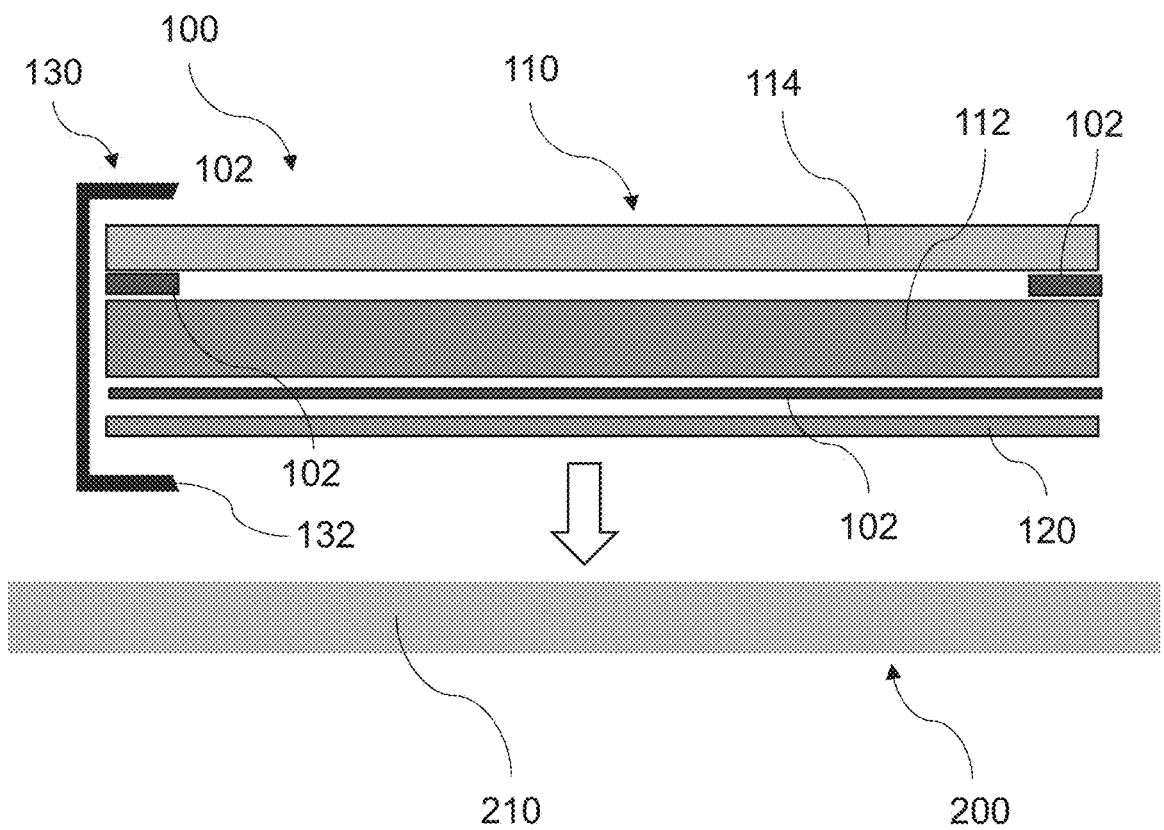

In representative or exemplary embodiments of the present disclosure, there is an absorbent pad 100, such as in but not limited to the form of a gusset, for use in a garment 200 as illustrated in FIGS. 1A and 1B. For example, the absorbent pad 100 is attachable to a fabric body 210 of the garment 200. The garment 200 may be an intimate garment or undergarment worn by a user particularly at parts of the body where there may be excretions of bodily fluids. For example, the garment 200 may be, but is not limited to, brassieres, panties, lingerie, active wear, sportswear, swimwear, and similar close-fitting or form-fitting garments. When attached to a garment, the absorbent pad 100 may be affixed so that they are fully attached to the fabric body 210. In some embodiments, the absorbent pad 100 may only be attached at certain areas, such as at the lengthwise peripheries (in whole or in part) of the absorbent pad 100 to provide a floating effect. Without wishing to be bound by theory, it is believed that this arrangement makes the garment 200 and the absorbent pad 100 more stretchable, which improves comfort and freedom of movement for the user.

The absorbent pad 100 includes a functional assembly 110 that has an absorbent layer 112 for absorbing liquid, such as the bodily fluids. The functional assembly 110 also has a wicking layer 114 that is attached to the absorbent layer 112 for transferring liquid to the absorbent layer 112. The wicking layer 114 is arranged to face towards a skin of the user when in use. In some embodiments, the functional assembly 110 includes a functional layer having an upper portion with the wicking properties of the wicking layer 114, and a lower portion having the absorbent properties of the absorbent layer 112.

In many embodiments as shown in FIG. 1B, the absorbent pad 100 includes a liquid impermeable barrier layer 120, wherein the functional assembly 110 is attached to the liquid impermeable barrier layer 120. Specifically, the absorbent layer 112 is attached to the liquid impermeable barrier layer 120, such that liquid absorbed by the absorbent layer 112 is prevented from leaking out of the absorbent pad 100 by the liquid impermeable barrier layer 120. The absorbent pad 100 includes a peripheral assembly 130 attached to a periphery of the functional assembly 110, at least part of the peripheral assembly 130 being liquid impermeable. For example, the peripheral assembly 130 includes a liquid impermeable sealing element 132 attached to peripheries of the functional assembly 110 and liquid impermeable barrier layer 120. For example, the peripheral assembly 130 includes an adhesive material.

As used herein, the term "adhesive" or "adhesive material" is a material that enables objects to be adhered to each other. For example, the adhesive material may include a material that becomes liquid impermeable after curing, such as a thermoplastic or thermoset glue. For example, the adhesive material may be in the form of liquid glue, such as hot-melt glue, drop-on-demand glue, line-on-demand glue, liquid resin, or the like, or combinations thereof. For example, the adhesive material may be in the form of an adhesive film or tape, such as a single-sided or double-sided adhesive film or tape.

Figure 1C:
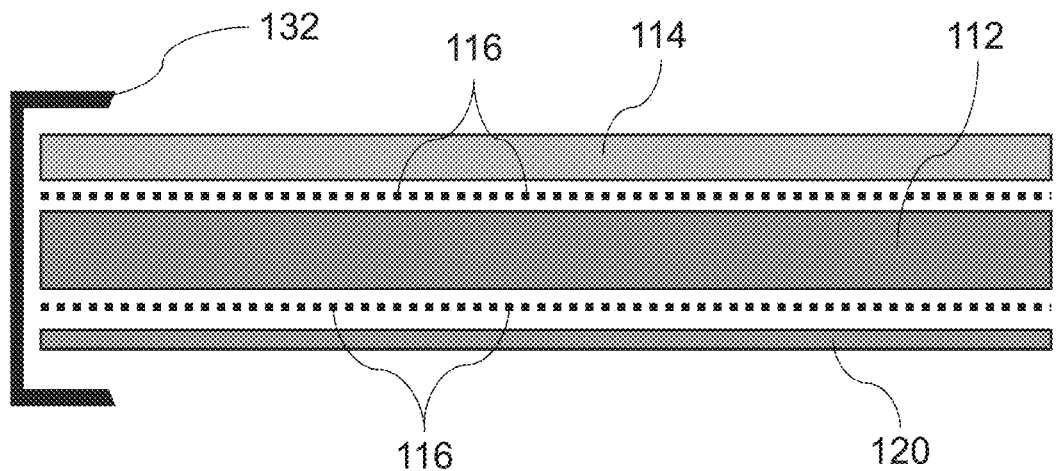

More particularly and further as shown in FIG. 1C, the wicking layer 114 and the absorbent layer 112 are attached at a plurality of discrete points 116 between them to facilitate liquid transfer. The absorbent and wicking layers 112,114 can be attached together using various means that physically link the absorbent and wicking layers 112,114 together at the plurality of discrete points 116 between them to facilitate liquid transfer. Specifically, the liquid transfer occurs from the wicking layer 114 to the absorbent layer 112 via areas around the discrete points 116. Areas of the absorbent and wicking layers 112,114 are directly attached to each other at these discrete points 116 and areas of the absorbent and wicking layers 112,114 that are around these discrete points 116 are arranged closer to each other. The closer proximity of the absorbent and wicking layers 112,114 at these areas around the discrete points 116 advantageously improves the efficiency of liquid transfer from the wicking layer 114 to the absorbent layer 112 via these areas. More areas of the absorbent and wicking layers 112,114 are brought closer together to increase the liquid transfer efficiency, as compared to existing products where the layers may only be attached along their peripheries.

Moreover, without wishing to be bound by theory, it is believed that this attachment of the absorbent and wicking layers 112, 114 using the discrete points 116 also enhances comfort for the user, and may lead to a more compact absorbent pad 100 compared to existing products. It will be appreciated that the discrete points 116 can be located anywhere and/or over any area of the absorbent and wicking layers 112,114. For example, the discrete points 116 are distributed over substantial portions of the absorbent and wicking layers 112,114 and/or peripheries of the absorbent and wicking layers 112,114, such as throughout the absorbent and wicking layers 112, 114 or only at their peripheries. For example, the discrete points 116 are located at the interfaces and/or the peripheries of the layers that are attached together, such as between the wicking layer 114 and the absorbent layer 112 or between the absorbent layer 112 and the barrier layer 120. It will be appreciated that the discrete points 116 can be located anywhere and/or over any area of the absorbent and barrier layers 112,120.

In some embodiments, the absorbent and wicking layers 112,114 are attached together by knitting. Specifically, the absorbent and wicking layers 112,114 are knitted together with cross-linking yarns at the discrete points 116. The absorbent layer 112 includes absorbent yarns formed from a liquid absorbent material, and the wicking layer 114 includes wicking yarns formed from a wicking material. The absorbent yarns are intermittently inter-looped and interconnected with the wicking yarns. For example, each of the absorbent yarns has a looping structure and each of the wicking yarns has a looping structure, such that each of the absorbent yarns is held by each loop of the wicking yarns and vice versa, thereby forming the cross-linking yarns at the discrete points 116 between the absorbent layer 112 and wicking layer 114.

Various methods of knitting include, but are not limited to, flat knitting, weft knitting, or warp knitting. For example, the absorbent and wicking layers 112,114 are knitted together as a unitary layer that has both wicking and absorbent functions, i.e. the functional assembly 110 includes a single unitary layer for the wicking and absorbent functions. The barrier layer 120 may then be attached to the single unitary layer, such as by glue lamination or ultrasonic lamination.

In some embodiments, the absorbent and wicking layers 112,114 are attached together by lamination. The discrete points 116 preferably include an adhesive material. For example, the adhesive material may be applied to one or both layers to be attached together using a roller lamination apparatus (e.g. dot roller), which may supply micro-level dots with a suitable density, i.e. dots per unit area, which density can be varied based upon the requirement of the absorbent pad 100 being created. Any suitable density of glue dots across the entirety of the second surface of the wicking layer and the first surface of the absorbent layer may be used, provided that it provides the desired effect. For example, a suitable density of glue dots may be provided by a glue concentration of from 4 to 12 grams per square meter (GSM) between the absorbent and wicking layers 112,114. The roller lamination has micro level dots with given density and can be varied based on the requirement. The glue lamination may include glue bonding with hot melt glue/ liquid resin bonding by nozzle extrusion/glue spray and liquid resin bonding by screen printing/template printing.

The functional assembly 110 may be attached to the barrier layer 120 in a similar manner using a corresponding plurality of discrete points 116. For example, this way of attachment can improve efficiency of vapour transfer from the barrier layer 120 to the functional assembly 110 and thereby improve breathability. Additionally or alternatively, the absorbent pad 100 may include a set of adhesive films 102 for bonding various layers, components, and/or parts of the absorbent pad 100. For example as shown in FIG. 1B, peripheries of the absorbent and wicking layers 112,114 are attached together by an adhesive film 102, in addition or alternatively to the discrete points 116. For example, peripheries of the absorbent and barrier layers 112,120 are attached together by an adhesive film 102. For example, the absorbent and barrier layers 112,120 are wholly attached together by an adhesive film 102, i.e. the adhesive film 102 may be applied across the entire surfaces between the functional assembly 110 and barrier layer 120.

The adhesive film 102 may include an adhesive tape, liquid glue, or hotmelt powder glue). When the adhesive film 102 is an adhesive tape, the tape may be a double-sided adhesive tape and said tape may have a single layer or multiple layers where said multiple layers may have one or more functions, such as liquid barrier functions, elastic functions, etc. For example, the adhesive tape is a Bemis tape. When the adhesive is a liquid glue, the glue may be a hot melt glue, a liquid resin or combinations thereof (e.g. the adhesive may be a hot melt glue/liquid resin bonding by nozzle extrusion or liquid resin bonding by screen printing/ template printing). Alternatively, the adhesive film 102 may be replaced by an adhesive or bonding process such as ultrasonic bonding. In some cases, the adhesive film 102 may be replaced by stitching.

The wicking layer 114 is capable of acquiring and distributing liquid or moisture to the underlying absorbent layer 112. Specifically, when the garment 200 comprising the absorbent pad 100 is worn by the user, the wicking layer 114 faces the user's body/skin and serves to transport bodily fluids produced by the user's body to the absorbent layer 112. In other words, the wicking layer 114 transports liquid from its upper interface, which may be in direct contact with the user's skin, to its lower interface that is attached to the upper interface of the absorbent layer 112. The wicking layer 114 may be made from fibres or yarns made with fibres, where said fibres and yarns are selected from one or more of the group consisting of polyamide, polyester, polyolefin, polyurethane, polyacrylonitrile, natural cellulose, regenerated cellulose, regenerated cellulose derivatives (i.e. cellulose acetate and cellulose triacetates), natural protein and regenerated protein. The wicking layer 114 may be produced using technologies such as knitting (warp knitting such as raschel Tricot, weft knitting such as circular or flat), weaving, non-woven methods (blow spinning, staple non-woven, spun laid, air-laid, needle punched, thermal bonded, hydro-entangled, chemical bonded and so forth), electro-spinning, force-spinning, etc. Additionally, the wicking layer 114 may also include one or more of the coatings, treatments encapsulation or entrapments, which would enhance its liquid and moisture management functionality, such as rate of wicking, wicking capacity, rate of spreading and distribution, one-way liquid transport, etc.

The material of the wicking layer 114 may be naturally moisture-wicking and/or be treated to become moisture-wicking. For example, the wicking material may be 100% polyester fabric with French Terry knit and a denier differential across the two interfaces of the wicking layer 114 that assists in moving the liquid from the upper interface of the wicking layer 114 to the lower interface that is attached to the upper interface of the absorbent layer 112. Other suitable wicking materials include blends of polyester, polypropylene, polyethylene, nylon, regenerated materials (e.g. viscose blends), natural fibres (e.g. bamboo), and cotton. The wicking layer 114 may optionally have triangular ridge structures of French Terry knitting facing the user's skin, and the advantage of these structures is that less surface area of the upper interface of the wicking layer 114 comes into contact with the skin and therefore reduces any sensation of feeling wetness against the skin. The wicking layer 114 may optionally have flat structures with a capillary gradient to generate differential capillary forces that move the liquid.

As an example, the wicking layer 114 may have or may be made of a material that is 51% cotton and one or both interfaces of the wicking layer 114 may be treated with a hydrophilic material or composition (e.g. polyethylene oxide, polyvinyl alcohol, polyacrylamide, poly acrylic acid, polyvinyl pyrrolidone, hydrophilic silicones, or hydrophilic polyurethanes) and/or a hydrophobic material or composition (e.g. silicones, polyfluoroalkyl acrylates, polyacrylates, polyurethanes, or waxes) to create a net hydrophilic gradient across the wicking layer 114. In other words, the upper interface that may be in direct contact with the user's skin may be less hydrophilic/more hydrophobic, whereas the lower interface may be more hydrophilic/less hydrophobic. For example, the upper interface may be treated with a hydrophobic material and/or the lower interface may be treated with a hydrophilic material. This results in a combination of a "pushing" force generated by the hydrophobic properties of the upper interface and a "pulling" force generated by the hydrophilic properties of the lower interface that may wick any moisture or liquid through the wicking layer 114 and away from the user. The hydrophilic and hydrophobic materials or compositions may be applied to the wicking layer 114 using any method known to the skilled person.

Additionally, the differential capillary forces on either interface of the wicking layer 114 can be created by the fabric structure of the wicking layer 114 where the lower interface has smaller pore sizes in comparison to the upper interface. This pore combination creates funnel-like structures through the wicking layer 114 in cross-section, where liquid is pulled from the upper interface with the larger pore sizes to the lower interface with the smaller pore sizes, due to the differential capillary pressure.

The rate of wicking through the wicking layer 114 may be controlled to be faster or slower. The rate may be set at a maximum rate of absorption of the wicking layer 114 to ensure that all, substantially all, or at least a significant percentage of, the liquid is absorbed by the absorbent layer 112 and does not leak beyond the confines of the absorbent pad 100 and garment 200. The rate of wicking may be controlled by the density, thickness, or composition of the wicking layer 114 and/or by the amount and type of hydrophobic and/or hydrophilic material applied to the wicking layer 114. In another embodiment, the rate of wicking may be set such that the upper interface of the wicking layer 114 that may be in direct contact with the user feels "dry" or mostly dry to the user.

In some embodiments, the wicking layer 114 may include an antimicrobial agent or substance. For example, the antimicrobial substance may be one or more substances selected from the group consisting of a silver-containing substance, titanium dioxide, a quaternary silane, hydrogen peroxide, triclosan, and zinc pyrithione. Additionally or alternatively, the wicking layer 114 may include an anti-odour agent or substance that combats odour. For example, the substance that combats odour may be one or more substances selected from the group consisting of nanoparticles with acid-neutralising pockets, high surface area mineral compositions, high surface area ceramic compositions, high surface area clay compositions, and plant-based deodorizers such as essential mint oils. Further additionally or alternatively, the wicking layer 114 may include a stain-resistant, stain-release, or stain-proof agent or substance.

Figure 2A:
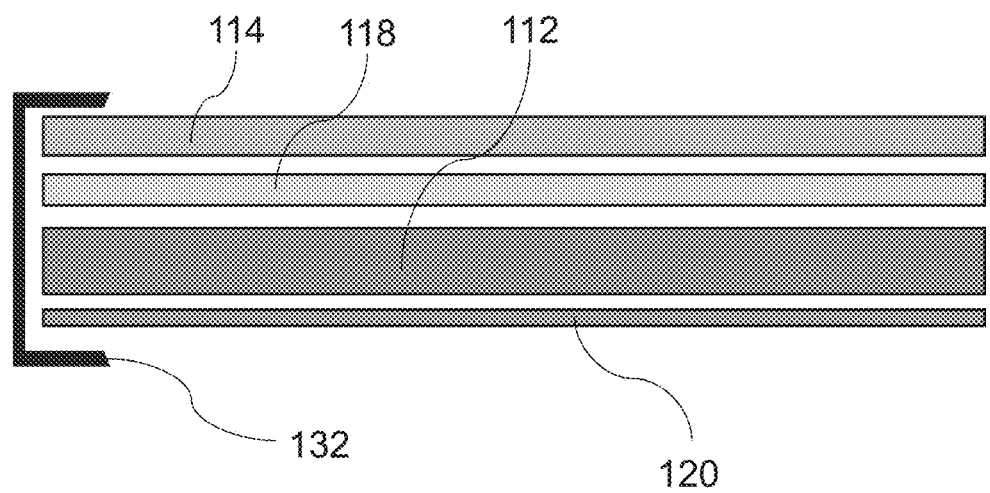
FIGS. 2A and 2B are various illustrations of a wicking layer of the absorbent pad.

In some embodiments as shown in FIG. 2A, the wicking layer 114 includes or may be an acquisition and distribution layer 118 to facilitate liquid transfer from the wicking layer 114 to the absorbent layer 112 or to multiple absorbent layers 112 below the wicking layer 114. The acquisition and distribution layer 118 refers to a layer that allows liquid to be distributed both across the width-wise and length-wise directions of the absorbent pad 100, so that the entire absorbent layer(s) 112 is utilised. This may be accomplished by any means discussed herein, such as by the embossing/debossing of the wicking layer 114 discussed above. It may also be accomplished through the use of specific materials, such as a 100% polyester French terry fabric or a 100% polyester double terry fabric. Other suitable materials and structures for the acquisition and distribution layer 118 may include those described above for the wicking layer 114.

Figure 2B:
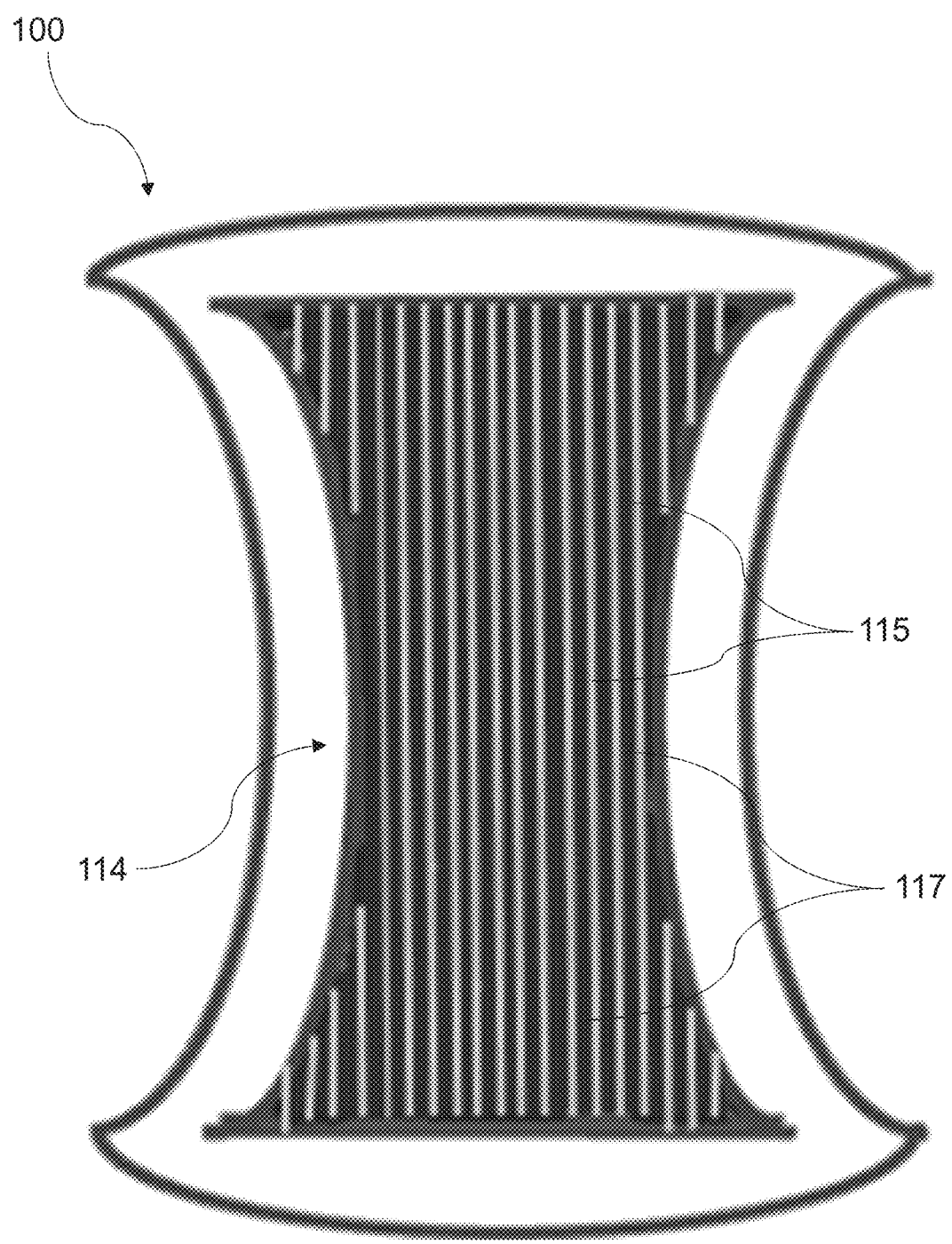

In some embodiments, the wicking layer 114 may include one or more of a hydrophilic material, a hydrophobic material, and a hydrochromic material. For example as shown in FIG. 2B, the wicking layer 114 includes an array of hydrophobic yarns 115 and hydrophilic yarns 117 that form channels for guiding liquid flow. The hydrophobic yarns 115 repel water towards the adjacent hydrophilic yarns 117 which guide the water to flow along those hydrophilic yarns 117 and thereby improve liquid transport across the wicking layer 114. The hydrophobic yarns 115 are treated to make them water repellent, while the hydrophilic yarns 117 treated such that the yarns 115,117 collectively form channels that guide the liquid flow (similar to how liquid flow is guided by channels in an example as shown in FIG. 4D). These channels allow for greater movement and spread of liquid over a larger surface area for quicker evaporation.

The liquid-repelling properties of the hydrophobic material 115 also provide stain-free/stain-release properties that may enhance aesthetics or introduce a visual effect to the absorbent pad 100. Optionally, the wicking layer 114 includes the hydrochromic material that is configured to change colour in response to contact with liquid. The hydrochromic material may allow one to introduce various colours and designs to the aesthetic appearance of the absorbent pad 100. For example, the hydrochromic material includes hydrochromic prints and water-based pigments. An example of a hydrochromic print is a printing paste comprising an ink that is normally opaque coloured but will become transparent when wetted. Such printing ink can be used beneath a white-coloured coating to incorporate hidden effects that become exposed when wetted. The printed area would return to its original opaque coloured appearance when dried.

In some embodiments, the functional assembly 110 includes the absorbent pad 112 and instead of or in addition to the wicking layer 114, the functional assembly 110 includes a liquid transport layer attached to the absorbent layer 112. The liquid transport layer is arranged to face towards the user's skin when in use, and is for transferring liquid to the absorbent layer 112. Further, the liquid transport layer includes an array of hydrophobic and hydrophilic materials, such as described above for the wicking layer 114, for guiding liquid flow across the functional assembly 110. It will be appreciated that various aspects of the absorbent pad 100 described in other embodiments herein may apply equally to these embodiments with the liquid transport layer.

In some embodiments, the functional assembly 110 includes the absorbent pad 112 and instead of or in addition to the wicking layer 114, the functional assembly 110 includes a liquid detection layer attached to the absorbent layer 112. The liquid detection layer is arranged to face towards the user's skin when in use, and is for transferring liquid to the absorbent layer 112. Further, the liquid detection layer includes a hydrochromic material configured to change colour in response to contact with liquid. It will be appreciated that various aspects of the absorbent pad 100 described in other embodiments herein may apply equally to these embodiments with the liquid detection layer.

The absorbent layer 112 may include any liquid absorbent/absorbing material known in the art (e.g. cotton, a cotton blend, foam, a synthetic material, absorbent polymeric foam, a nanotechnology-based or -produced material, or any other moisture-absorbent material). The material may have a weight of 50 to 900 $g/m^2$, such as 180 to 300 $g/m^2$. For example, the absorbent component 112 may be made from an 80:20 blend of polyester:nylon fabric with a microfiber double terry knit. Other suitable materials include polypropylene, polyethylene, or any cellulose-based fabric and their blends including cotton, bamboo, etc.

In some embodiments, the absorbent layer 112 may be a 100% polyester double terry fabric. This material is approximately 90% air and so allows for a higher absorbent capacity, as moisture fills up the air gaps of the polyester terry fabric without significant expansion of the polyester fibres. This does not translate into significantly thicker absorbent pad 100.

In some embodiments, the absorbent layer 112 may be made from a blended fibre comprising two or more of superabsorbent polymer (SAP), hydrogel, and polyester, or at least part of the absorbent layer 112, such as the lower interface facing towards the barrier layer 120, may have been treated or integrated with SAP and/or hydrogel. In these embodiments, the use of these materials may result in increased liquid absorbent capacity, with a reduced thickness and weight for the absorbent pad 100, and in an improved dry feel on the upper interface of the wicking layer 114 that may be in contact with the user's skin, due to an increased affinity in the absorbent layer 112. The wicking layer 114 and/or absorbent layer 112 may optionally have anti-bacterial/anti-odour and moisture management properties.

The barrier layer 120 may be attached to the functional assembly 110 by laminating the barrier layer 120 to the absorbent layer 112. As mentioned above, in some embodiments, the functional assembly 110 may include a single unitary layer configured for both wicking and absorbent functions, and the barrier layer 120 may be laminated to the single unitary layer. The barrier layer 120 is leak-proof and may include any known wholly or partially liquid-blocking material. Preferably, the barrier layer 120 is breathable, so that liquid may not pass through it, but gases (including water vapour) can do so. For example, the barrier layer 120 may include one or more thermoplastic films and/or one or more thermoset films, where the thermoplastic or thermoset film is selected from one or more of the group consisting of polyurethane, polyester, polyolefin, and silicone. Particular examples of liquid impermeable materials include layers made from a liquid impermeable polymer or a thermoplastic polyurethane film. The barrier layer 120 may alternatively or additionally include or be made of liquid impermeable fabrics and/or fusible yarns.

In some embodiments, the barrier layer 120 may be a lightweight tightly knitted/woven fabric coated with hydrogel or treated with a hydrophobic finishes such as durable water repellents (e.g. DWR), or the barrier layer 120 may be a lightweight tightly knitted/woven fabric made using textile/SAP hybrid fibres. Alternatively, the barrier layer 120 may be a liquid-proof membrane present independently or laminated/attached to a textile material with adhesive bonding or other attachment methods including ultrasonic bonding or stitching. When used in a garment 200 comprising the absorbent pad 100, the barrier layer 120 may provide the advantage of being fully breathable in dry form, while providing an effective barrier material upon exposure to liquid. Furthermore, these materials may also enable the absorbent pad 100 to dry more quickly than the use of a liquid impermeable polymer such as a thermoplastic polyurethane film.

In some embodiments, the peripheral assembly 130 includes the liquid impermeable sealing element 132 that is attached to the peripheries of the functional assembly 110 and barrier layer 120. More specifically, the sealing element 132 is attached to the upper interface of the wicking layer 114 and the lower interface of the barrier layer 120. The sealing element 132 may include a single-sided adhesive tape and said tape may have a single layer or multiple layers where said multiple layers may have one or more functions, such as liquid barrier functions, elastic functions, etc. The adhesive side of the single-sided adhesive tape faces the functional assembly 110 and barrier layer 120. As shown in FIGS. 1B and 1C, the sealing element 132 has a C-fold or C-shaped arrangement that entirely encloses the peripheries of the functional assembly 110 and barrier layer 120. This arrangement forms a liquid impermeable barrier seal or cuff and advantageously reduces leakage of bodily fluids from the absorbent pad 100 onto the garment 200. This arrangement also results in a durable garment 200 that may be washed and reused multiple times.

In some embodiments, the sealing element 132 is liquid impermeable and optionally elastic but does not have adhesive properties. The sealing element 132 may be bonded to the peripheries of the functional assembly 110 and barrier layer 120 by suitable bonding means, such as adhesive or ultrasonic bonding. It will be appreciated that the sealing element 132 may be bonded to some or all layers of the absorbent pad 100.

In some embodiments, the functional assembly 110 is attached to the barrier layer 120 by stitching at their respective peripheries. Similarly, the wicking layer 114, absorbent layer 112, and barrier layer 120 can be stitched together at their peripheries. The sealing element 132 is arranged such that it overlaps the stitches at the peripheries, which could potentially form conduits for liquid to pass through, in order to maintain the liquid impermeability of the absorbent pad 100.

In some embodiments, the barrier layer 120 and sealing element 132 may be a continuous piece of liquid impermeable material. This continuous material would be bonded to the periphery of the functional assembly 110 in a similar manner to the embodiments where the barrier layer 120 and sealing element 132 are separate pieces of material bonded together.

In some embodiments as shown in FIG. 3A, the functional assembly includes a top layer 140 attached to the wicking layer 114 and arranged to face towards the user's skin when in use. For example, the top layer 140 is attached to the wicking layer 114 by an adhesive film 102. Alternatively, the top layer 140 is knitted to the wicking layer 114. The top layer 140 may include one or more of a hydrophilic material, a hydrophobic material, and a hydrochromic material. Various aspects of the hydrophilic material, hydrophobic material, and hydrochromic material described above for the wicking layer 114 may apply equally to the top layer 140, and are not further elaborated for purpose of brevity.

In some embodiments further as shown in FIGS. 3B and 3C, the top layer 140 includes an array of openings 142 for liquid transfer from the user's skin to the wicking layer 114. For example, the top layer 140 includes or is a mesh layer that is preferably in direct contact with the user's skin when in use. The mesh layer has an array of openings 142 for liquid transfer from the user's skin to the wicking layer 114. Some exemplary shapes and sizes of the mesh layer are shown in FIGS. 3B and 3C, but it will be appreciated that the mesh layer can be formed in other shapes and sizes, similar to the different shapes and sizes of the liquid flow channels 144 in FIGS. 4A to 4D. Further, the mesh layer may be formed using various manufacturing methods, such as moulding, dye cutting, laser cutting, printing, stitching, knitting, gluing, embossing, debossing, or extruding.

The mesh layer preferably includes or is made of a hydrophobic material. For example, the mesh layer may be treated to have hydrophobic properties, and optionally stain-free/stain-release/stain-resistant properties, and may be used to enhance aesthetics or introduce a visual effect to the absorbent pad 100. When the mesh layer is hydrophobic, it enables the bodily fluids to pass through the openings 142 so that its upper interface stays dry. When the mesh layer is present in addition to the wicking layer 114, the mesh layer may create an additional wicking window to improve rewetting.

Figure 4A:
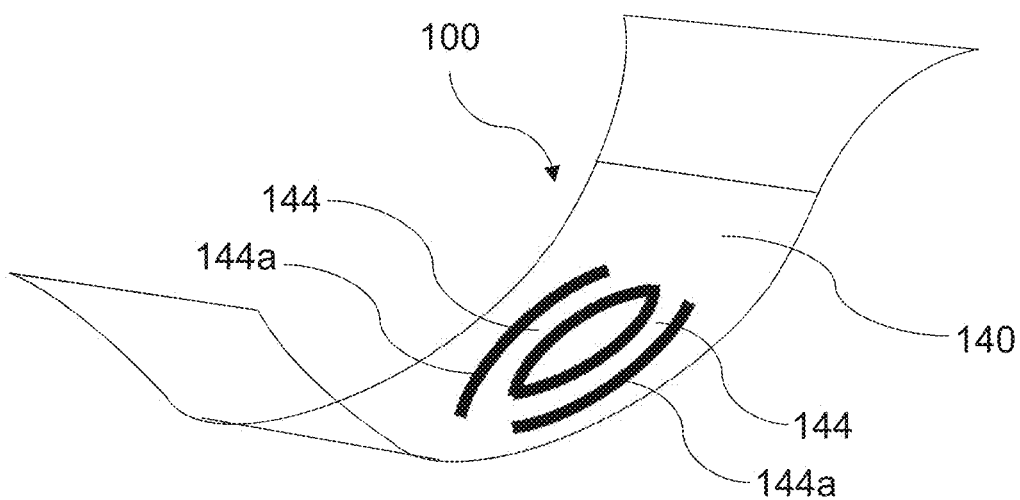
FIGS. 4A to 4D are various illustrations of liquid flow channels of the absorbent pad.

In some embodiments as shown in FIG. 4A, the top layer 140 may include an array of channels 144 for guiding liquid flow, and the channels 144 may include a hydrophobic material 144a. For example, the top layer 140 include fabric structures such as quilting and origami structures to form the channels 144. For example, the hydrophobic material 144a includes a cured polymeric material that is patterned to form the channels 144. The cured polymer material may be thermoset and/or a thermoplastic polymer, such as a silicone polymer.

The channels 144 may be formed using various manufacturing methods, such as moulding, dye cutting, laser cutting, printing, stitching, knitting, gluing, embossing, debossing, or extruding. For example, the channels 144 may be moulded using compression moulding or injection moulding. In the case of injection moulding, the other layer(s), such as the wicking layer 114, may be placed in the mould first, then the liquid foam material, such as the polymer material mentioned above, may be injected under pressure into the mould cavity, which fills and solidifies rapidly within the cavity into the final moulded shape.

The cured polymeric material may result in an embossed configuration that may result in more effective channeling of the liquid across the entire surface area. In addition, this embossing may also assist in shaping of the absorbent pad 100. This shaping may help to improve the fit of the absorbent pad 100 to the body part to which it is intended for use with, and ensures that the garment 200 stays in place to promote better functionality of the absorbent pad 100. Additionally or alternatively, the cured polymeric material may be laid in a debossed manner. This debossed configuration has the same properties as discussed above for the embossed configuration. As will be appreciated, a combination of embossed and debossed patterns may be used herein to help maximise the distribution of the bodily fluids across the entire surface and/or to improve the conformation/fit of the absorbent pad 100 to the body part to which it is intended to fit to in use.

Figure 4B:
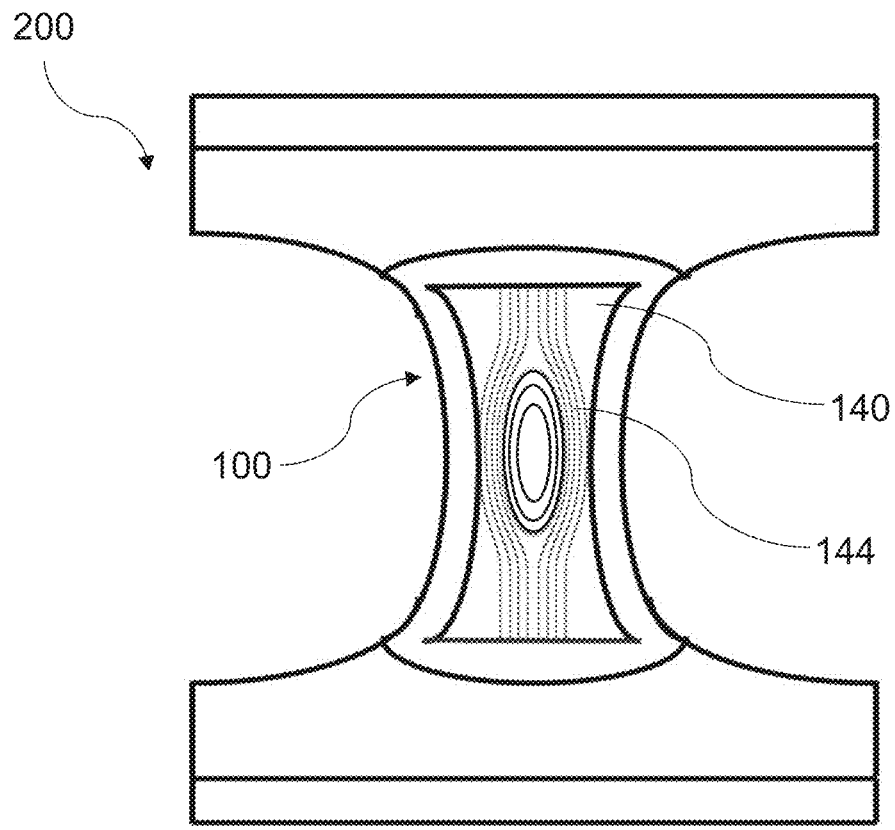
Figure 4C:
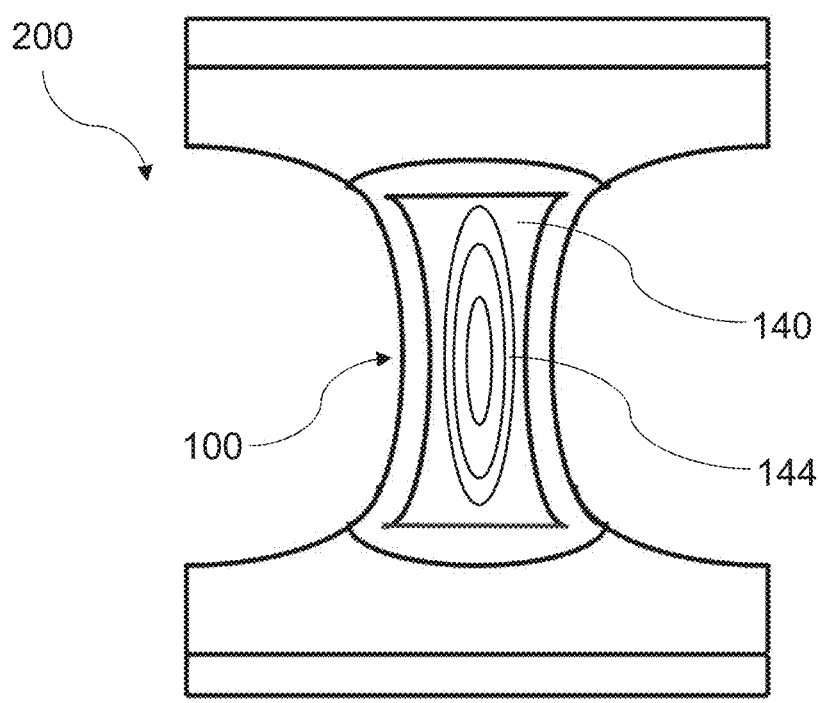
Figure 4D:
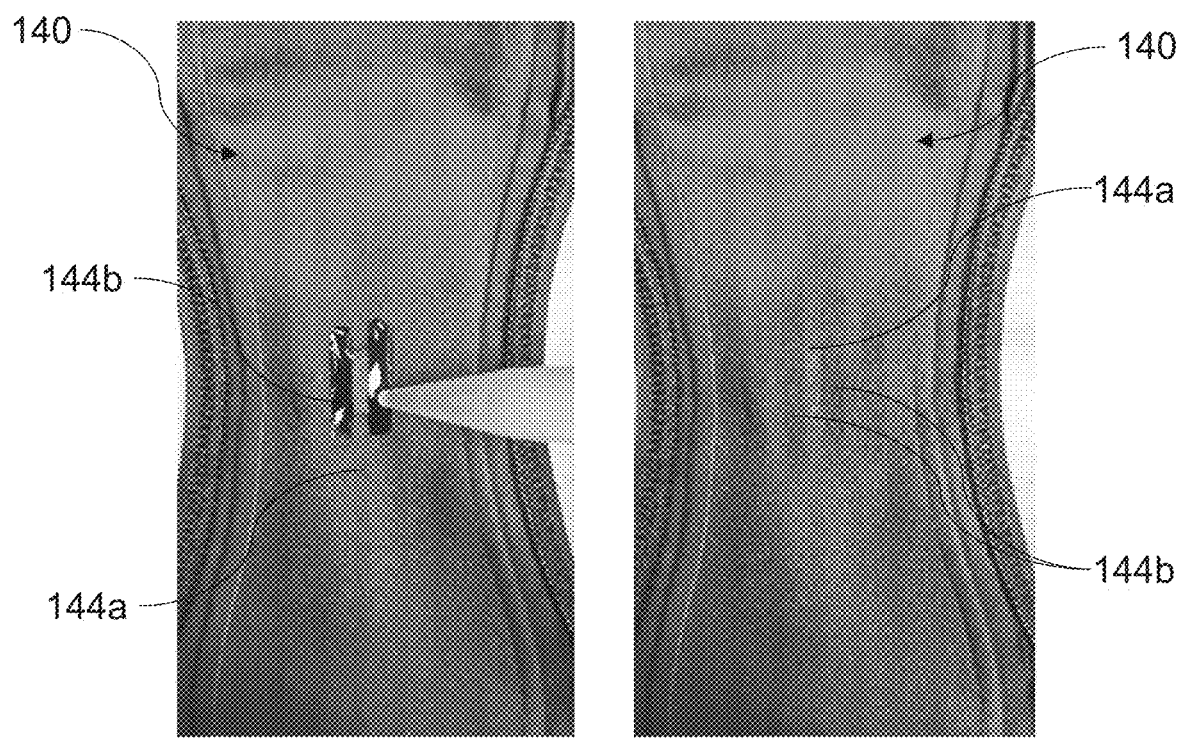

The channels 144 may be arranged in various ways to guide the liquid flow. Some examples of the array of channels 144 are shown in FIGS. 4A to 4C. FIG. 4D shows another example wherein the channels 144 are arranged as a linear array of hydrophobic material 144a and hydrophilic material 144b. For example, the top layer 140 is made of the hydrophilic material 144b, and the hydrophobic material 144a is added as alternating lines on top of the hydrophilic material 144b. Alternatively, the top layer 140 is made of the hydrophobic material 144a, and the hydrophilic material 144b is added as alternating lines on top of the hydrophobic material 144a. The alternating lines of hydrophobic material 144a or hydrophilic material 144b may be added using various means. For example, the alternating lines of hydrophobic material 144a or hydrophilic material 144b are printed on the top layer 140. For example, the alternating lines of hydrophobic material 144a or hydrophilic material 144b are yarns that are knitted or woven into the top layer 140. When in use, the hydrophobic material 144a repels water towards the adjacent hydrophilic material 144b which guide the water to flow along the hydrophilic material 144b and thereby improve liquid transport across the top layer 140.

In some embodiments, the absorbent pad 100 excludes the top layer 140, and the wicking layer 114 is the outermost layer facing the user's skin. The wicking layer 114 may include similarly-formed channels like the channels 144 of the top layer 140 that are arranged to guide liquid flow. The wicking layer 114 may function like a mesh layer. It will be appreciated that various aspects of the top layer 140 described above may apply equally to the wicking layer 114 and vice versa. For example, the top layer 140 may have anti-odour/anti-bacterial properties.

In some embodiments, the absorbent layer 112 and/or the wicking layer 114 may include a foam material. The absorbent pad 100 may optionally be moulded. The foam material may be provided in the final product of the absorbent pad 100 either in a moulded form or in an unmoulded form, depending on the desired final shape of the product. For example, the foam material may include thermosetting and/or thermoplastic polymers, such as a foam material that comprises from 50 to 100 wt % of polyurethane). Other suitable foam materials may include, but are not limited to, polyethylene foams, polypropylene foams, polyurethane foams, ethylene-vinyl acetate (EVA) foams, non-woven foams, and combinations thereof. Further examples of suitable foam materials include a mixture of the foams mentioned previously with a material like elastane.

In embodiments where the foam material is to be moulded, the foam material may first be provided in a flat state and affixed to the other layers or components of the absorbent pad 100 to form a stack, such as a composite of the wicking layer 114, absorbent layer 112, and barrier layer 120. This stack may then be subjected to moulding to provide the desired 3D shape. This moulding may be by thermal moulding, injection moulding, or any other suitable methods. In the case of injection moulding, the other layer (s), such as the wicking layer 114, may be placed in the mould first, then the liquid foam material, such as thermosetting and/or thermoplastic polymers, may be injected under pressure into the mould cavity, which fills and solidifies rapidly within the cavity into the final moulded shape.

Alternatively or additionally, the absorbent layer 112 and/or the wicking layer 114 may be shaped using the suitable fabric materials and/or apparel constructions/techniques instead of or in addition to the foam material. For example, the fabric material may be a spacer fabric. For example, various techniques can be used on fabric material to form the desired shapes, such as moulding, sewing, stitching, and knitting. For example, darts may be sewn on the absorbent layer 112/wicking layer 114 to form the desired shape. For example, the fabric material, such terry fabric, may be knitted into the desired 3D shapes using suitable knitting methods such as flat knitting or circular knitting.

As will be appreciated, the foam material or fabric materials like spacer fabric or terry fabric becomes unified to form the absorbent layer 112/wicking layer 114 in the desired shapes. For example, the liquid foam material takes the shape of the mould and solidifies. Shaping of the absorbent layer 112 and wicking layer 114, and more generally the functional assembly 110, may offer a more organic fit that adheres to the body's natural curvature, allowing custom-made foam shapes that achieve better aesthetics and comfort to the eventual wearer. For example, the functional assembly 110 and resultant absorbent pad 100 may be shaped like a 3D pouch for male undergarments to increase comfort for male users.

Figure 5A:
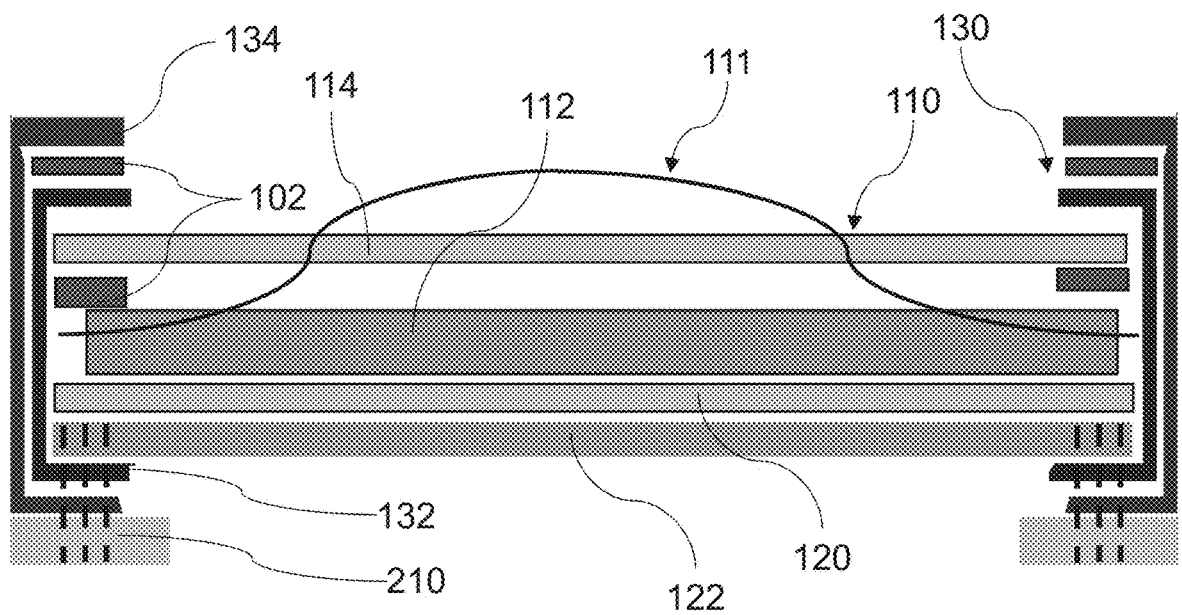
FIGS. 5A to 5C are various illustrations of a functional assembly of the absorbent pad.
Figure 5B:
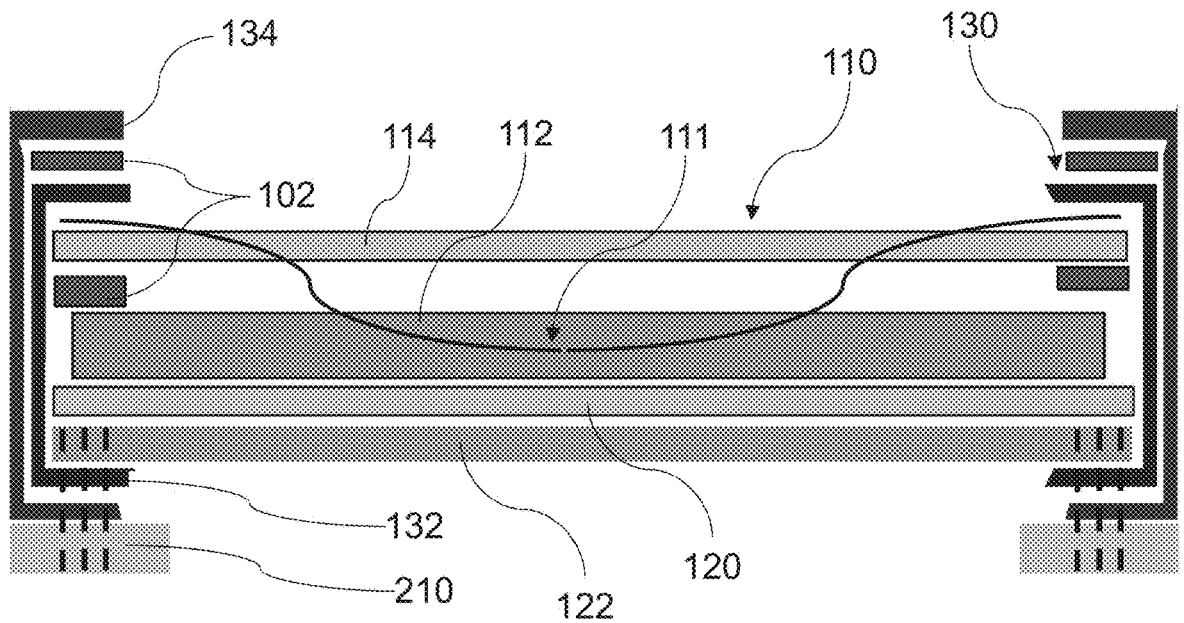

In some embodiments, the functional assembly 110 may be in various shapes instead of a planar structure. For example, the absorbent pad 100 is shaped such that the functional assembly 110 has a deformed portion 111. The deformed portion 111 may be a raised portion as shown in FIG. 5A which creates a debossed configuration for the functional assembly 110, or a recessed portion as shown in FIG. 5B which creates an embossed configuration for the functional assembly 110. The functional assembly 110 may be moulded to form the deformed portion 111. Alternatively or additionally, the functional assembly 110 may be formed with suitable knit structures and/or materials, such as foam and fabric materials like spacer or terry fabrics, or by various apparel construction techniques such as introduction of darts, to form the deformed portion 111. As shown in FIGS. 5A and 5B, the absorbent pad 100 may optionally include a fabric layer 122 attached to the barrier layer 120 below the barrier layer 120.

Figure 5C:
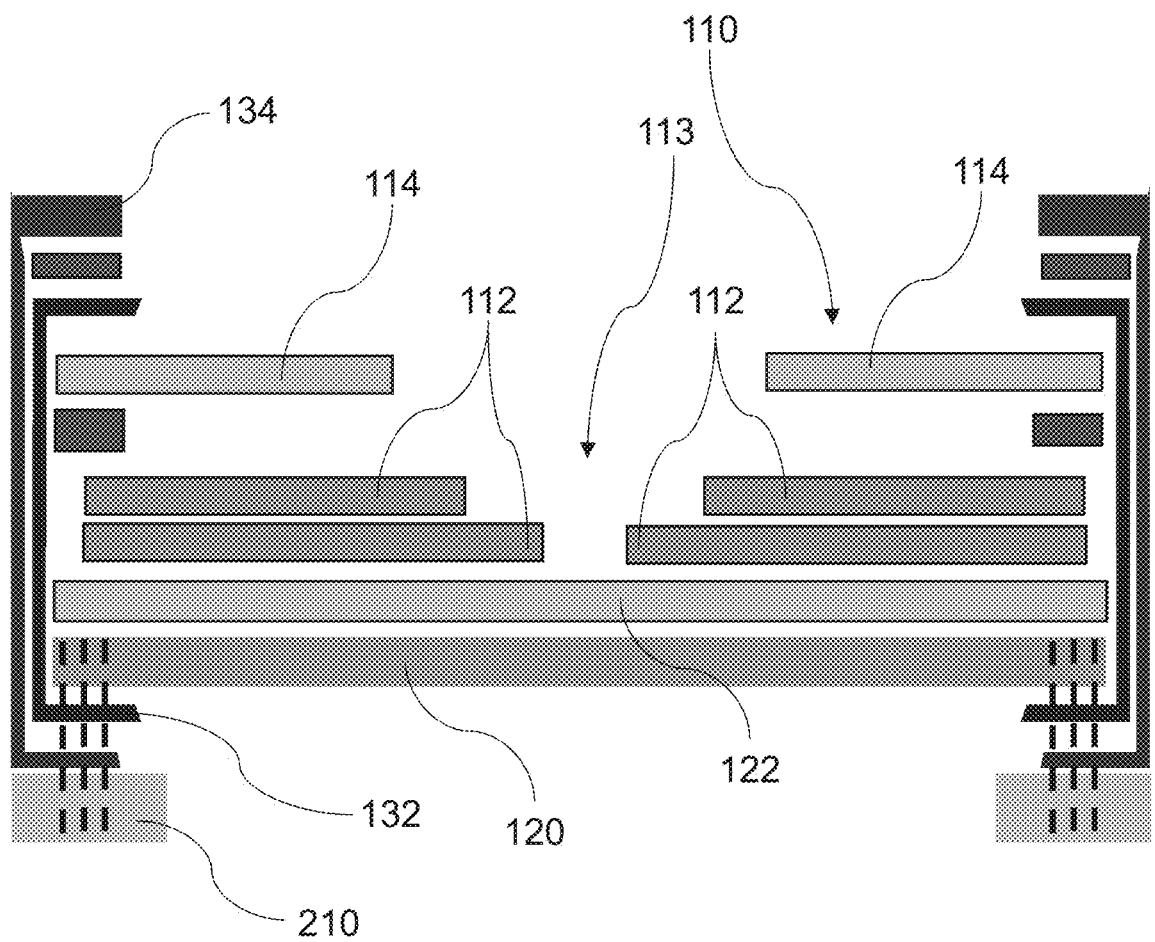

In some embodiments as shown in FIG. 5C, the functional assembly 110 may be shaped such that it has a recessed centre portion 113. In particular, the middle parts of the absorbent layer 112 and wicking layer 114 are removed to form the recessed centre portion 113, thereby creating the debossed configuration for the functional assembly 110. Alternatively or additionally, a smaller absorbent layer may be added on top of the centre of the absorbent layer 112 to create the embossed configuration.

A combination of embossed and debossed configurations, such as from the deformed portion 111 of FIG. 5B and the recessed centre portion 113 of FIG. 5C, increase the volume for absorption and make the absorbent pad 100 more ergonomically fitting for the user around the crotch/genital area to secure leakages. Particularly, the increased volume of the functional assembly 110 makes the absorbent pad 100 and the garment 200 comprising the absorbent pad 100 more suitable for use for or as men's undergarments or male urinary incontinence garments.

Figure 6A:
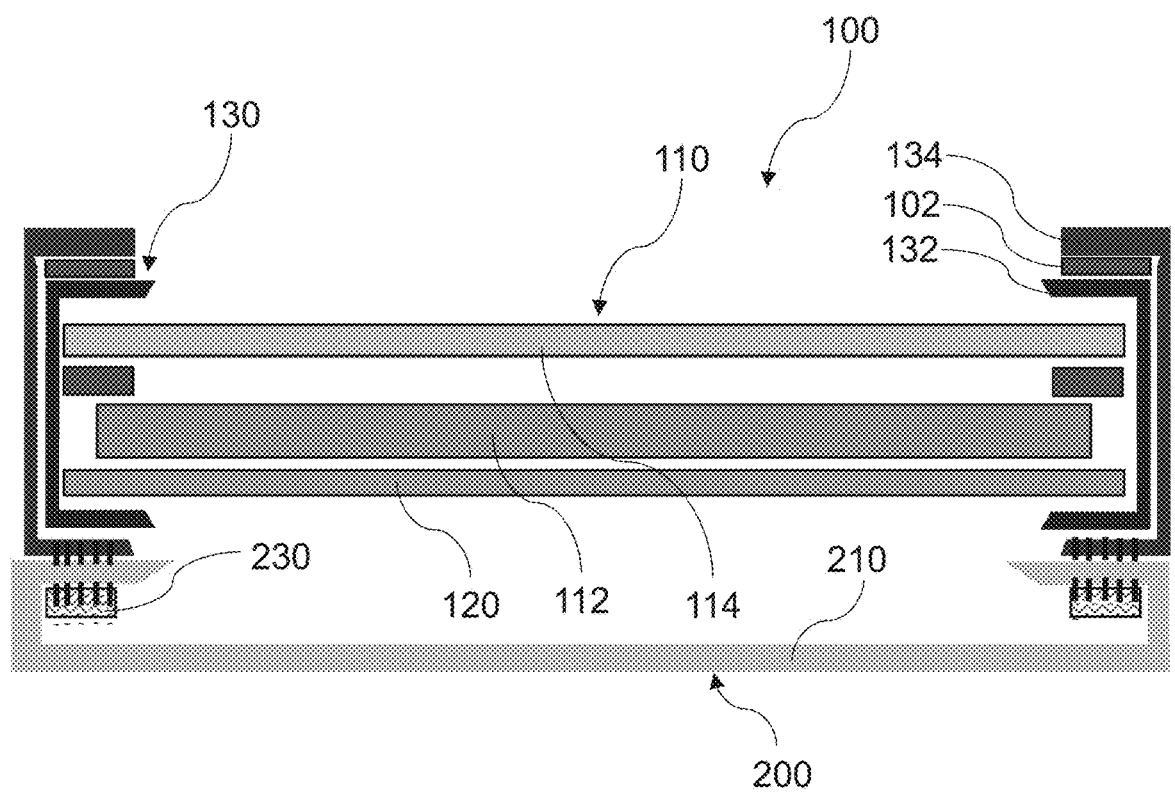
FIGS. 6A and 6B are various illustrations of a peripheral assembly of the absorbent pad.
Figure 6B:
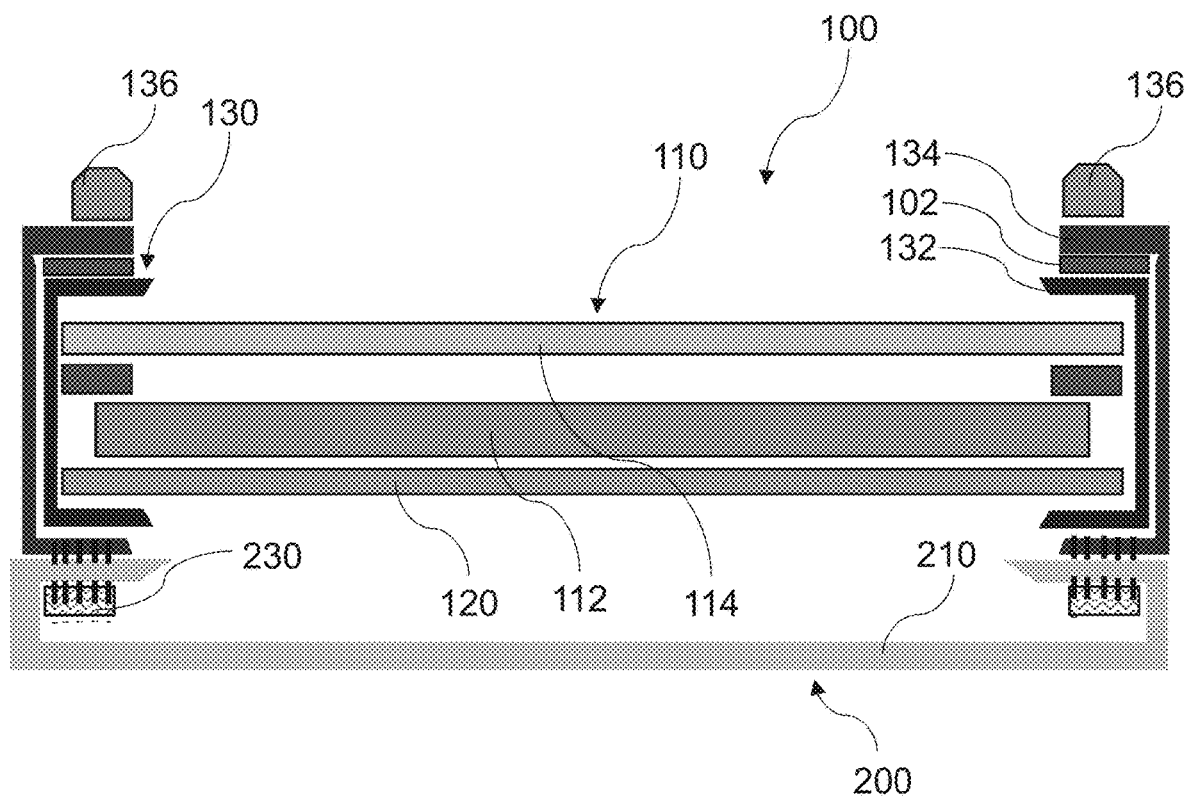

In many embodiments such as shown in FIGS. 3A and 5A to 5C, the peripheral assembly 130 includes a pad attaching element 134 attached to the periphery of the functional assembly 110. The pad attaching element 134 may include one or more of a hydrophilic material, a hydrophobic material, and a hydrochromic material. Further as shown in FIGS. 6A and 6B, the pad attaching element 134 may be arranged for stitching the absorbent pad 100 to an inside of the garment 200. For example, one part of the pad attaching element 134 is attached to the sealing element 132 by an adhesive film 102, and another part of the pad attaching element 134 is stitched or otherwise attached to the fabric body 210 of the garment 200.

As shown in FIG. 6A, the pad attaching element 134 may have a C-fold or C-shaped arrangement, like that of the sealing element 132, that entirely covers the sealing element 132. The pad attaching element 134 may be formed of a suitable material that is preferably liquid impermeable. For example, the pad attaching element 134 may be formed of the same, similar, or different fabric or textile material as that of the fabric body 210. For example, the pad attaching element 134 comprises a hydrophobic material such as a durable water repellent or a silicone material. The pad attaching element 134 may be treated with the durable water repellent that forms a coating on the pad attaching element 134. For example, the pad attaching element 134 includes a silicone lining or extrusion thereon. In some embodiments as shown in FIG. 6B, the pad attaching element 134 forms a liquid impermeable ridge 136 on the periphery of the functional assembly 110. This liquid impermeable ridge 136 facilitates channeling of liquid to the functional assembly 110 and reduces overflow from the peripheries of the functional assembly 110.

Figure 7A:
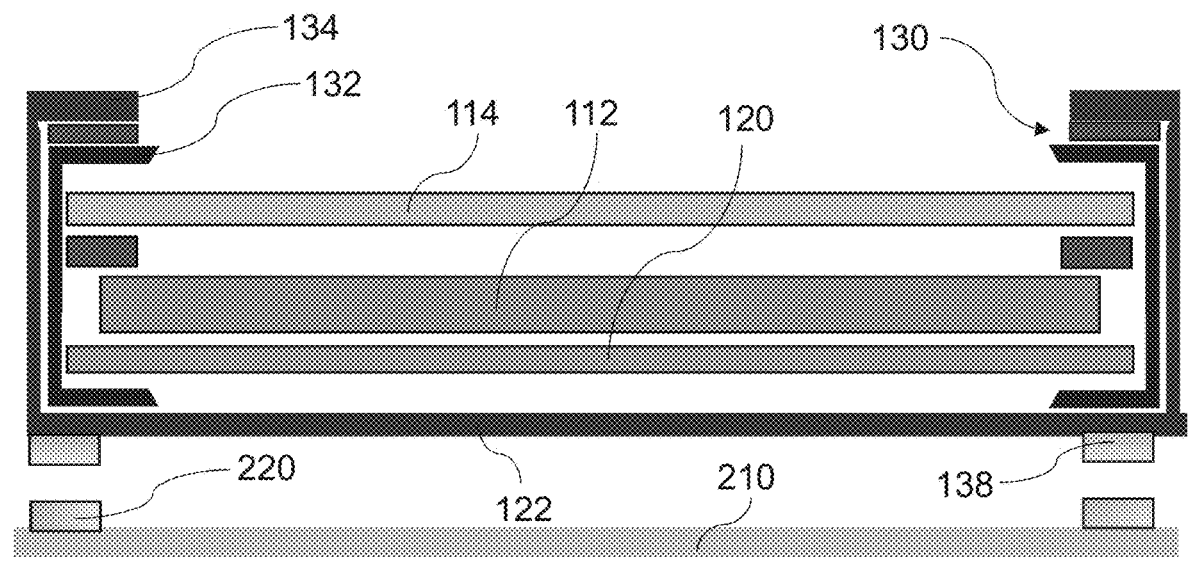
FIGS. 7A and 7B are various illustrations of the absorbent pad being fastened to the garment.
Figure 7B:
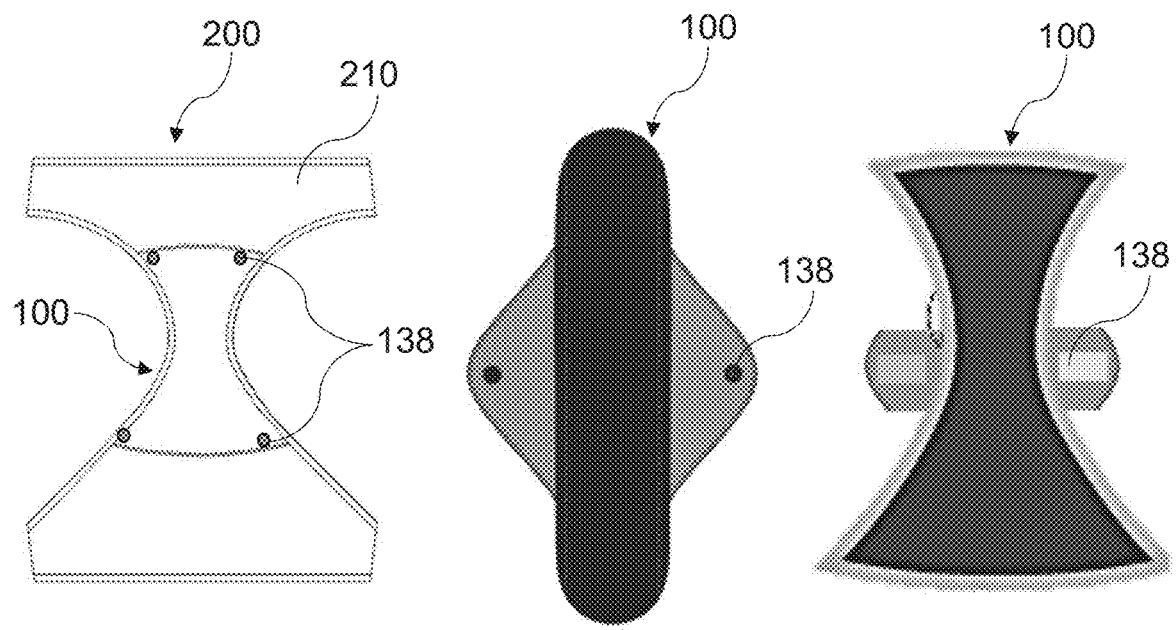

In some embodiments as shown in FIGS. 7A and 7B, the peripheral assembly 130 includes a plurality of fasteners 138 attached to the pad attaching element 134. For example, the absorbent pad 100 may include the fabric layer 122 that extends below and covers the barrier layer 120. Further, the fabric layer 122 may be continuous with the pad attaching element 134, such as formed from the same fabric material. The fasteners 138 are configured for fastening the absorbent pad 100 to the garment 200. More specifically, the fasteners 138 are configured for engaging with corresponding fasteners 220 of the garment 200, wherein the fasteners 220 may be located on the inner side and/or outer side of the fabric body 210. The fasteners 138,220 may include snap buttons and/or touch fasteners.

As described above, the absorbent pad 100 according to any of the embodiments described herein can be attached to a garment 200. Various embodiments of the present disclosure describe a garment 200 comprising the fabric body 210 and the absorbent pad 100 attached to the fabric body 210. The absorbent pad 100 may be in any suitable form and may be used for any suitable use within a garment 200. The absorbent pad 100 may be used independently on its own, or integrated with the garment 200. For example, the absorbent pad 100 is permanently attached to the fabric body 210 of the garment 200. Examples of such garments 200 may include leggings, panties, boxers, hipsters, etc. In some embodiments, the garments 200 may be associated with sanitary care. In some embodiments, the garments 200 may be associated with exercise clothing, may be for assisting users who may suffer from hyperhidrosis, or may be for assisting users who may need targeted absorption of bodily fluids during the course of the day and/or during exercise. The garments 200 may be associated with use as underwear or overwear. Further examples of garments 200 include, but are not limited to, absorbent underwear, leakproof swimwear, baby diapers, swim diapers, absorbent nursing garments, bras, shorts, swimwear, activewear, leggings, and tights, or any other garment 200 that can incorporate an absorbent pad 100.

Preferably, the absorbent pad 100 is attached to an interior surface of the fabric body 210 and extends over at least an area of the user that is subject to bodily excretions. One or more absorbent pads 100 may form part of a garment 200, whether integral or removable. Any garment 200 that is intended to be in contact with a user's skin may be fitted with one or more absorbent pads 100. One or more absorbent pads 100 may be fitted to cover a small area of the garment 200, which will generally be an area subject to the production of bodily excretions, such as the crotch area, the underarm area, or the nipples of a pre- or post-partum female. Alternatively, the absorbent pads 100 may cover a major portion of the internal surface area of the garment 200, for example, the absorbent pads 100 in a pair of underpants may cover from 30% to 100% of the internal surface area of the garment 200. The level of internal surface area coverage of the absorbent pads 100 can be readily determined based upon the intended use and the desired level of comfort of the user.

The fabric body 210 may include one or more layers and each layer may include one or more fabric materials. Further, the fabric body 210 may include materials and/or is treated with one or more of thermal regulating agents, cooling agents, stain-resistant agents, anti-bacterial agents, odour-resistant agents, and hydrophobic agents. Preferably, the materials of the absorbent pad 100 and garment 200 allow the sorbent pad 100 and garment 200 to be washable and reusable to reduce environmental impact. For example, the absorbent pad 100 and garment 200 are able to withstand at least 15 (e.g. a minimum of 50 or 100) domestic machine wash and tumble dry cycles without compromising one or more of overall appearance, integrity of the components, liquid/moisture management properties, antimicrobial functionality, and anti-odour functionality. Further, the integrity of the absorbent pad 100 and garment 200 may be maintained for a minimum of 15 (e.g. a minimum of 50 or 100) wash and dry cycles. This ensures that the absorbent pad 100 will not leak during the lifetime of the garment 200. For example, the various materials of the absorbent pad 100 are chosen such that they remain chemically, thermally, and mechanically stable throughout the intended lifetime of the absorbent pad 100 and garment 200 while undergoing the intended wash and dry cycles.

In some embodiments, the garment 200 may include a waist opening and/or leg openings. Optionally, the waist opening and/or leg openings may include or may be made of a material to improve the grip of the garment 200 on the user's body. For example, the material includes nanoyarns or nano-fibre material, such as ultrafine polyester, exposed spandex fabrics, elastic with polyurethane or silicon lines, polyurethane/thermoplastic polyurethane tapes, neoprene materials or similar, that increase its surface area and frictional resistance and thereby improve gripping properties. In some embodiments such as shown in FIGS. 6A and 6B, the garment 200 includes one or more elastic bands 230 to provide flexibility/elasticity/stretchability to the user. For example, the elastic bands 230 may be lined on or attached to the fabric body 210, such as by adhesive or ultrasonic bonding. The elastic bands 230 allow the garment 200 to come in a small number of discrete sizes that are able to cater to a wide variety of users of various sizes. For example, the elastic bands 230 are arranged to surround the waist opening and/or leg openings of the garment 200.

FIGS. 8A to 8K show various ways of attaching the absorbent pad 100 to the garment 200, specifically attaching the pad attaching element 134 to the fabric body 210. The pad attaching element 134 is preferably liquid impermeable. For example, the pad attaching element 134 is made of a liquid impermeable material and/or treated with a hydrophobic or waterproofing agent. Further, the liquid impermeable barrier layer 120 may be part of the fabric body 210 and/or part of the absorbent pad 100. For example, the fabric body 210 may be made of or include a hydrophobic material or treated with a hydrophobic or waterproofing agent to achieve the liquid impermeability property.

The treatment applied to the pad attaching element 134 and fabric body 210, as well as any other component of the absorbent pad 100 and garment 200 that may require liquid impermeability, may be any suitable material that may result in a material having liquid impermeable properties. Examples of such materials include, but are not limited to, hydrophobic- and water-repellent finishes such as durable water repellent. Such finishes may include, but are not limited to wax-based repellents, silicone-base repellents, and fluorocarbon-based and non-fluorocarbon-based repellents. Alternatively or additionally, the treatment may include coating with a suitable material, which may include, but is not limited to an SAP/hydrogel coating or a thermoplastic and/or thermoset coating. The latter two coatings may be derived from polymers selected from one or more of the group consisting of polyurethane, polyester, polyolefin, and silicone polymers.

Figure 8A:
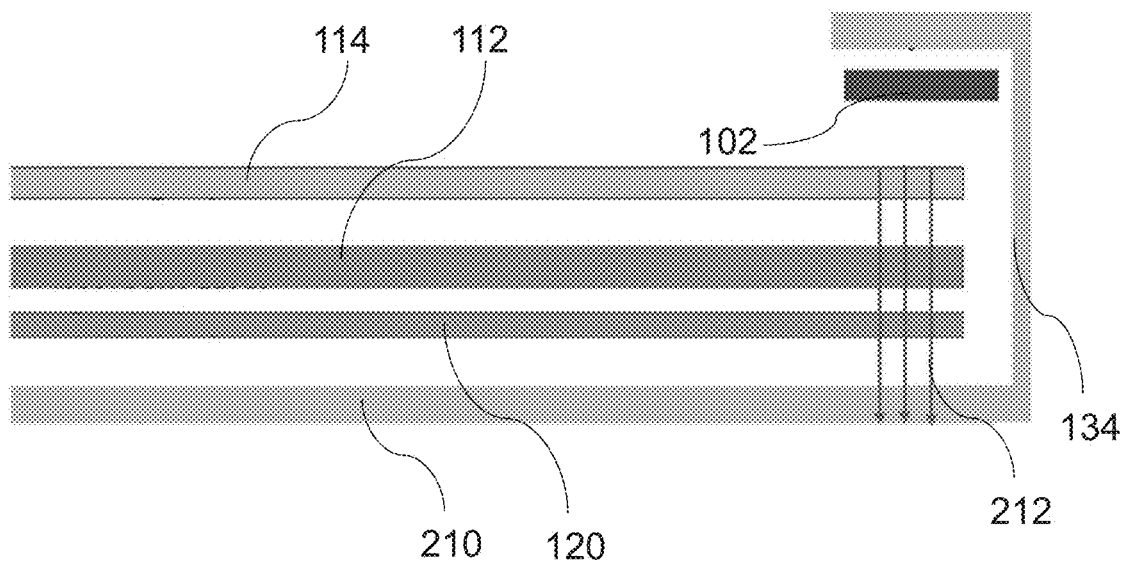
FIGS. 8A to 8K are various illustrations of attaching the absorbent pad to the garment.

In one embodiment as shown in FIG. 8A, the absorbent pad 100 including the functional assembly 110 and barrier layer 120 are stitched to the fabric body 210. The pad attaching element 134 is an extension of the fabric body 210 and is attached to the wicking layer 114 via an adhesive film 102. The fabric body 210 acts as a liquid impermeable barrier and the pad attaching element 134 is similarly liquid impermeable. For example, the fabric body 210 and pad attaching element 134 optionally include a liquid impermeable material or are treated with a hydrophobic material. The liquid impermeable pad attaching element 134 and fabric body 210 cooperatively cover the visible stitch lines 212 and seal the periphery of the absorbent pad 100 from side leakages.

Figure 8B:
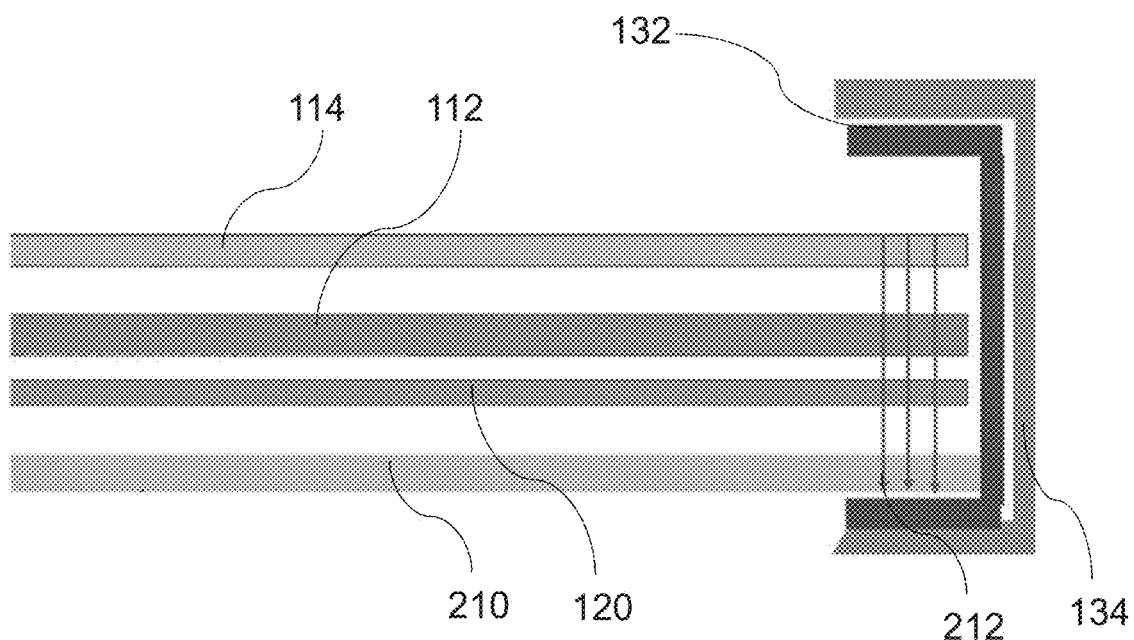

In one embodiment as shown in FIG. 8B, the absorbent pad 100 including the functional assembly 110 and barrier layer 120 are stitched to the fabric body 210. The liquid impermeable sealing element 132 is attached to the wicking layer 114 and fabric body 210. Additionally, the pad attaching element 134 is attached to the sealing element 132 to cover the sealing element 132. For example, the pad attaching element 134 is a separate piece of fabric material that may be optionally liquid impermeable or treated with a hydrophobic material. The sealing element 132 and pad attaching element 134 cooperatively cover the visible stitch lines 212 and seal the periphery of the absorbent pad 100 from side leakages.

Figure 8C:
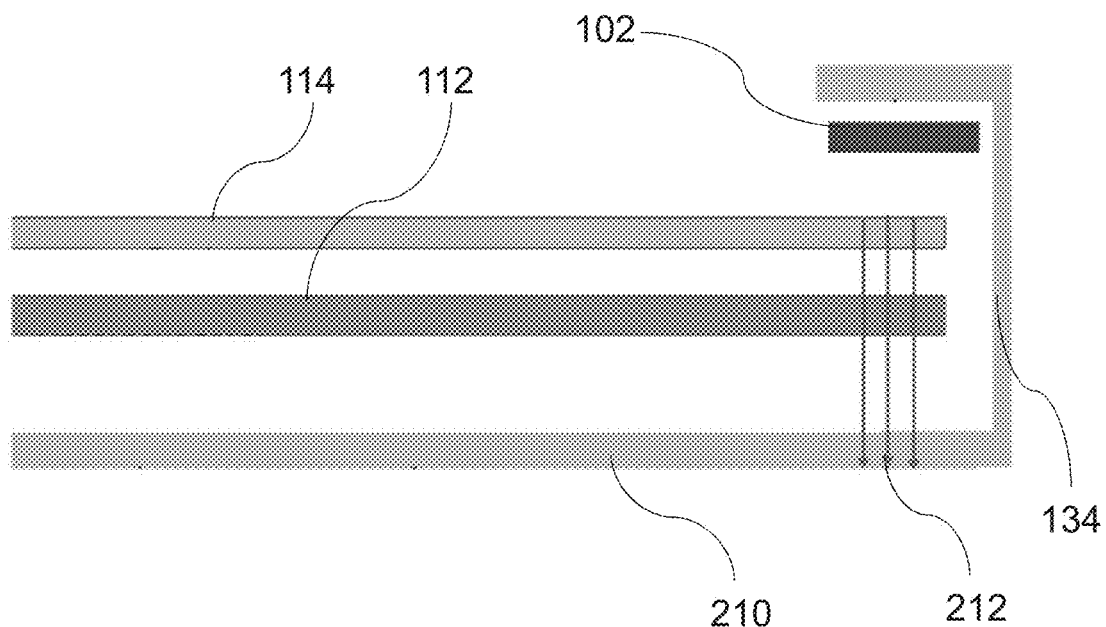

In one embodiment as shown in FIG. 8C, the absorbent pad 100 includes the functional assembly 110 but does not have the barrier layer 120. The functional assembly 110 including the absorbent layer 112 and wicking layer 114 are stitched to the fabric body 210. The pad attaching element 134 is an extension of the fabric body 210 and is attached to the wicking layer 114 via an adhesive film 102. The fabric body 210 and pad attaching element 134 include a liquid impermeable material or are treated with a hydrophobic material. The liquid impermeable fabric body 210 thus replaces the barrier layer 120 to prevent leakages from the bottom and side of the absorbent pad 100. The liquid impermeable pad attaching element 134 and fabric body 210 cooperatively cover the visible stitch lines 212 and seal the periphery of the absorbent pad 100 from side leakages.

Figure 8D:
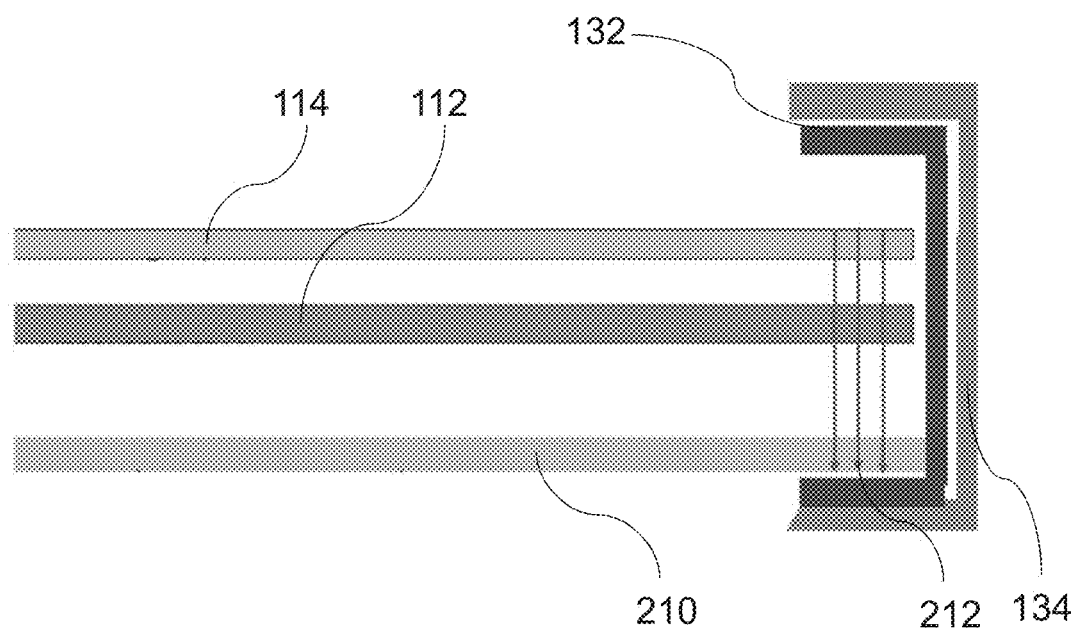

In one embodiment as shown in FIG. 8D, the absorbent pad 100 includes the functional assembly 110 but does not have the barrier layer 120. The functional assembly 110 including the absorbent layer 112 and wicking layer 114 are stitched to the fabric body 210. The liquid impermeable sealing element 132 is attached to the wicking layer 114 and fabric body 210. Additionally, the pad attaching element 134 is attached to the sealing element 132 to cover the sealing element 132. For example, the pad attaching element 134 is a separate piece of fabric material that may be liquid impermeable or treated with a hydrophobic material. The sealing element 132 and pad attaching element 134 cooperatively cover the visible stitch lines 212 and seal the periphery of the absorbent pad 100 from side leakages. Further, the fabric body 210 includes a liquid impermeable material or is treated with a hydrophobic material to replace the barrier layer 120 and prevent leakages from the bottom of the absorbent pad 100.

Figure 8E:
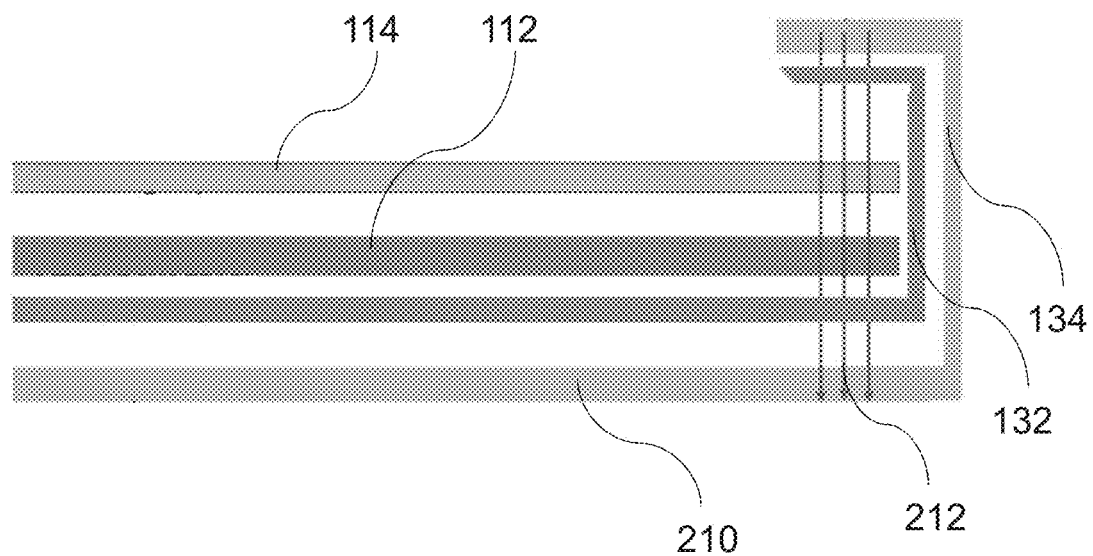

In one embodiment as shown in FIG. 8E, the absorbent pad 100 including the functional assembly 110 and barrier layer 120 are stitched to the fabric body 210. The sealing element 132 is an extension of the barrier layer 120 and is attached to the wicking layer 114. Additionally, the pad attaching element 134 is an extension of the fabric body 210 and is attached to the sealing element 132 to cover the sealing element 132. The pad attaching element 134 covers the visible stitch lines 212 and the sealing element 132 seals the periphery of the absorbent pad 100 from side leakages. The fabric body 210 and pad attaching element 134 may include a liquid impermeable material or may be treated with a hydrophobic material.

Figure 8F:
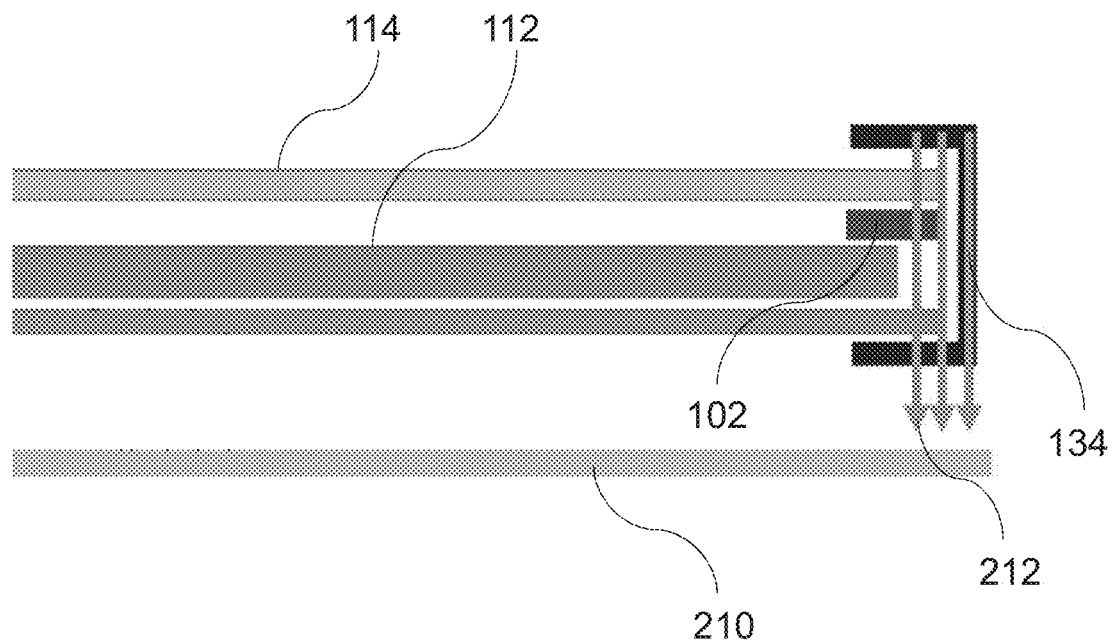

In one embodiment as shown in FIG. 8F, the absorbent pad 100 including the functional assembly 110 and barrier layer 120 are stitched to the fabric body 210, without stitching through the absorbent layer 112. The peripheries of the wicking layer 114 and absorbent layer 112 may be attached by an adhesive film 102. The sealing element 132 is attached to the wicking layer 114 and barrier layer 120 to seal the periphery of the absorbent pad 100 from side leakages. This embodiment avoids the use of a separate piece of fabric material to cover the visible stitch lines 212. The C-shaped sealing element 132 may include materials such as suitable liquid impermeable fabrics and fusible yarns, and may be attached using suitable means such as ultrasonic sealing/welding.

Figure 8G:
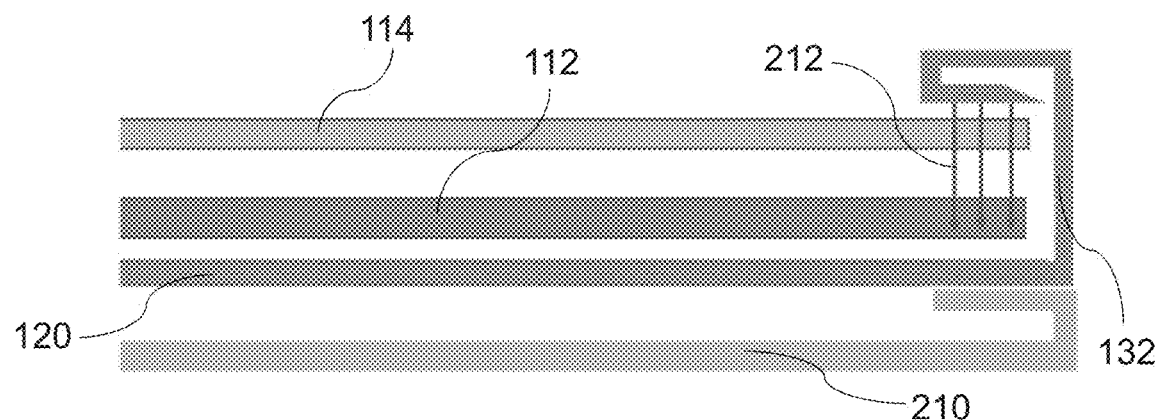

In one embodiment as shown in FIG. 8G, the absorbent pad 100 including the functional assembly 110 and barrier layer 120 are stitched to the fabric body 210. The sealing element 132 is an extension of the barrier layer 120 and is attached to the wicking layer 114 to seal the periphery of the absorbent pad 100 from side leakages. Additionally, the sealing element 132 is folded such that it covers the visible stitch lines 212.

Figure 8H:
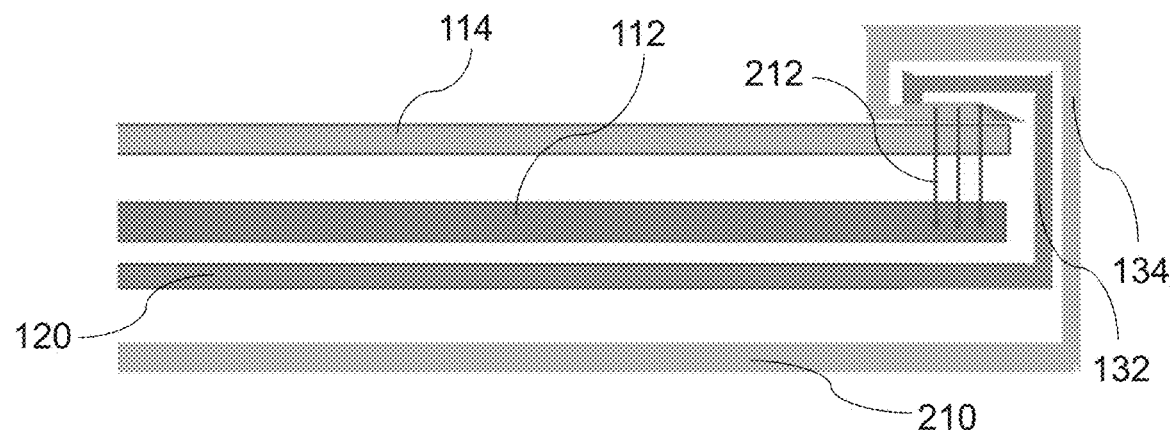

In one embodiment as shown in FIG. 8H, the absorbent pad 100 including the functional assembly 110 and barrier layer 120 are stitched to the fabric body 210. The sealing element 132 is an extension of the barrier layer 120 and is attached to the wicking layer 114. The pad attaching element 134 is an extension of the fabric body 210 and is attached to the sealing element 132 to cover the sealing element 132. The sealing element 132 and pad attaching element 134 cooperatively seal the periphery of the absorbent pad 100 from side leakages. Additionally, the sealing element 132 and pad attaching element 134 are folded such that they cover the visible stitch lines 212.

Figure 8I:
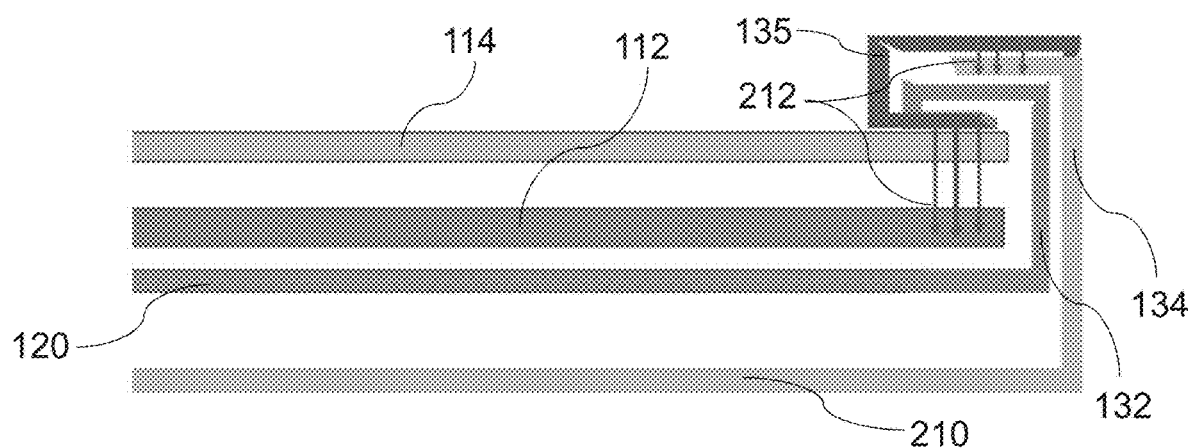

In one embodiment as shown in FIG. 8I, the absorbent pad 100 including the functional assembly 110 and barrier layer 120 are stitched to the fabric body 210. The sealing element 132 is an extension of the barrier layer 120 and is attached to the wicking layer 114. The pad attaching element 134 is an extension of the fabric body 210 and is attached to the sealing element 132 to cover the sealing element 132. The sealing element 132 and pad attaching element 134 cooperatively seal the periphery of the absorbent pad 100 from side leakages. Further, the peripheral assembly 130 includes a second pad attaching element 135 attached, such as by stitching or bonding with an adhesive, to the wicking layer 114 and the pad attaching element 134. Additionally, the sealing element 132, pad attaching element 134, and second pad attaching element 135 are folded such that they cover the visible stitch lines 212. As used in various embodiments herein, the second pad attaching element 135 may include one or more of a hydrophilic material, a hydrophobic material, and a hydrochromic material. For example, the second pad attaching element 135 is a separate piece of fabric material that may be liquid impermeable or treated with a hydrophobic material.

Figure 8J:
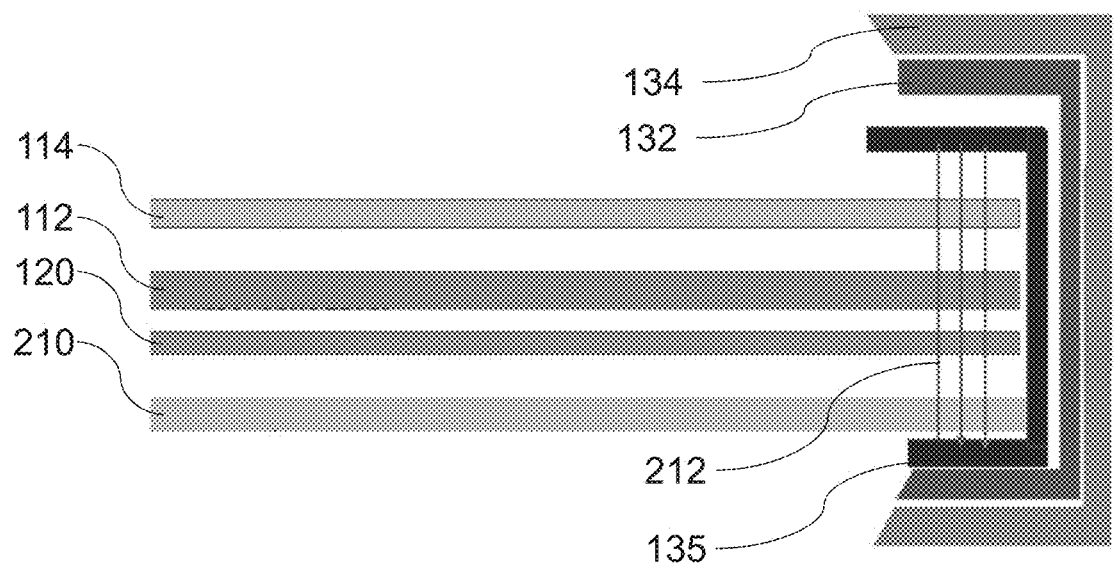

In one embodiment as shown in FIG. 8J, the absorbent pad 100 including the functional assembly 110 and barrier layer 120 are stitched to the fabric body 210. The peripheral assembly 130 includes a second pad attaching element 135 attached, such as by stitching or bonding with an adhesive, to the wicking layer 114 and fabric body 210. Additionally, the sealing element 132 is attached to the second pad attaching element 135 to cover the second pad attaching element 135. Further additionally, the pad attaching element 134 is attached to the sealing element 132 to cover the sealing element 132. For example, the pad attaching element 134 and second pad attaching element 135 are separate pieces of fabric material that may be liquid impermeable or treated with a hydrophobic material. The sealing element 132, pad attaching element 134, and second pad attaching element 135 cooperatively cover the visible stitch lines 212 and seal the periphery of the absorbent pad 100 from side leakages.

Figure 8K:
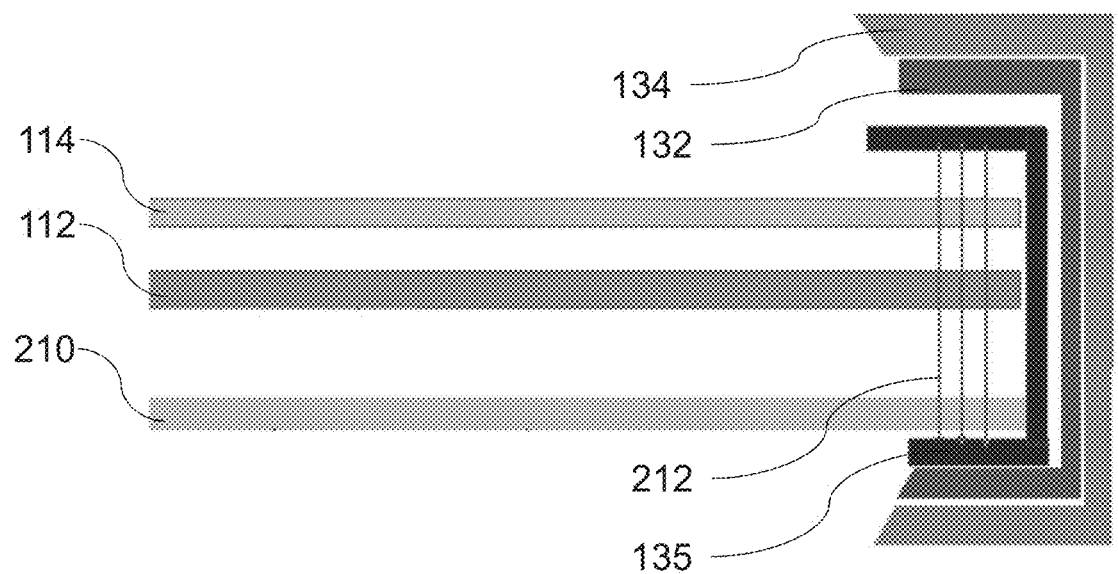

In one embodiment as shown in FIG. 8K, the absorbent pad 100 includes the functional assembly 110 but does not have the barrier layer 120. The functional assembly 110 including the absorbent layer 112 and wicking layer 114 are stitched to the fabric body 210. The peripheral assembly 130 includes a second pad attaching element 135 attached, such as by stitching or bonding with an adhesive, to the wicking layer 114 and fabric body 210. Additionally, the sealing element 132 is attached to the second pad attaching element 135 to cover the second pad attaching element 135. Further additionally, the pad attaching element 134 is attached to the sealing element 132 to cover the sealing element 132. For example, the pad attaching element 134 and second pad attaching element 135 are separate pieces of fabric material that may be liquid impermeable or treated with a hydrophobic material. The sealing element 132, pad attaching element 134, and second pad attaching element 135 cooperatively cover the visible stitch lines 212 and seal the periphery of the absorbent pad 100 from side leakages. Further, the fabric body 210 includes a liquid impermeable material or is treated with a hydrophobic material to replace the barrier layer 120 and prevent leakages from the bottom of the absorbent pad 100.

Figure 9A:
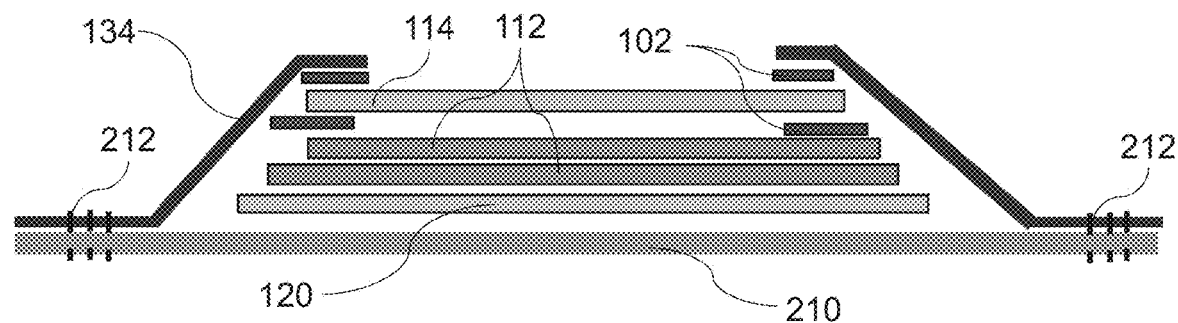
FIGS. 9A to 9F are various illustrations of stitching the absorbent pad to the garment.
Figure 9B:
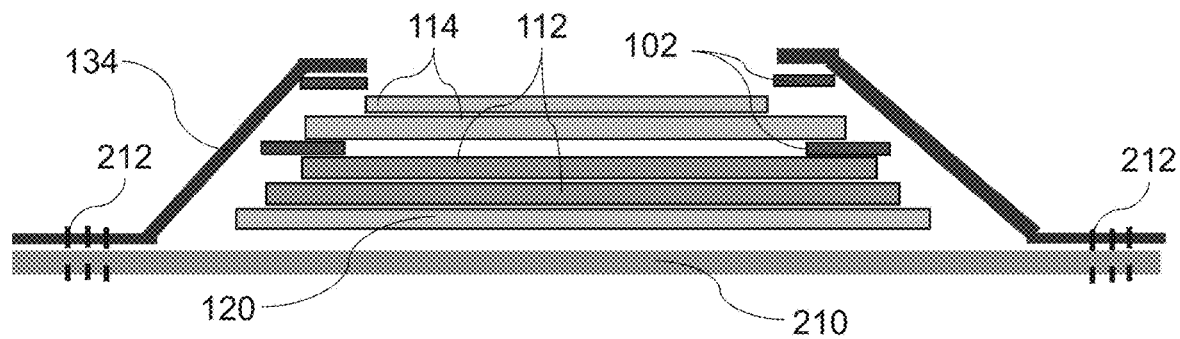

In some embodiments as shown in FIGS. 9A and 9B, the absorbent pad 100, which may include or exclude the barrier layer 120, is attached to the fabric body 210. More specifically, the peripheral assembly 130 includes the pad attaching element 134 that is bonded to the wicking layer 114 via an adhesive film 102 and stitched to the fabric body 210. For example, the pad attaching element 134 is a separate piece of fabric material that may be liquid impermeable or treated with a hydrophobic material. The absorbent layer 112 and wicking layer 114 may each be divided into respective upper and lower wicking layers, such as to create debossed/embossed effects if required.

In some embodiments, the barrier layer 120 is extended further along the fabric body 210, such as until the leg openings of the garment 200. For example, the barrier layer 120 and the fabric body 210 have approximately the same size. The pad attaching element 134 may be bonded to the barrier layer 120 via an adhesive film 102, or stitched to the barrier layer 120 and fabric body 210. The pad attaching element 134 is preferably hydrophobic to improve the liquid sealing.

Figure 9C:
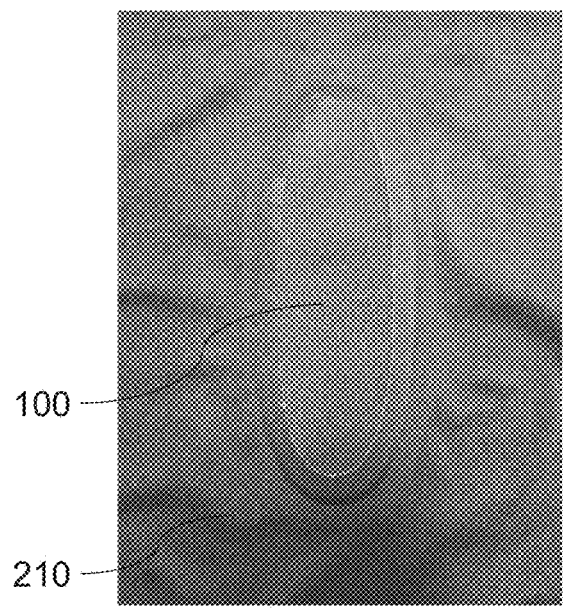
Figure 9D:
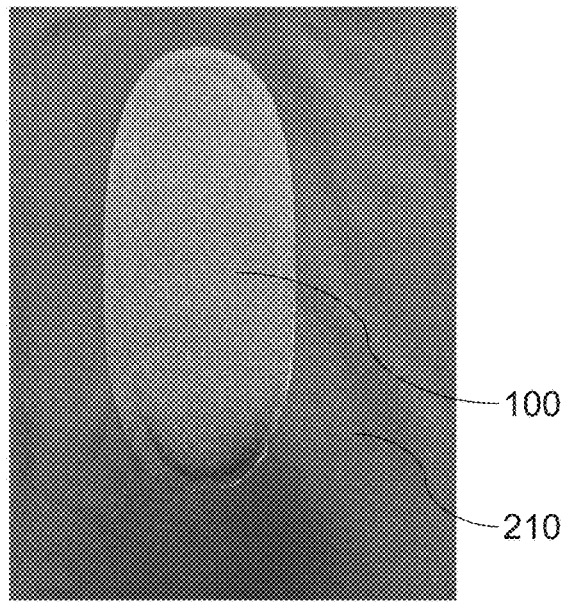
Figure 9E:
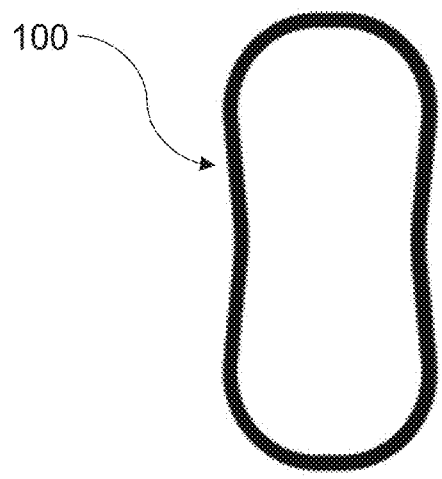
Figure 9F:
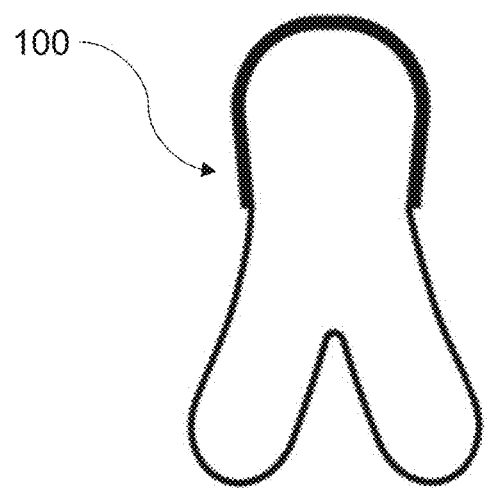

As shown in FIGS. 9C and 9D, this way of attaching the absorbent pad 100 to the fabric body 210 achieves an island shape that is more aesthetically appealing. The island may be in various shapes, such as a bean shape in FIGS. 9C and 9D showing the top side and bottom side, respectively, a dumbbell shape as shown in FIG. 9E, and a humanoid shape as shown in FIG. 9F.

Figure 10A:
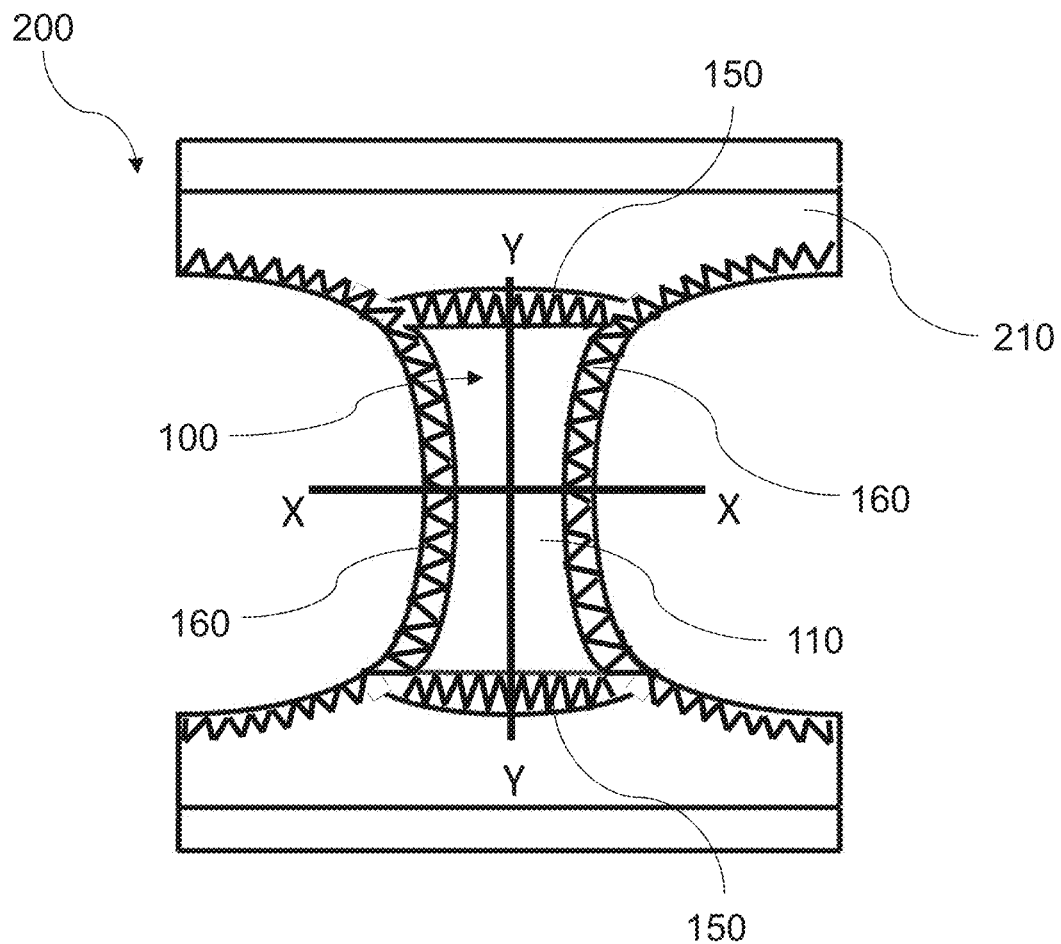
FIGS. 10A to 10D are various illustrations of the peripheral assembly having different subassemblies.

In some embodiments as shown in FIG. 10A to 10D, the peripheral assembly 130 includes a first peripheral subassembly 150 and a second peripheral subassembly 160. The first peripheral subassembly 150 is arranged at the front and rear of the absorbent pad 100 (extending between the left and right edges of the absorbent pad 100). The second peripheral subassembly 160 is arranged at the left and right of the absorbent pad 100 (extending between the front and rear edges of the absorbent pad 100). Notably, when the garment 200 is worn on the user, the first peripheral subassemblies 150 are arranged on the front and rear of the user, and the second peripheral subassemblies 160 are arranged on the left and right of the user. The peripheral subassemblies 150, 160 may be of various sizes or lengths. For example, the peripheral subassemblies 150,160 may extend to the waist opening and/or leg openings of the garment 200. For example as shown in FIG. 10A, the second peripheral subassemblies 160 extend around the leg openings of the garment 200.

Figure 10B:
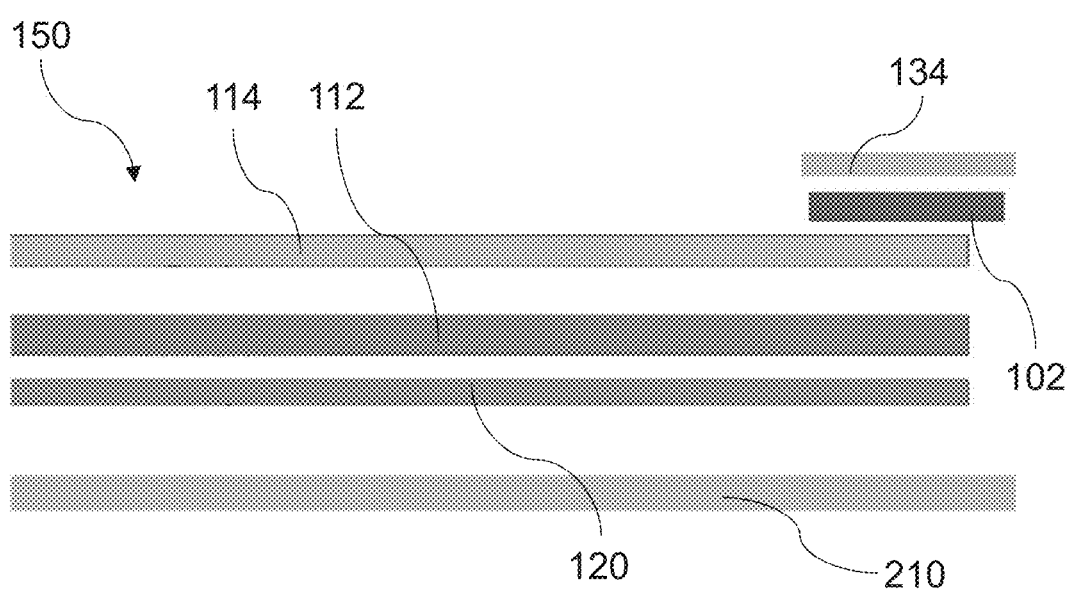

Further, the first peripheral subassembly 150 and second peripheral subassembly 160 are structurally different from each other. An exemplary structural configuration of the first peripheral subassembly 150 is shown in FIG. 10B. The first peripheral subassembly 150 includes a pad attaching element 134 that is bonded to the wicking layer 114 via an adhesive film 102. The pad attaching element 134 may be liquid impermeable or treated with a hydrophobic material.

Figure 10C:
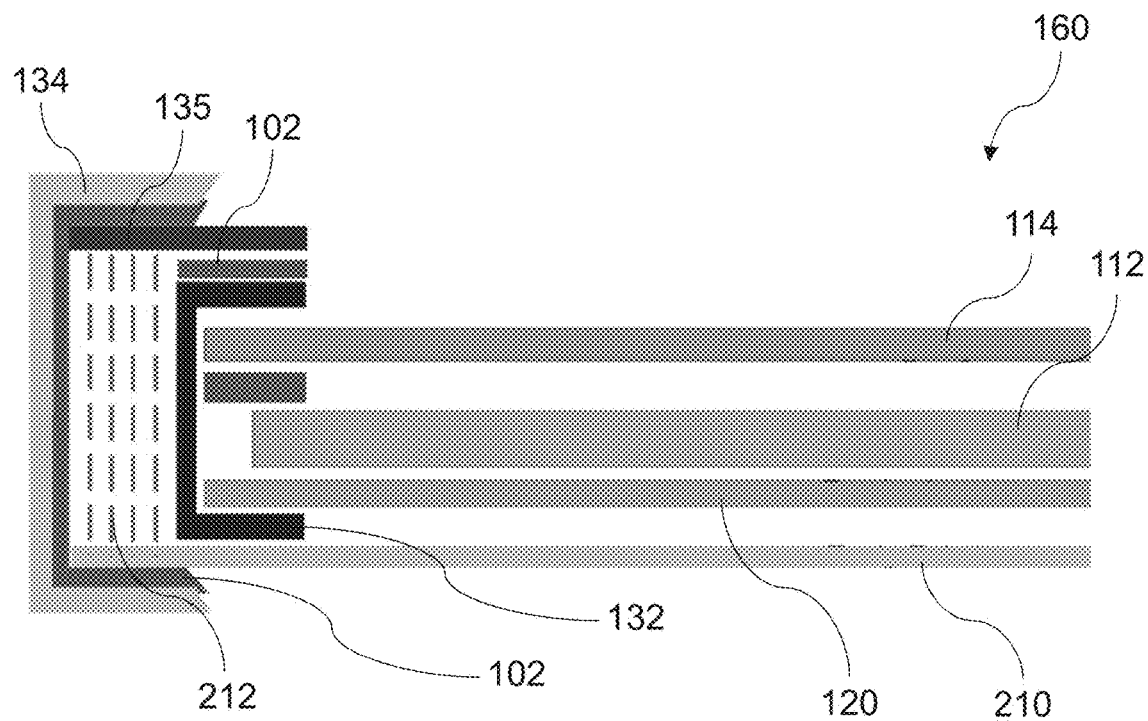

An exemplary structural configuration of the second peripheral subassembly 160 is shown in FIG. 10C. The second peripheral subassembly 160 includes a sealing element 132 in a C-shaped form that is attached to the upper interface of the wicking layer 114 and the lower interface of the barrier layer 120 to seal the periphery of the absorbent pad 100. The second peripheral subassembly 160 includes a pad attaching element 134 and a second pad attaching element 135. The second pad attaching element 135 is bonded to the sealing element 132 via an adhesive film 102 and is stitched to the fabric body 210. The pad attaching element 134 is in a C-shaped form and is bonded to the second pad attaching element 135 and the outside of the fabric body 210 via a C-shaped adhesive film 102 to cover the visible stitch lines 212. The pad attaching element 134 and second pad attaching element 135 may be optionally liquid impermeable or treated with a hydrophobic material.

Figure 10D:
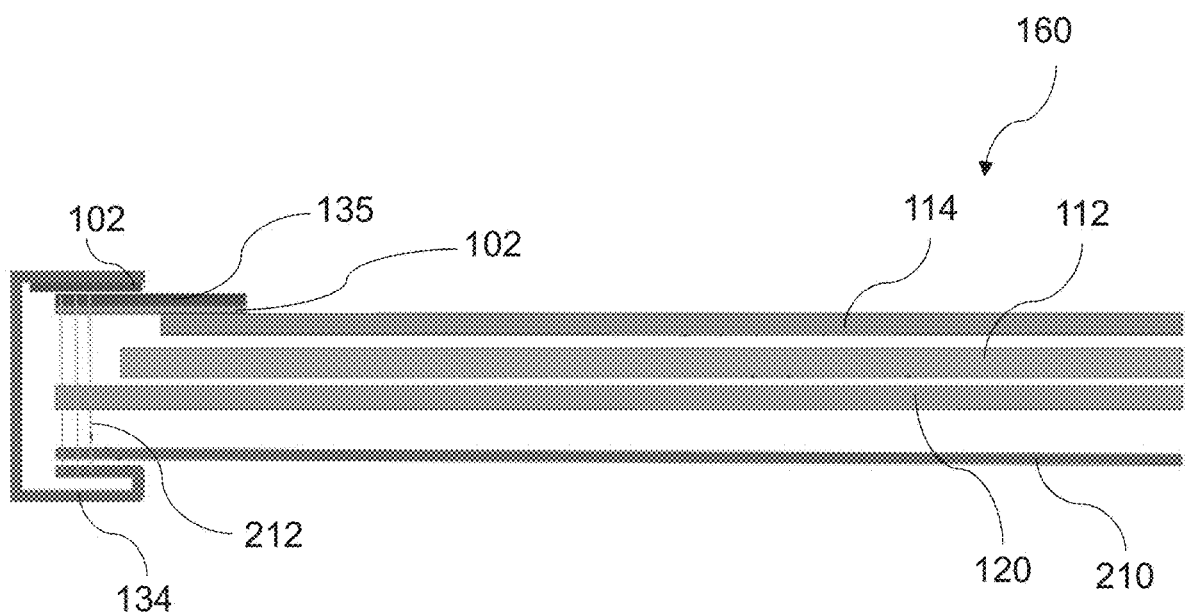

Another exemplary structural configuration of the second peripheral subassembly 160 is shown in FIG. 10D. The second peripheral subassembly 160 includes a pad attaching element 134 and a second pad attaching element 135. The second pad attaching element 135 is bonded to the upper interface of the wicking layer 114 and the upper interface of the barrier layer 120 via an adhesive film 102. The pad attaching element 134, which is in a C-shaped form and partially folded, is bonded to the second pad attaching element 135 via an adhesive film 102 and stitched to the outside of the fabric body 210 to cover the visible stitch lines 212. The pad attaching element 134 and second pad attaching element 135 together with the respective adhesive films 102 cooperatively seal the periphery of the absorbent pad 100. The pad attaching element 134 and second pad attaching element 135 may be liquid impermeable or treated with a hydrophobic material.

Figure 11A:
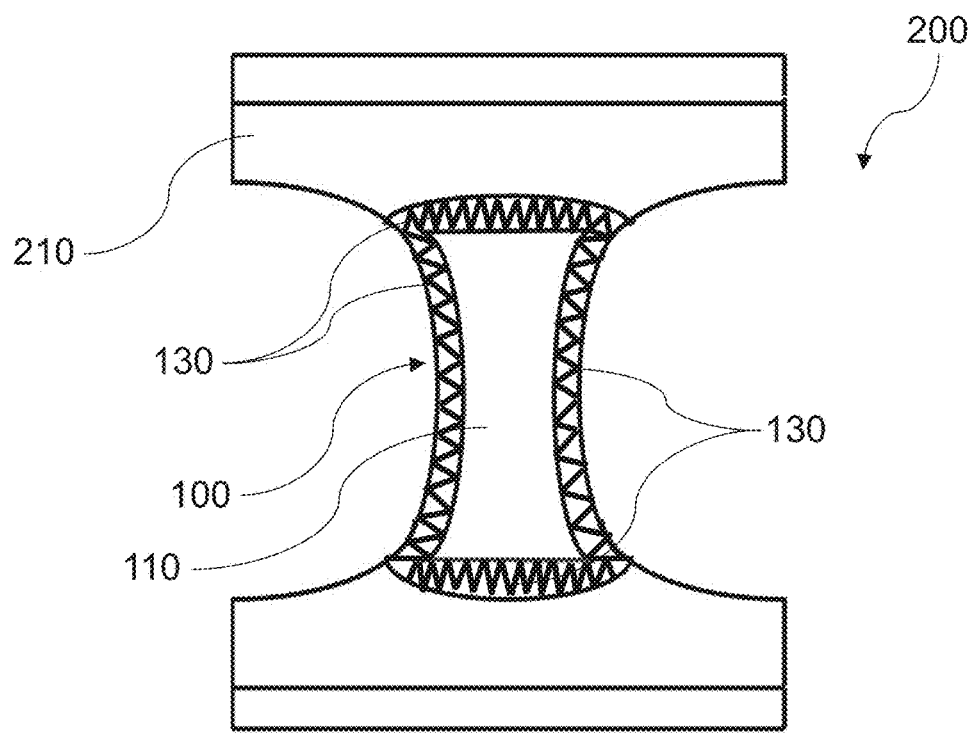
FIGS. 11A and 11B are further illustrations of the peripheral assembly.
Figure 11B:
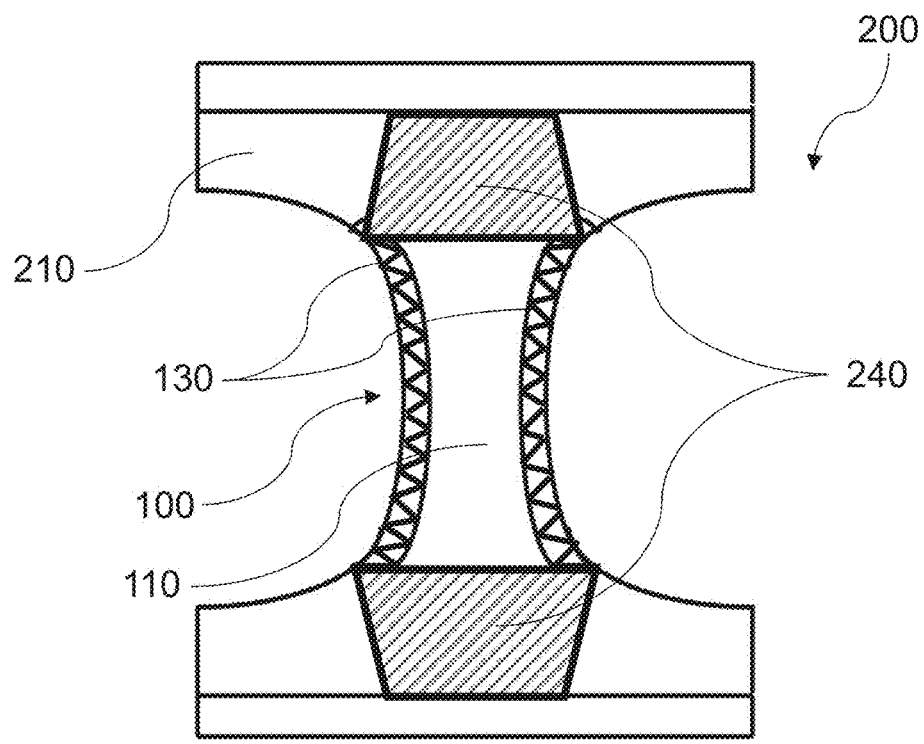

In some embodiments as shown in FIGS. 11A and 11B, the peripheral assembly 130 may include a hydrophobic material and/or a stretchable material. For example, the pad attaching element 134 includes a hydrophobic material and/or a stretchable material. The hydrophobic material may be a water-repellent finish such as those described above. The fabric body 210 may also include a hydrophobic material and/or a stretchable material. For example, areas 240 of the fabric body 210 at the front and rear of the absorbent pad 100 include a hydrophobic material and/or a stretchable material. For example, the waist opening and/or leg openings of the garment 200 include a hydrophobic material and/or a stretchable material. The stretchability of the absorbent pad 100 and garment 200, particularly with the use of a stretchable pad attaching element 134, allows the garment 200 to be adjusted to the body shape of the user, thereby improving the fitting and reducing risk of leakages.

Figure 12A:
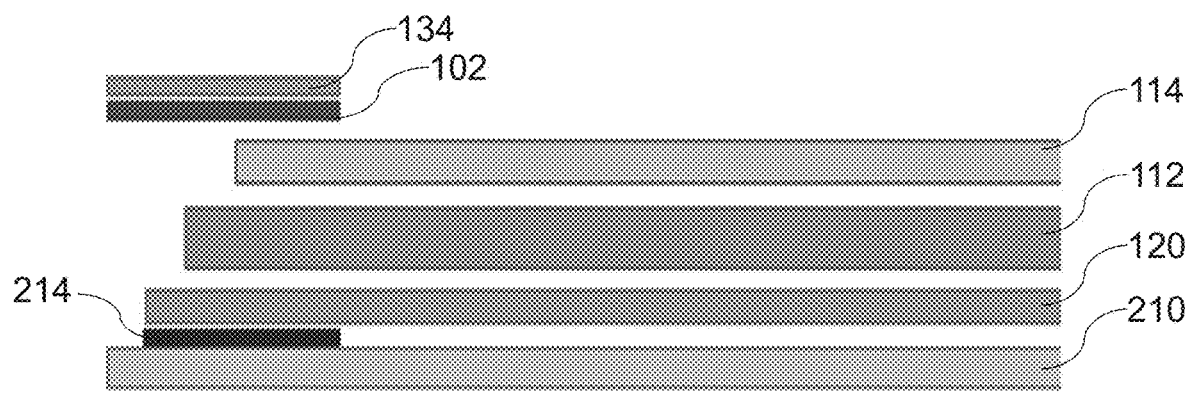
FIGS. 12A to 12O are further illustrations of attaching the absorbent pad to the garment.
Figure 12B:
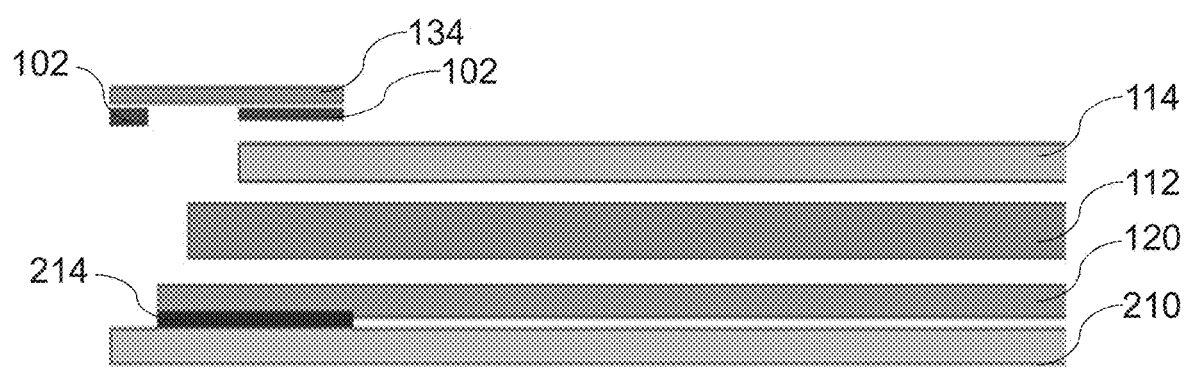
Figure 12C:
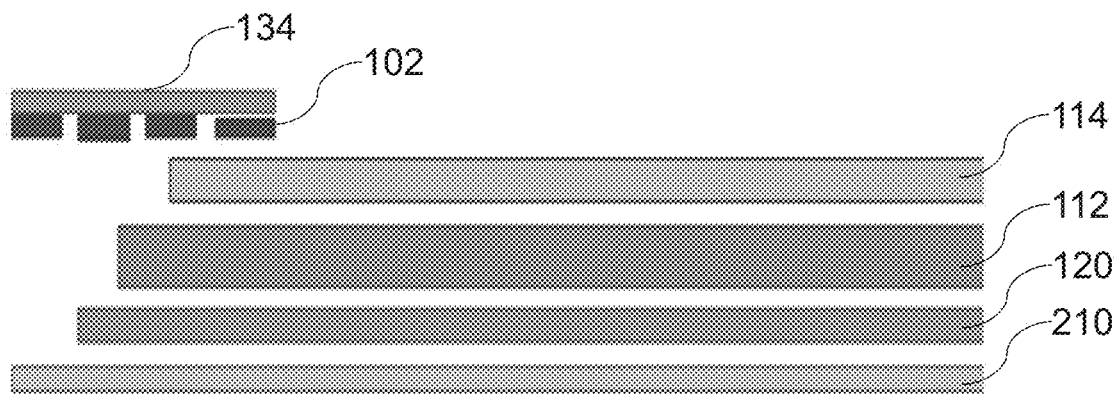
Figure 12D:
Figure 12E:
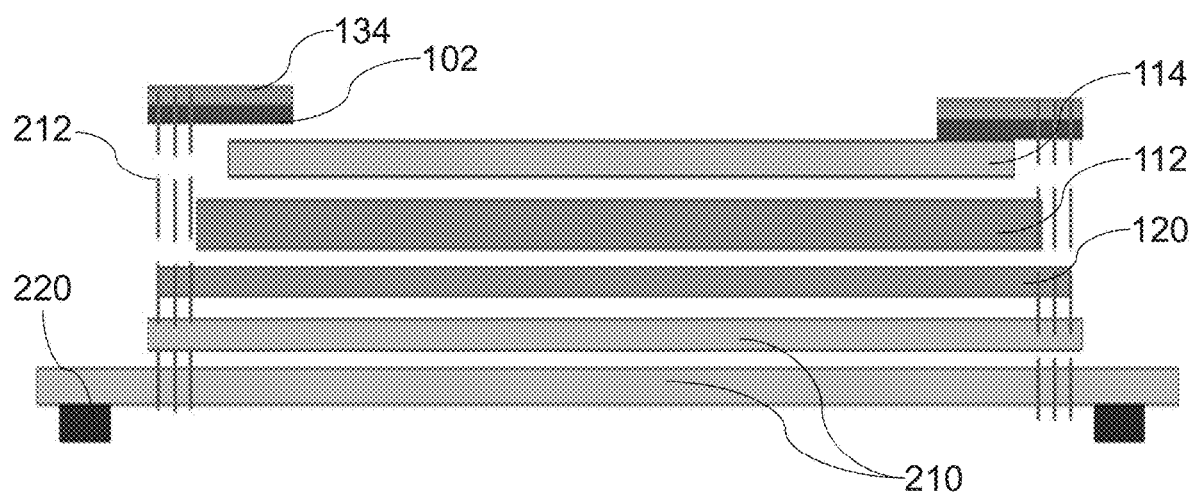
Figure 12F:
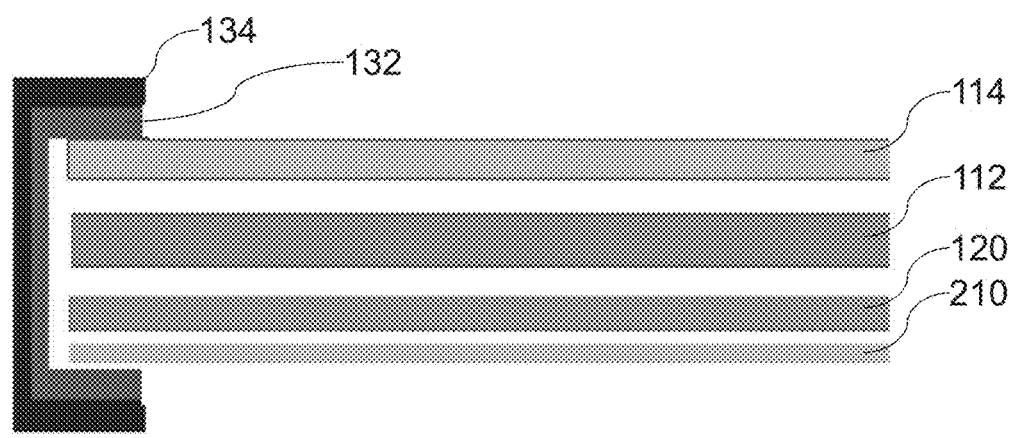
Figure 12G:
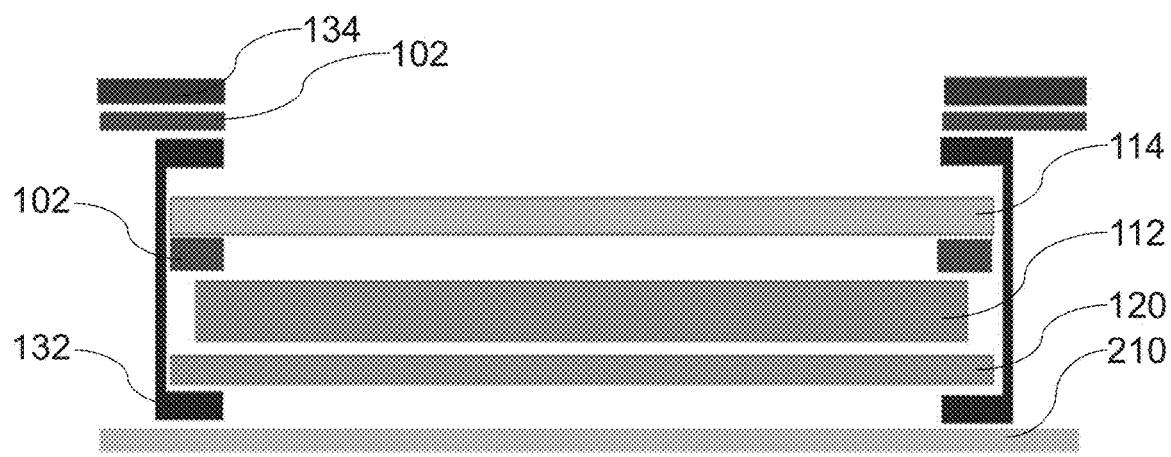
Figure 12H:
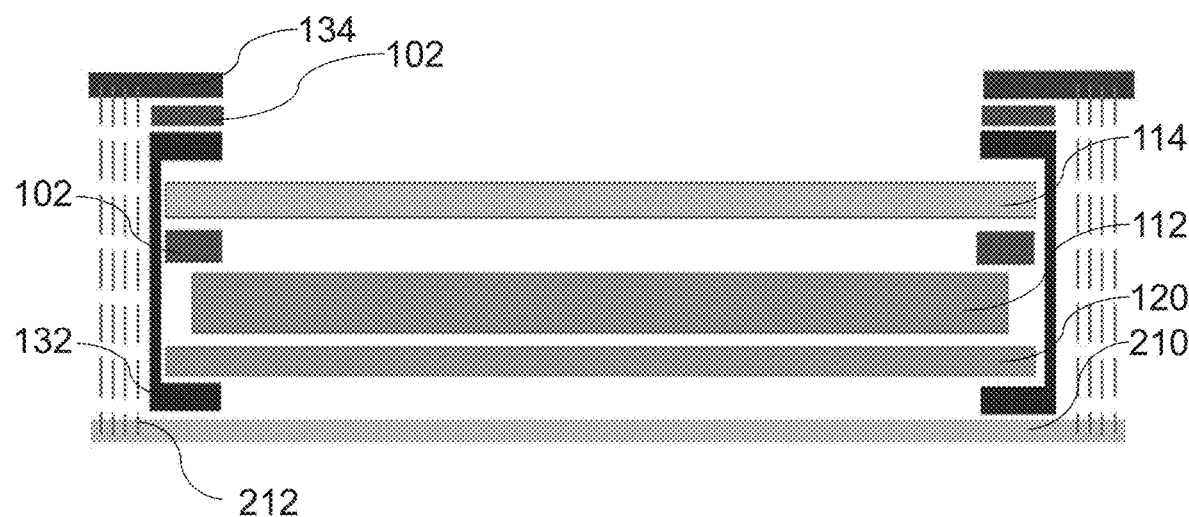
Figure 12I:
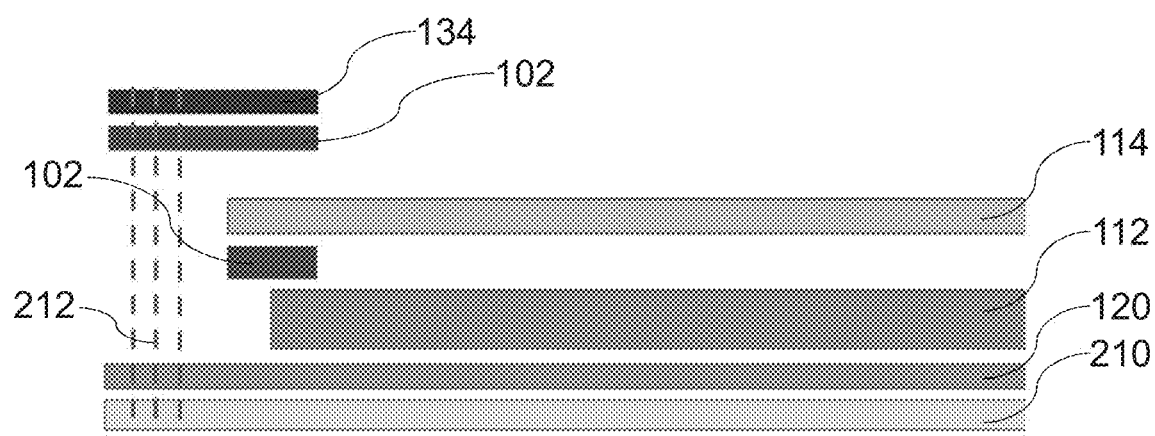
Figure 12J:
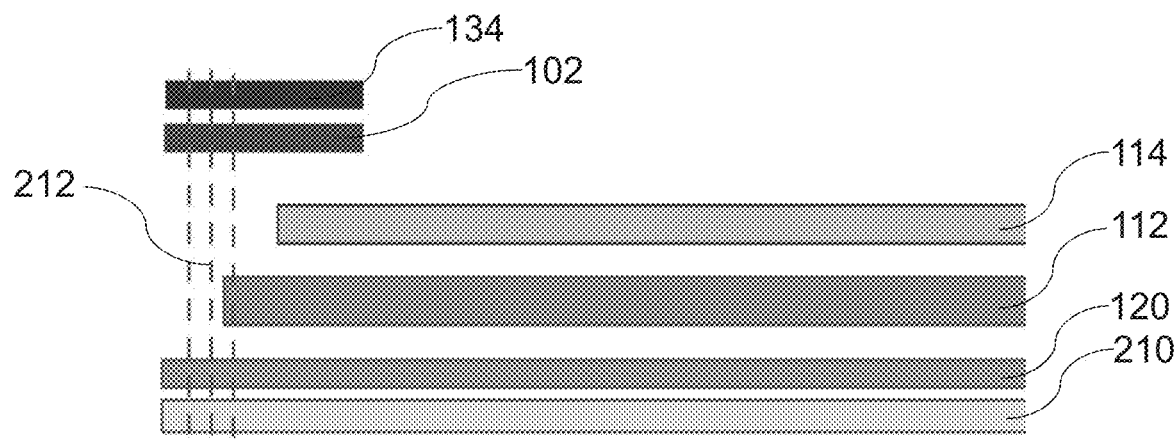
Figure 12K:
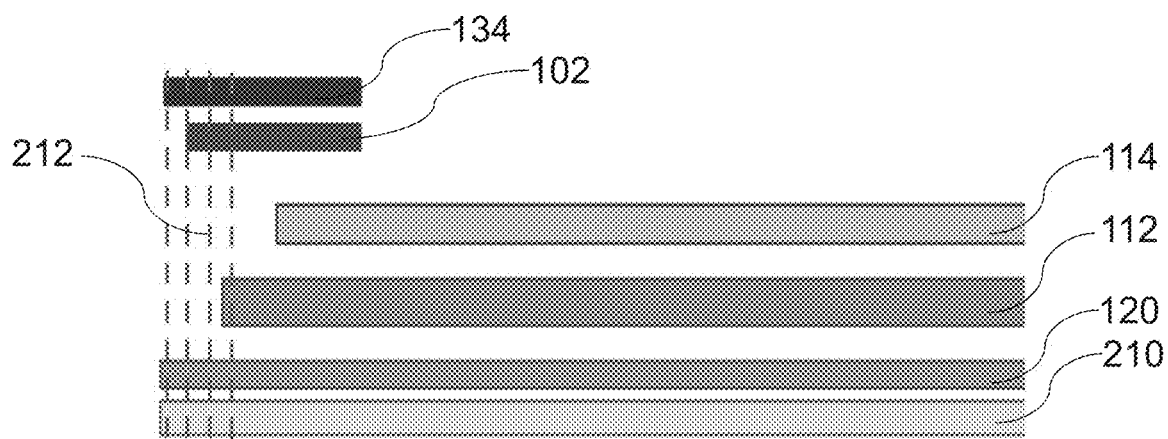
Figure 12L:
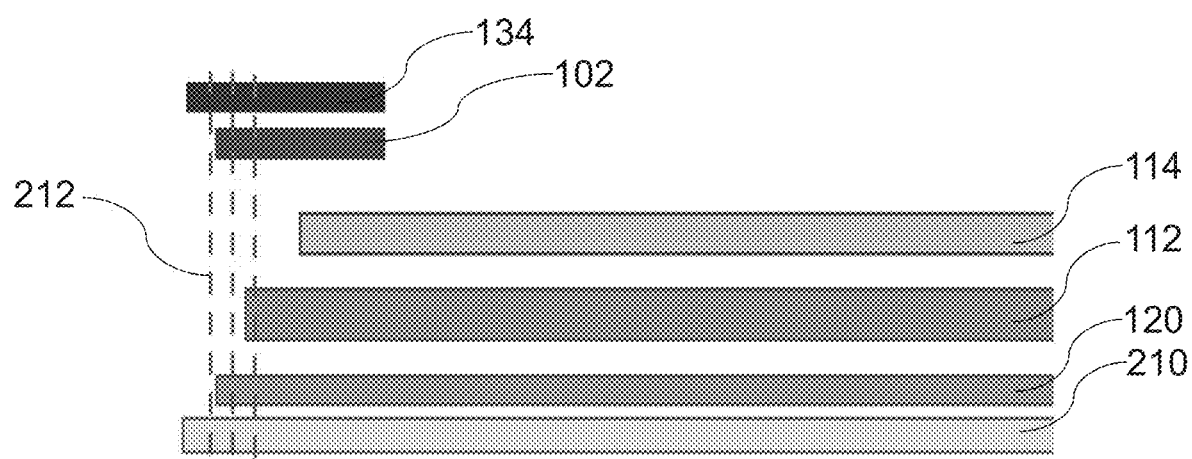
Figure 12M:
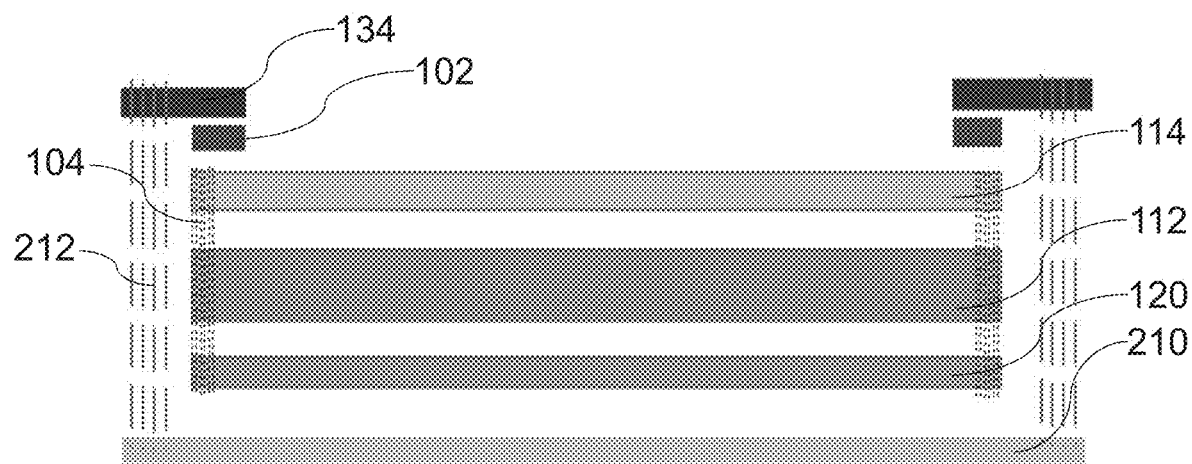
Figure 12N:
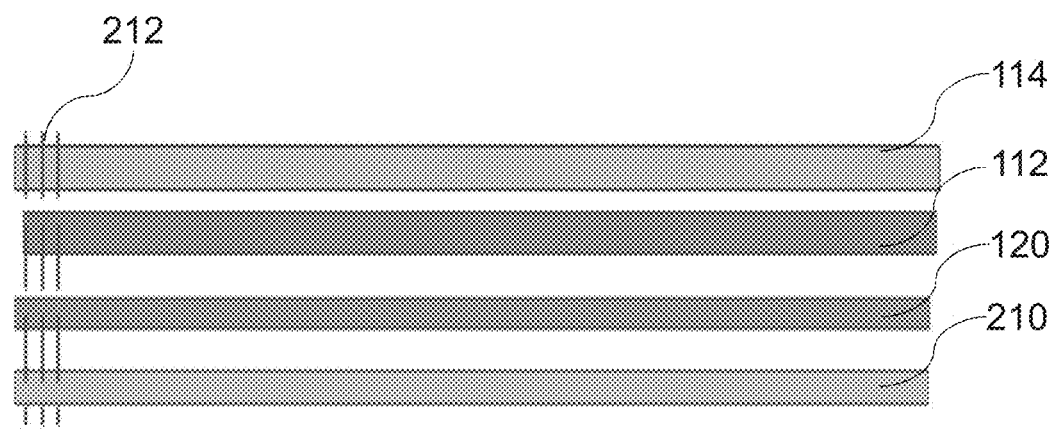
Figure 12O:
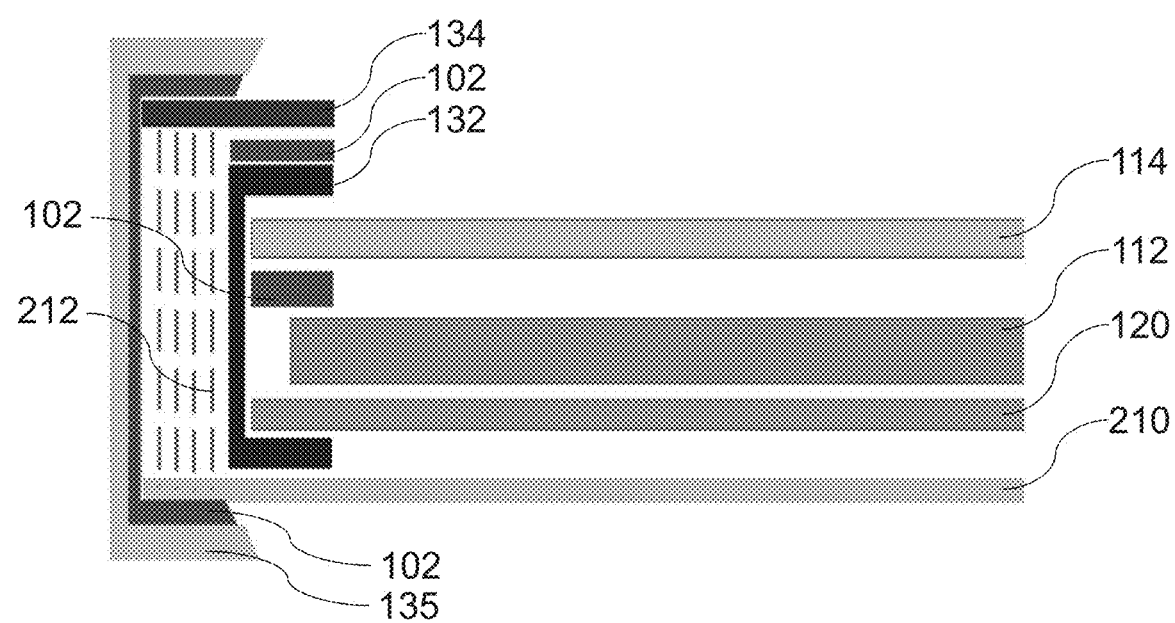
Figure 13A:
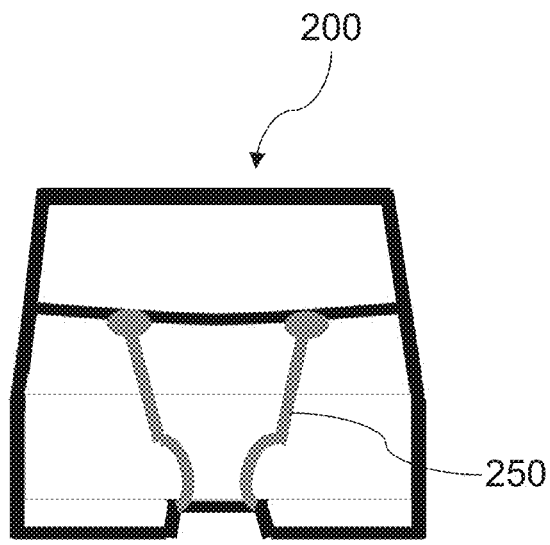
FIGS. 13A to 13D are various illustrations of the garment comprising tensioning elements.
Figure 13B:
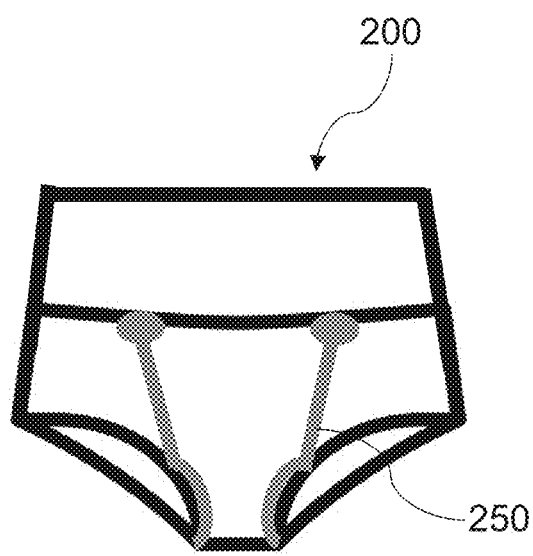
Figure 13C:
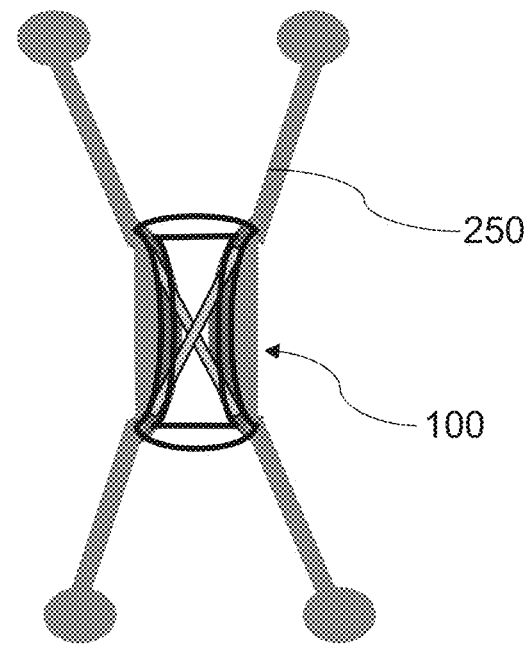
Figure 13D:
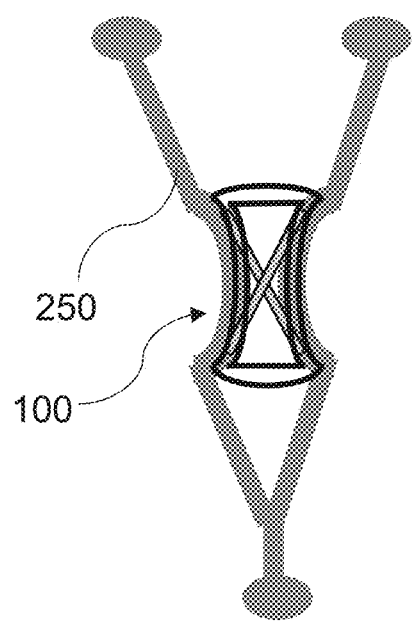

FIGS. 12A to 12O show various ways of attaching the absorbent pad 100 to the garment 200, particularly the cross-sections of the left, right, front, and rear of the absorbent pad 100 when attached to the fabric body 210. Particularly, the absorbent pad 100 is attached to the fabric body 210 using the pad attaching element 134, which is a separate piece of fabric material that may be optionally liquid impermeable or treated with a hydrophobic material.

In one embodiment as shown in FIG. 12A, the absorbent pad 100 is attached to the fabric body 210 via the peripheral assembly 130. The peripheral assembly 130 includes the pad attaching element 134 and a double-sided adhesive film 102 that bonds the pad attaching element 134 to the wicking layer 114 and fabric body 210. The adhesive film 102 may optionally also bond the pad attaching element 134 to the absorbent layer 112 and barrier layer 120. Further, there is no bonding or adhesive in the peripheral area 214 between the fabric body 210 and barrier layer 120. The left, right, front, and rear of the absorbent pad 100 may have the same cross-section configuration.

In one embodiment as shown in FIG. 12B, the absorbent pad 100 is attached to the fabric body 210 via the peripheral assembly 130, similar to the embodiment of FIG. 12A. However, instead of a single double-sided adhesive film 102, the embodiment of FIG. 12B has two separate double-sided adhesive films 102 that bond the pad attaching element 134 to the wicking layer 114 and fabric body 210, respectively. There is also no bonding or adhesive in the peripheral area 214 between the fabric body 210 and barrier layer 120. The left, right, front, and rear of the absorbent pad 100 may have the same cross-section configuration.

In one embodiment as shown in FIG. 12C, the absorbent pad 100 is attached to the fabric body 210 via the peripheral assembly 130. The peripheral assembly 130 includes the pad attaching element 134 and drop-on-demand glue 102 that bonds the pad attaching element 134 to the wicking layer 114 and fabric body 210. The drop-on-demand glue 102 may optionally also bond the pad attaching element 134 to the absorbent layer 112 and barrier layer 120. The wicking layer 114, absorbent layer 112, and barrier layer 120 may be laminated or glued to each other, such as by using adhesive at the plurality of discrete points 116. The left, right, front, and rear of the absorbent pad 100 may have the same cross-section configuration.

In one embodiment as shown in FIG. 12D, the absorbent pad 100 is attached to the fabric body 210 via the peripheral assembly 130. The peripheral assembly 130 includes the pad attaching element 134 and a double-sided adhesive film 102 that bonds the pad attaching element 134 to the wicking layer 114 and fabric body 210. The adhesive film 102 may optionally also bond the pad attaching element 134 to the absorbent layer 112 and barrier layer 120. Further, the pad attaching element 134 is stitched 212 to the fabric body 210 and barrier layer 120. This cross-section configuration may apply to the left and right of the absorbent pad 100, similar to the cross-section of the second peripheral subassembly 160.

In one embodiment as shown in FIG. 12E, the absorbent pad 100 is attached to the fabric body 210 via the peripheral assembly 130. The peripheral assembly 130 includes the pad attaching element 134 and a double-sided adhesive film 102 that bonds the pad attaching element 134 to the wicking layer 114 and an inner layer of the fabric body 210. The adhesive film 102 may optionally also bond the pad attaching element 134 to the absorbent layer 112 and barrier layer 120. Further, the pad attaching element 134 is stitched 212 to the barrier layer 120 and the inner and outer layers of the fabric body 210. Further, the outer layer of the fabric body 210 may include fasteners 220 such as snap buttons and/or touch fasteners. This cross-section configuration may apply to the left and right of the absorbent pad 100, similar to the cross-section of the second peripheral subassembly 160.

In one embodiment as shown in FIG. 12F, the absorbent pad 100 is attached to the fabric body 210 via the peripheral assembly 130. The peripheral assembly 130 includes the liquid impermeable sealing element 132 and the pad attaching element 134. The sealing element 132 may be a double-sided adhesive film. The pad attaching element 134 is attached to the wicking layer 114 and fabric body 210 via the sealing element 132. The wicking layer 114, absorbent layer 112, and barrier layer 120 may be laminated or glued to each other, such as by using adhesive at the plurality of discrete points 116. This cross-section configuration may apply to the left and right of the absorbent pad 100, similar to the cross-section of the second peripheral subassembly 160.

In one embodiment as shown in FIG. 12G, the absorbent pad 100 is attached to the fabric body 210 via the peripheral assembly 130. The peripheral assembly 130 includes the liquid impermeable sealing element 132 and the pad attaching element 134. The sealing element 132 may be a single-sided adhesive film that bonds the peripheries of the wicking layer 114 and barrier layer 120. A first double-sided adhesive film 102 bonds the peripheries of the wicking layer 114, absorbent layer 112, and barrier layer 120 together. Further, a second double-sided adhesive film 102 bonds the pad attaching element 134 to the sealing element 132 and fabric body 210. This cross-section configuration may apply to the left and right of the absorbent pad 100, similar to the cross-section of the second peripheral subassembly 160.

In one embodiment as shown in FIG. 12H, the absorbent pad 100 is attached to the fabric body 210 via the peripheral assembly 130, similar to the embodiment of FIG. 12G. However, the second double-sided adhesive film 102 bonds part of the pad attaching element 134 to the sealing element 132. Another part of the pad attaching element 134 is stitched to the fabric body 210. This cross-section configuration may apply to the left and right of the absorbent pad 100, similar to the cross-section of the second peripheral subassembly 160.

In one embodiment as shown in FIG. 12I, the absorbent pad 100 is attached to the fabric body 210 via the peripheral assembly 130. The peripheral assembly 130 includes the pad attaching element 134 and double-sided adhesive films 102. A first double-sided adhesive film 102 bonds the peripheries of the wicking layer 114, absorbent layer 112, and barrier layer 120 together. A second double-sided adhesive film 102 bonds the pad attaching element 134 to the sealing element 132 and fabric body 210. Further, the pad attaching element 134 is stitched to the fabric body 210. This cross-section configuration may apply to the left and right of the absorbent pad 100, similar to the cross-section of the second peripheral subassembly 160.

In one embodiment as shown in FIG. 12J, the absorbent pad 100 is attached to the fabric body 210 via the peripheral assembly 130. The peripheral assembly 130 includes the pad attaching element 134 and a double-sided adhesive film 102 that bonds the pad attaching element 134 to the peripheries of the wicking layer 114, absorbent layer 112, and barrier layer 120. Further, the pad attaching element 134 is stitched 212 to the fabric body 210. Specifically, at least some of the stitch lines 212 pass through the pad attaching element 134, adhesive film 102, barrier layer 120, and fabric body 210, and at least some of the stitch lines 212 further pass through the absorbent layer 112. This cross-section configuration may apply to the left and right of the absorbent pad 100, similar to the cross-section of the second peripheral subassembly 160.

In one embodiment as shown in FIG. 12K, the absorbent pad 100 is attached to the fabric body 210 via the peripheral assembly 130, similar to the embodiment of FIG. 12J. However, the pad attaching element 134 is longer than the adhesive film 102 such that part of the pad attaching element 134 is stitched directly to the fabric body 210. Specifically, at least some of the stitch lines 212 pass through the pad attaching element 134, barrier layer 120, and fabric body 210 without passing through the adhesive film 102. This cross-section configuration may apply to the left and right of the absorbent pad 100, similar to the cross-section of the second peripheral subassembly 160.

In one embodiment as shown in FIG. 12L, the absorbent pad 100 is attached to the fabric body 210 via the peripheral assembly 130, similar to the embodiment of FIG. 12K. However, part of the pad attaching element 134 is stitched directly to the fabric body 210, such that at least some of the stitch lines 212 pass through the pad attaching element 134 and fabric body 210 without passing through the adhesive film 102 or barrier layer 120. This cross-section configuration may apply to the left and right of the absorbent pad 100, similar to the cross-section of the second peripheral subassembly 160.

In one embodiment as shown in FIG. 12M, the absorbent pad 100 is attached to the fabric body 210 via the peripheral assembly 130. The peripheral assembly 130 includes the pad attaching element 134 and a double-sided adhesive film 102. The double-sided adhesive film 102 bonds part of the pad attaching element 134 to the sealing element 132. Another part of the pad attaching element 134 is stitched to the fabric body 210. Further, peripheries of the wicking layer 114, absorbent layer 112, and barrier layer 120 are bonded together by ultrasonic bonding 104. This cross-section configuration may apply to the left and right of the absorbent pad 100, similar to the cross-section of the second peripheral subassembly 160.

In one embodiment as shown in FIG. 12N, the absorbent pad 100 is attached to the fabric body 210 via the peripheral assembly 130. The peripheral assembly 130 includes the threads or yarns that stitch 212 the peripheries of the absorbent pad 100 to the fabric body 210. More specifically, the threads or yarns are made or include a liquid impermeable or hydrophobic material. This cross-section configuration may apply to the left and right of the absorbent pad 100, similar to the cross-section of the second peripheral subassembly 160.

In one embodiment as shown in FIG. 12O, the absorbent pad 100 is attached to the fabric body 210 via the peripheral assembly 130. The peripheral assembly 130 includes the liquid impermeable sealing element 132, pad attaching element 134, and second pad attaching element 135. The sealing element 132 may be a single-sided adhesive film that bonds the peripheries of the wicking layer 114 and barrier layer 120. A first double-sided adhesive film 102 bonds the peripheries of the wicking layer 114, absorbent layer 112, and barrier layer 120 together. A second double-sided adhesive film 102 bonds part of the pad attaching element 134 to the sealing element 132. Another part of the pad attaching element 134 is stitched to the fabric body 210. A third double-sided adhesive film 102 bonds the second pad attaching element 135 is bonded to the pad attaching element 134 and fabric body 210. Further, the second pad attaching element 135 is folded to cover the visible stitch lines 212. This cross-section configuration may apply to the left and right of the absorbent pad 100, similar to the cross-section of the second peripheral subassembly 160.

In some embodiments as shown in FIGS. 13A to 13D, the garment 200 includes a set of tensioning elements 250 connected to the absorbent pad 100. For example, the tensioning elements 250 are anchored from the waist opening and/or leg openings and connected to the absorbent pad 100. For example, the tensioning elements 250 may include strings that are connected in tension to the absorbent pad 100. The tensioning elements 250 cause the absorbent pad 100 to compress against the user's body and capture bodily fluids more effectively. The compression from the absorbent pad 100 can help to provide relief to uncomfortable conditions such as pelvic organ prolapse. Specifically, the absorbent pad 100 allows more pressure to be exerted to the vulva area to improve comfort. The compression from the absorbent pad 100 can also be used to manage other situations such as mild bladder prolapse and uterine prolapse. The tensioning elements 250 may be arranged differently to adjust the tension forces and the compression force and position against the user's body.

In some embodiments as shown in FIG. 14A, the peripheral assembly 130 may include a set of liquid detection elements 170 configured to change state in response to contact with liquid. For example, the pad attaching element 134/second pad attaching element 135 include the liquid detection elements 170. The liquid detection elements 170 may include a hydrochromic material configured to change colour in response to contact with liquid. For example, the hydrochromic material may include hydrochromic prints and water-based pigments. Additionally or alternatively, the liquid detection elements 170 may include a deformable foam material, such as one comprising polyurethane, configured to deform in response to contact with liquid.

In some embodiments as shown in FIGS. 14B and 14C, the absorbent pad 100 may include the top layer 140 disposed on the wicking layer 114. The top layer 140 may include similar liquid detection elements 170, particularly the hydrochromic material as described further above. Similarly, the garment 200 may include a hydrochromic material. For example, the hydrochromic material is disposed at the fabric body 210, such as the waist opening and/or leg openings, and on the inside and/or outside of the garment 200. For example, the hydrochromic material is disposed on the outside of the garment 200 to act as an exterior wetness indicator, particularly to indicate any liquid leakage from the absorbent pad 100.

Figure 15:
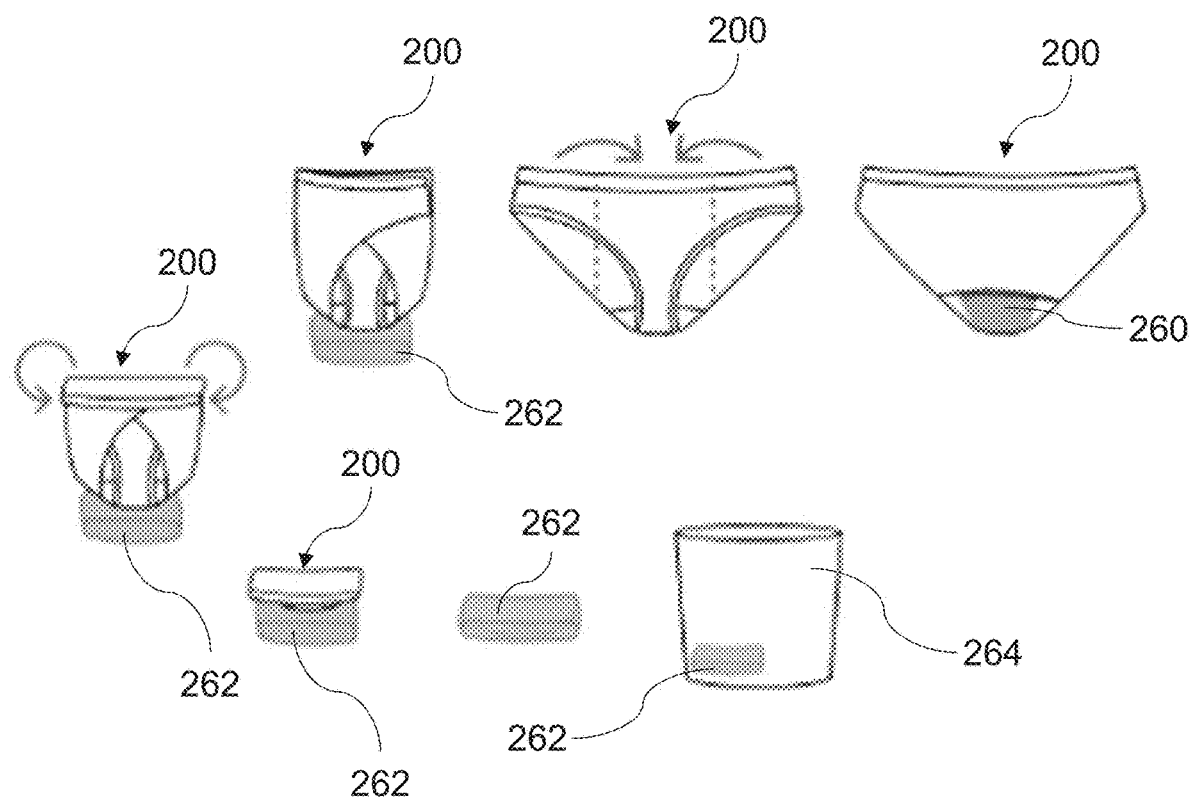
FIG. 15 is an illustration of the garment comprising a pocket and a laundry bag.

In some embodiments as shown in FIG. 15, the garment 200 includes a pocket 260 and the pocket 260 includes a laundry bag 262 therein. The laundry bag 262 is removable from the pocket 260 for holding the garment 200 in the laundry bag 262. The laundry bag 262 with the garment 200 inside can be sent together to the laundry 264. For example, the laundry bag 262 is completely removable from the pocket 260 and may be replaced if it is damaged. The pocket 260 and laundry bag 262 improve the convenience of handling and washing of a dirty garment 200. The pocket 260 may be disposed underneath or at the back of the garment 200. The pocket 260 may include an opening to remove the laundry bag 262 and the opening may be secured with a suitable closing mechanism, such as a waterproof cord or zipper. The pocket 260 may include a stretchable material and the laundry bag 262 may include a water-resistant material and/or an odour-resistant material.

In some embodiments, instead of having the laundry bag 262, the pocket 260 is positioned on the outside of the garment 200. The garment 200 can be folded inwards into the pocket 260 such that the absorbent pad 100 is covered by the pocket 260.

Figure 16:
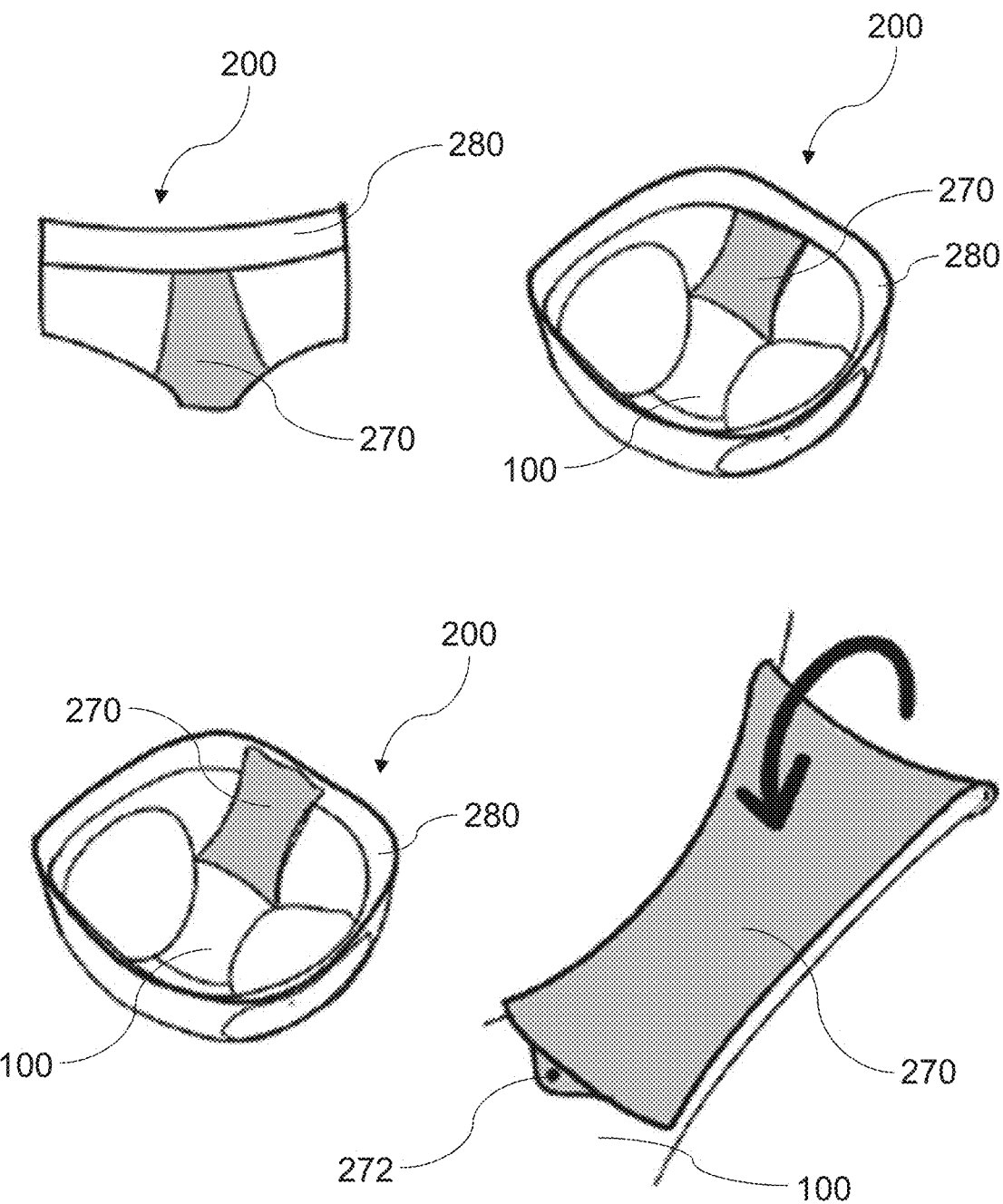
FIG. 16 is an illustration of the garment comprising a second wicking layer attachable to the absorbent pad.

In some embodiments as shown in FIG. 16, the garment 200 includes a second wicking layer 270 fixed to a rear part of the absorbent pad 100 and removably attached to a waistband 280 of the garment 200. The second wicking layer 270 is detachable from the waistband 280 and reattachable to a front part of the absorbent pad 100 and thereby overlay the second wicking layer 270 on the absorbent pad 100. For example, the second wicking layer 270 overlays the wicking layer 114 or top layer 140 of the absorbent pad 100. The second wicking layer 270 may include a set of fasteners 272 for fastening to the front part of the absorbent pad 100. The fasteners 272 may include snap buttons and/or touch fasteners. The second wicking layer 270 may be used by the user when needed to provide additional liquid transfer capabilities and/or better comfort, such as if the absorbent pad 100 feels wet and uncomfortable for the user.

Various embodiments of the present disclosure describe an absorbent pad 100 that is leak-proof and enables the efficient transport of liquid from the surface of the absorbent pad 100, such as the wicking layer 114, to the underlying absorbent layer 112. The garment 200 fitted with the absorbent pad 100 also exhibits the properties associated with the absorbent pad 100. For example, as the absorbent pad 100 provides sufficient and effective liquid absorption, when the garment 200 fitted with the absorbent pad 100 is in the form of an undergarment, there may be no need to use a disposable tampon/pad in conjunction with the undergarment. Further, the absorbent pad 100 is thinner than conventional products, enabling the garment 200 to be more attractive and more comfortable to wear than garments containing conventional pads, while providing enhanced protection from leakage. Some embodiments describe attaching the absorbent pad 100 to the garment 200 directly via stitching and without the use of additional fabric strips like those of the pad attaching elements 134, 135. Such embodiments obviate the use of such fabric strips and allow the use of other options to seal the periphery of the absorbent pad 100, such as but not limited to ultrasonic welding and fusible yarns.

Many embodiments of the absorbent pad 100 and the garment 200 are described in the present disclosure. It will be appreciated that various aspects of one or more embodiments of the absorbent pad 100 and/or garment 200 may apply equally to another one or more other embodiments, and such aspects are not further elaborated upon for purpose of brevity.

In the foregoing detailed description, embodiments of the present disclosure in relation to an absorbent pad for use in a garment and a garment comprising the absorbent pad are described with reference to the provided figures. The description of the various embodiments herein is not intended to call out or be limited only to specific or particular representations of the present disclosure, but merely to illustrate non-limiting examples of the present disclosure. The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

Statements

1. An absorbent pad for use in a garment, the absorbent pad comprising:
   a liquid impermeable barrier layer;
   a functional assembly attached to the liquid impermeable barrier layer, the functional assembly comprising:
   an absorbent layer attached to the liquid impermeable barrier layer, the absorbent layer for absorbing liquid; and
   a wicking layer attached to the absorbent layer, the wicking layer arranged to face towards a skin of a user when in use, the wicking layer for transferring liquid to the absorbent layer; and
   a peripheral assembly attached to a periphery of the functional assembly, at least part of the peripheral assembly being liquid impermeable,
   wherein the wicking layer and the absorbent layer are attached at a plurality of discrete points between them to facilitate liquid transfer from the wicking layer to the absorbent layer via areas around the discrete points.

2. The absorbent pad according to statement 1, wherein the wicking layer and the absorbent layer are knitted together with cross-linking yarns at the discrete points.

3. The absorbent pad according to statement 1, wherein the wicking layer and the absorbent layer are attached together by lamination and the discrete points comprise an adhesive material.

4. The absorbent pad according to any one of statements 1 to 3, wherein the discrete points are distributed throughout the wicking and absorbent layers and/or at peripheries of the wicking and absorbent layers.

5. The absorbent pad according to any one of statements 1 to 4, wherein peripheries of the wicking and absorbent layers are attached together by an adhesive film.

6. The absorbent pad according to any one of statements 1 to 5, wherein the wicking layer comprises an array of hydrophobic yarns and hydrophilic yarns that form channels for guiding liquid flow.

7. The absorbent pad according to any one of statements 1 to 6, wherein the wicking layer comprises a linear array of hydrophobic material and hydrophilic material.

8. The absorbent pad according to statement 7, wherein the wicking layer is made of the hydrophilic material and comprises alternating lines of hydrophobic material disposed on top of the hydrophilic material.

9. The absorbent pad according to any one of statements 1 to 8, wherein the functional assembly comprises a top layer attached to the wicking layer and arranged to face towards the user's skin when in use.

10. The absorbent pad according to statement 9, wherein the top layer comprises one or more of a hydrophilic material, a hydrophobic material, and a hydrochromic material.

11. The absorbent pad according to statement 9 or 10, wherein the top layer comprises an array of openings for liquid transfer from the user's skin to the wicking layer, the top layer comprising a hydrophobic material.

12. The absorbent pad according to statement 9 or 10, wherein the top layer comprises an array of channels for guiding liquid flow, the channels comprising a hydrophobic material.

13. The absorbent pad according to statement 12, wherein the hydrophobic material comprises a cured polymeric material that is patterned to form the channels.

14. The absorbent pad according to statement 9 or 10, wherein the top layer comprises a linear array of hydrophobic material and hydrophilic material.

15. The absorbent pad according to statement 14, wherein the top layer is made of the hydrophilic material and comprises alternating lines of hydrophobic material disposed on top of the hydrophilic material.

16. The absorbent pad according to any one of statements 9 to 15, wherein the top layer comprises a set of liquid detection elements configured to change state in response to contact with liquid.

17. The absorbent pad according to statement 16, wherein the liquid detection elements comprise a hydrochromic material configured to change colour in response to contact with the liquid.

18. The absorbent pad according to any one of statements 1 to 17, wherein the wicking layer and/or absorbent layer comprises a foam material and/or a spacer fabric material.

19. The absorbent pad according to statement 18, wherein the absorbent pad is moulded such that the functional assembly comprises a deformed portion, the deformed portion being a raised portion or a recessed portion.

20. The absorbent pad according to any one of statements 1 to 19, wherein the functional assembly is shaped using darts.

21. The absorbent pad according to any one of statements 1 to 20, wherein the peripheral assembly comprises a pad attaching element attached to the periphery of the functional assembly, the pad attaching element optionally being liquid impermeable.

22. The absorbent pad according to statement 21, wherein the pad attaching element forms a liquid impermeable ridge on the periphery of the functional assembly.

23. The absorbent pad according to statement 21 or 22, wherein the peripheral assembly comprises a plurality of fasteners attached to the pad attaching element, the fasteners configured for fastening the absorbent pad to the garment, the fasteners optionally comprising snap buttons and/or touch fasteners.

24. The absorbent pad according to any one of statements 21 to 23, wherein the peripheral assembly comprises:
a first peripheral subassembly arranged along a front and rear of the absorbent pad; and
a second peripheral subassembly arranged along a left and right of the absorbent pad,
wherein the first and second peripheral subassemblies are structurally different from each other.

25. The absorbent pad according to statement 24, wherein the first peripheral subassembly includes the pad attaching element, the pad attaching element bonded to the wicking layer.

26. The absorbent pad according to statement 24 or 25, wherein the second peripheral subassembly comprises:
a sealing element attached to the wicking layer and barrier layer;
the pad attaching element; and
a second pad attaching element attached to the sealing element and for stitching to the garment,
wherein the pad attaching element is attached to the second pad attaching element and for attaching to the garment, the pad attaching element arranged to cover the stitching.

27. The absorbent pad according to statement 24 or 25, wherein the second peripheral subassembly comprises:
the pad attaching element; and
a second pad attaching element attached to the wicking layer and barrier layer,
wherein the pad attaching element is attached to the second pad attaching element and for stitching to the garment, the pad attaching element being partially folded to cover the stitching.

28. The absorbent pad according to any one of statements 1 to 27, wherein the peripheral assembly comprises a set of liquid detection elements configured to change state in response to contact with liquid.

29. The absorbent pad according to statement 28, wherein the liquid detection elements comprise a hydrochromic material configured to change colour in response to contact with the liquid.

30. A garment comprising:
a fabric body;
an absorbent pad attached to the fabric body; and
a liquid impermeable barrier layer being part of the fabric body and/or part of the absorbent pad,
wherein the absorbent pad comprises:
a functional assembly attached to the liquid impermeable barrier layer, the functional assembly comprising:
an absorbent layer attached to the liquid impermeable barrier layer, the absorbent layer for absorbing liquid; and
a wicking layer attached to the absorbent layer, the wicking layer arranged to face towards a skin of a user when in use, the wicking layer for transferring liquid to the absorbent layer; and
a peripheral assembly attached to a periphery of the functional assembly, at least part of the peripheral assembly being liquid impermeable,
wherein the wicking layer and the absorbent layer are attached at a plurality of discrete points between them to facilitate liquid transfer from the wicking layer to the absorbent layer via areas around the plurality of discrete points.

31. The garment according to statement 30, wherein the wicking layer and the absorbent layer are knitted together with cross-linking yarns at the discrete points.

32. The garment according to statement 30, wherein the wicking layer and the absorbent layer are attached together by lamination and the discrete points comprise an adhesive material.

33. The garment according to any one of statements 30 to 32, wherein the discrete points are distributed throughout the wicking and absorbent layers and/or at peripheries of the wicking and absorbent layers.

34. The garment according to any one of statements 30 to 33, wherein peripheries of the wicking and absorbent layers are attached together by an adhesive film.

35. The garment according to any one of statements 30 to 34, wherein the wicking layer comprises an array of hydrophobic yarns and hydrophilic yarns that form channels for guiding liquid flow.

36. The garment according to any one of statements 30 to 35, wherein the wicking layer comprises a linear array of hydrophobic material and hydrophilic material.

37. The garment according to statement 36, wherein the wicking layer is made of the hydrophilic material and comprises alternating lines of hydrophobic material disposed on top of the hydrophilic material.

38. The garment according to any one of statements 30 to 35, wherein the functional assembly comprises a top layer attached to the wicking layer and arranged to face towards the user's skin when in use.

39. The garment according to statement 38, wherein the top layer comprises one or more of a hydrophilic material, a hydrophobic material, and a hydrochromic material.

40. The garment according to statement 38 or 39, wherein the top layer comprises an array of openings for liquid transfer from the user's skin to the wicking layer, the top layer comprising a hydrophobic material.

41. The garment according to statement 38 or 39, wherein the top layer comprises an array of channels for guiding liquid flow, the channels comprising a hydrophobic material.

42. The garment according to statement 41, wherein the hydrophobic material comprises a cured polymeric material that is patterned to form the channels.

43. The garment according to statement 38 or 39, wherein the top layer comprises a linear array of hydrophobic material and hydrophilic material.

44. The garment according to statement 43, wherein the top layer is made of the hydrophilic material and comprises alternating lines of hydrophobic material disposed on top of the hydrophilic material.

45. The garment according to any one of statements 38 to 44, wherein the top layer comprises a set of liquid detection elements configured to change state in response to contact with liquid.

46. The garment according to statement 45, wherein the liquid detection elements comprise a hydrochromic material configured to change colour in response to contact with the liquid.

47. The garment according to any one of statements 30 to 46, wherein the wicking layer and/or absorbent layer comprises a foam material and/or a spacer fabric material.

48. The garment according to statement 47, wherein the absorbent pad is moulded such that the functional assembly comprises a deformed portion, the deformed portion being a raised portion or a recessed portion.

49. The garment according to any one of statements 30 to 48, wherein the functional assembly is shaped using darts.

50. The garment according to any one of statements 30 to 49, wherein the peripheral assembly comprises a pad attaching element attached to the periphery of the functional assembly, the pad attaching element optionally being liquid impermeable.

51. The garment according to statement 50, wherein the pad attaching element forms a liquid impermeable ridge on the periphery of the functional assembly.

52. The garment according to statement 50 or 51, the garment further comprising a plurality of fasteners, wherein the peripheral assembly comprises a corresponding plurality of fasteners attached to the pad attaching element, the fasteners configured for fastening the absorbent pad to the garment, the fasteners optionally comprising snap buttons and/or touch fasteners.

53. The garment according to any one of statements 50 to 52, wherein the peripheral assembly comprises:
a first peripheral subassembly arranged along left-right edges of the absorbent pad; and
a second peripheral subassembly arranged along front-rear edges of the absorbent pad,
wherein the first and second peripheral subassemblies are structurally different from each other.

54. The garment according to statement 53, wherein the first peripheral subassembly includes the pad attaching element, the pad attaching element bonded to the wicking layer.

55. The garment according to statement 53 or 54, wherein the second peripheral subassembly comprises:
a sealing element attached to the wicking layer and barrier layer;
the pad attaching element; and
a second pad attaching element attached to the sealing element and stitched to the garment,
wherein the pad attaching element is attached to the second pad attaching element and attached to the garment, the pad attaching element arranged to cover the stitching.

56. The garment according to statement 53 or 54, wherein the second peripheral subassembly comprises:
the pad attaching element; and
a second pad attaching element attached to the wicking layer and barrier layer,
wherein the pad attaching element is attached to the second pad attaching element and stitched to the garment, the pad attaching element being partially folded to cover the stitching.

57. The garment according to any one of statements 30 to 56, wherein the peripheral assembly comprises a set of liquid detection elements configured to change state in response to contact with liquid.

58. The garment according to statement 57, wherein the liquid detection elements comprise a hydrochromic material configured to change colour in response to contact with the liquid.

59. The garment according to any one of statements 30 to 58, further comprising a set of tensioning elements connected to the absorbent pad, the tensioning elements configured for the absorbent pad to compress against the user's body.

60. The garment according to any one of statements 30 to 59, further comprising a pocket, the pocket comprising a laundry bag therein, wherein the laundry bag is removable from the pocket for holding the garment in the laundry bag.

61. The garment according to any one of statements 30 to 60, further comprising a pocket on an outside of the garment, wherein the garment is foldable inwards into the pocket.

62. The garment according to any one of statements 30 to 61, further comprising a second wicking layer fixed to a rear part of the absorbent pad and removably attached to a waistband of the garment, wherein the second wicking layer is detachable from the waistband and reattachable to a front part of the absorbent pad and thereby overlay the second wicking layer on the absorbent pad.

63. The garment according to statement 62, wherein the second wicking layer comprises a set of fasteners for fastening to the front part of the absorbent pad, the fasteners optionally comprising snap buttons and/or touch fasteners.

64. An absorbent pad for use in a garment, the absorbent pad comprising:
a liquid impermeable barrier layer;
a functional assembly attached to the liquid impermeable barrier layer, the functional assembly comprising:
an absorbent layer attached to the liquid impermeable barrier layer, the absorbent layer for absorbing liquid; and
a liquid transport layer attached to the absorbent layer, the liquid transport layer arranged to face towards a skin of a user when in use, the liquid transport layer for transferring liquid to the absorbent layer; and
a peripheral assembly attached to a periphery of the functional assembly, at least part of the peripheral assembly being liquid impermeable,
wherein the liquid transport layer comprises an array of hydrophobic and hydrophilic materials for guiding liquid flow across the functional assembly.

65. The absorbent pad according to statement 64, wherein the functional assembly comprises a wicking layer for transferring liquid to the absorbent layer, the wicking layer comprising the liquid transport layer.

66. The absorbent pad according to statement 65, wherein the hydrophobic and hydrophilic materials comprise hydrophobic and hydrophilic yarns that form channels for guiding liquid flow.

67. The absorbent pad according to statement 65 or 66, wherein the wicking layer comprises a linear array of the hydrophobic material and the hydrophilic material.

68. The absorbent pad according to statement 67, wherein the wicking layer is made of the hydrophilic material and comprises alternating lines of hydrophobic material disposed on top of the hydrophilic material.

69. The absorbent pad according to statement 65, wherein the functional assembly comprises a top layer attached to the wicking layer and arranged to face towards the user's skin when in use, the top layer comprising the liquid transport layer.

70. The absorbent pad according to statement 69, wherein the top layer comprises an array of channels for guiding liquid flow, the channels comprising a hydrophobic material.

71. The absorbent pad according to statement 70, wherein the hydrophobic material comprises a cured polymeric material that is patterned to form the channels.

72. A garment comprising:
a fabric body;
an absorbent pad attached to the fabric body; and
a liquid impermeable barrier layer being part of the fabric body and/or part of the absorbent pad,
wherein the absorbent pad comprises:
a functional assembly attached to the liquid impermeable barrier layer, the functional assembly comprising:
an absorbent layer attached to the liquid impermeable barrier layer, the absorbent layer for absorbing liquid; and
a liquid transport layer attached to the absorbent layer, the liquid transport layer arranged to face towards a skin of a user when in use, the liquid transport layer for transferring liquid to the absorbent layer; and
a peripheral assembly attached to a periphery of the functional assembly, at least part of the peripheral assembly being liquid impermeable,
wherein the liquid transport layer comprises an array of hydrophobic and hydrophilic materials for guiding liquid flow across the functional assembly.

73. The garment according to statement 72, wherein the functional assembly comprises a wicking layer for transferring liquid to the absorbent layer, the wicking layer comprising the liquid transport layer.

74. The garment according to statement 73, wherein the hydrophobic and hydrophilic materials comprise hydrophobic and hydrophilic yarns that form channels for guiding liquid flow.

75. The garment according to statement 73 or 74, wherein the wicking layer comprises a linear array of the hydrophobic material and the hydrophilic material.

76. The garment according to statement 75, wherein the wicking layer is made of the hydrophilic material and comprises alternating lines of hydrophobic material disposed on top of the hydrophilic material.

77. The garment according to statement 73, wherein the functional assembly comprises a top layer attached to the wicking layer and arranged to face towards the user's skin when in use, the top layer comprising the liquid transport layer.

78. The garment according to statement 77, wherein the top layer comprises an array of channels for guiding liquid flow, the channels comprising a hydrophobic material.

79. The garment according to statement 78, wherein the hydrophobic material comprises a cured polymeric material that is patterned to form the channels.

80. An absorbent pad for use in a garment, the absorbent pad comprising:
a liquid impermeable barrier layer;
a functional assembly attached to the liquid impermeable barrier layer, the functional assembly comprising:
an absorbent layer attached to the liquid impermeable barrier layer, the absorbent layer for absorbing liquid; and
a liquid detection layer attached to the absorbent layer, the liquid detection layer arranged to face towards a skin of a user when in use, the liquid detection layer for transferring liquid to the absorbent layer; and
a peripheral assembly attached to a periphery of the functional assembly, at least part of the peripheral assembly being liquid impermeable,
wherein the liquid detection layer comprises a hydrochromic material configured to change colour in response to contact with liquid.

81. The absorbent pad according to statement 80, wherein the functional assembly comprises a wicking layer for transferring liquid to the absorbent layer, the wicking layer comprising the liquid detection layer.

82. The absorbent pad according to statement 81, wherein the functional assembly comprises a top layer attached to the wicking layer and arranged to face towards the user's skin when in use, the top layer comprising liquid detection layer.

83. A garment comprising:
a fabric body;
an absorbent pad attached to the fabric body; and
a liquid impermeable barrier layer being part of the fabric body and/or part of the absorbent pad,
wherein the absorbent pad comprises:
a functional assembly attached to the liquid impermeable barrier layer, the functional assembly comprising:
an absorbent layer attached to the liquid impermeable barrier layer, the absorbent layer for absorbing liquid; and
a liquid detection layer attached to the absorbent layer, the liquid detection layer arranged to face towards a skin of a user when in use, the liquid detection layer for transferring liquid to the absorbent layer; and
a peripheral assembly attached to a periphery of the functional assembly, at least part of the peripheral assembly being liquid impermeable,
wherein the liquid detection layer comprises a hydrochromic material configured to change colour in response to contact with liquid.

84. The garment according to statement 83, wherein the functional assembly comprises a wicking layer for transferring liquid to the absorbent layer, the wicking layer comprising the liquid detection layer.

85. The garment according to statement 84, wherein the functional assembly comprises a top layer attached to the wicking layer and arranged to face towards the user's skin when in use, the top layer comprising liquid detection layer.

The invention claimed is:

1. An absorbent pad for use in a garment, the absorbent pad comprising:
a liquid impermeable barrier layer;
a functional assembly attached to the liquid impermeable barrier layer, the functional assembly comprising:
an absorbent layer attached to the liquid impermeable barrier layer, the absorbent layer for absorbing liquid; and a wicking layer attached to the absorbent layer, the wicking layer arranged to face towards a skin of a user when in use, the wicking layer for transferring liquid to the absorbent layer; and a peripheral assembly attached to a periphery of the functional assembly, at least part of the peripheral assembly being liquid impermeable, wherein the wicking layer and the absorbent layer are attached to each other at a plurality of attachment areas, each attachment area comprising a plurality of discrete attachment points between the wicking layer and the absorbent layer to facilitate liquid transfer from the wicking layer to the absorbent layer via adjacent areas around the discrete attachment points, the adjacent areas disposed within the respective attachment area; and wherein the peripheral assembly comprises a liquid-impermeable pad attaching element attached to the periphery of the functional assembly and for attaching the absorbent pad to the garment, the pad attaching element overlaying a periphery of the wicking layer to reduce overflow of liquid from the periphery of the wicking layer.

2. The absorbent pad according to claim 1, wherein the wicking layer and the absorbent layer are knitted together with cross-linking yarns at the plurality of discrete attachment points between the wicking layer and the absorbent layer.

3. The absorbent pad according to claim 1, wherein the wicking layer and the absorbent layer are attached together by lamination at the plurality of discrete attachment points between the wicking layer and the absorbent layer, and wherein the discrete attachment points comprise an adhesive material.

4. The absorbent pad according to claim 1, wherein the wicking layer comprises an array of hydrophobic yarns and hydrophilic yarns that form channels for guiding liquid flow.

5. The absorbent pad according to claim 1, wherein the wicking layer comprises a linear array of hydrophobic material and hydrophilic material.

6. The absorbent pad according to claim 5, wherein the wicking layer is made of the hydrophilic material and comprises alternating lines of hydrophobic material disposed on top of the hydrophilic material.

7. The absorbent pad according to claim 1, wherein the functional assembly comprises a top layer attached to the wicking layer and arranged to face towards the user's skin when in use.

8. The absorbent pad according to claim 7, wherein the top layer comprises one or more of a hydrophilic material, a hydrophobic material, and a hydrochromic material.

9. The absorbent pad according to claim 7, wherein the top layer comprises an array of openings for liquid transfer from the user's skin to the wicking layer, the top layer comprising a hydrophobic material.

10. The absorbent pad according to claim 7, wherein the top layer comprises a hydrochromic material configured to change colour in response to contact with liquid.

11. The absorbent pad according to claim 1, wherein the wicking layer and/or absorbent layer comprises a foam material and/or a spacer fabric material.

12. The absorbent pad according to claim 11, wherein the absorbent pad is moulded such that the functional assembly comprises a deformed portion, the deformed portion being a raised portion or a recessed portion.

13. The absorbent pad according to claim 1, wherein the peripheral assembly comprises:

a first peripheral subassembly arranged along a front and rear of the absorbent pad; and a second peripheral subassembly arranged along a left and right of the absorbent pad, wherein the first and second peripheral subassemblies are structurally different from each other.

14. The absorbent pad according to claim 13, wherein the first peripheral subassembly includes the pad attaching element.

15. The absorbent pad according to claim 13, wherein the second peripheral subassembly comprises:

a sealing element attached to the wicking layer and barrier layer;

the pad attaching element; and a second pad attaching element attached to the sealing element and for stitching to the garment, wherein the pad attaching element is attached to the second pad attaching element and for attaching to the garment, the pad attaching element arranged to cover the stitching.

16. The absorbent pad according to claim 13, wherein the second peripheral subassembly comprises:

the pad attaching element; and a second pad attaching element attached to the wicking layer and barrier layer, wherein the pad attaching element is attached to the second pad attaching element and for stitching to the garment, the pad attaching element being partially folded to cover the stitching.

17. The absorbent pad according to claim 14, wherein the second peripheral subassembly comprises:

a sealing element attached to the wicking layer and barrier layer;

the pad attaching element; and a second pad attaching element attached to the sealing element and for stitching to the garment, wherein the pad attaching element is attached to the second pad attaching element and for attaching to the garment, the pad attaching element arranged to cover the stitching.

18. The absorbent pad according to claim 14, wherein the second peripheral subassembly comprises:

the pad attaching element; and a second pad attaching element attached to the wicking layer and barrier layer, wherein the pad attaching element is attached to the second pad attaching element and for stitching to the garment, the pad attaching element being partially folded to cover the stitching.

19. The absorbent pad according to claim 1, wherein the functional assembly and/or peripheral assembly comprises a hydrochromic material configured to change colour in response to contact with liquid.

* * * * *

UNITED STATES PATENT AND TRADEMARK OFFICE
CERTIFICATE OF CORRECTION

| | | |
|---|---|---|
| PATENT NO. | : 12,178,690 B2 | Page 1 of 1 |
| APPLICATION NO. | : 18/506253 | |
| DATED | : December 31, 2024 | |
| INVENTOR(S) | : Mapitiyage Don Janith Dushyantha et al. | |

It is certified that error appears in the above-identified patent and that said Letters Patent is hereby corrected as shown below:

On the Title Page

Inventor Item (72) Line 7:
Delete: "Malabe (CA)" and Insert --Malabe (LK)--

Signed and Sealed this
Twenty-fifth Day of March, 2025

Coke Morgan Stewart
*Acting Director of the United States Patent and Trademark Office*